(12) United States Patent
Kaiser et al.

(10) Patent No.: US 9,044,016 B2
(45) Date of Patent: Jun. 2, 2015

(54) N-THIO-ANTHRANILAMIDE COMPOUNDS AND THEIR USE AS PESTICIDES

(75) Inventors: Florian Kaiser, Mannheim (DE); Karsten Körber, Eppelheim (DE); Prashant Deshmukh, Mannheim (DE); Deborah L. Culbertson, Fuquay Varina, NC (US); Paul Neese, Apex, NC (US); Koshi Gunjima, Cary, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/235,528

(22) PCT Filed: Aug. 10, 2012

(86) PCT No.: PCT/EP2012/065650
§ 371 (c)(1),
(2), (4) Date: Jan. 28, 2014

(87) PCT Pub. No.: WO2013/024009
PCT Pub. Date: Feb. 21, 2013

(65) Prior Publication Data
US 2014/0155264 A1 Jun. 5, 2014

Related U.S. Application Data

(60) Provisional application No. 61/522,721, filed on Aug. 12, 2011.

(51) Int. Cl.
*A01N 43/56* (2006.01)
*C07D 401/04* (2006.01)
*C07D 409/14* (2006.01)

(52) U.S. Cl.
CPC .............. *A01N 43/56* (2013.01); *C07D 401/04* (2013.01); *C07D 409/14* (2013.01)

(58) Field of Classification Search
CPC ..... A01N 43/56; C07D 401/04; C07D 409/14
USPC .......... 424/405; 504/100, 130, 139, 149, 253, 504/282, 326, 337; 514/236.5, 277, 341, 514/357, 406; 546/275.4; 548/364.1, 369.7; 564/102, 152, 155, 189
See application file for complete search history.

(56) References Cited

U.S. PATENT DOCUMENTS 8,143,292 B2 * 3/2012 Schmidt et al. ............... 514/341
8,338,419 B2 * 12/2012 Schmidt et al. ............ 514/236.5

FOREIGN PATENT DOCUMENTS

| | | | |
|---|---|---|---|
| EP | 2281810 | 2/2011 | |
| NL | 9202078 | 6/1994 | |
| WO | WO 0170671 | 9/2001 | |
| WO | WO 02070483 | 9/2002 | |
| WO | WO 03015518 | 2/2003 | |
| WO | WO 03015519 | 2/2003 | |
| WO | WO 03016284 | 2/2003 | |
| WO | WO 03016300 | 2/2003 | |
| WO | WO 03024222 | 3/2003 | |
| WO | WO 2004033468 | 4/2004 | |
| WO | WO 2004046129 | 6/2004 | |
| WO | WO 2005085234 | 9/2005 | |
| WO | WO 2006000336 | 1/2006 | |
| WO | WO 2006040113 | 4/2006 | |
| WO | WO 2006068669 | 6/2006 | |
| WO | WO 2007006670 | 1/2007 | |
| WO | WO 2007006670 A1 * | 1/2007 | ........... C07D 401/04 |
| WO | WO 2007024833 | 3/2007 | |
| WO | WO 2007043677 | 4/2007 | |
| WO | WO 2008130021 | 10/2008 | |
| WO | WO 2011117804 | 9/2011 | |
| WO | WO 2011117806 | 9/2011 | |
| WO | WO 2012034960 | 3/2012 | |
| WO | WO 2012034961 | 3/2012 | |
| WO | WO 2013024003 | 2/2013 | |
| WO | WO 2013024004 | 2/2013 | |
| WO | WO 2013024005 | 2/2013 | |
| WO | WO 2013024006 | 2/2013 | |
| WO | WO 2013024007 | 2/2013 | |
| WO | WO 2013024008 | 2/2013 | |
| WO | WO 2013024009 | 2/2013 | |
| WO | WO 2013024010 | 2/2013 | |

OTHER PUBLICATIONS

International Search Report, issued in PCT/EP2012/065650, dated Sep. 25, 2012.
International Preliminary Report on Patentability, issued in PCT/EP2012/065650, dated Jul. 15, 2013.

* cited by examiner

*Primary Examiner* — Jane C Oswecki
(74) *Attorney, Agent, or Firm* — Brinks Gilson & Lione

(57) ABSTRACT

The present invention relates to N-thio-anthranilamide compounds of the formula (I), the stereoisomers, the salts, the tautomers and the N-oxides thereof,

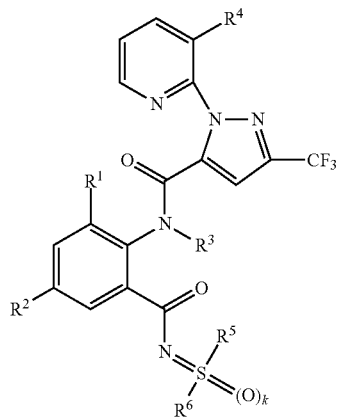
(I)

wherein $R^1$ is halogen or halomethyl; $R^2$ is hydrogen, halogen or cyano; $R^3$ is hydrogen, $C_1$-$C_4$ alkyl, $C_1$-$C_4$ haloalkyl, $C_2$-$C_6$-alkenyl or the like; $R^4$ is halogen; $R^5$ and $R^6$ independently of each other are optionally substituted $C_1$-$C_6$-alkyl, $C_3$-$C_6$-cycloalkyl, $C_2$-$C_6$-alkenyl, $C_2$-$C_6$-alkynyl, phenyl, or together represent an (hetero)aliphatic chain, or the like; k is 0 or 1.

The present invention further relates to a method for combating or controlling invertebrate pests, to a method for protecting plant propagation material and/or the plants which grow therefrom, to plant propagation material comprising at least one compound according to the present invention, to a method for treating or protecting an animal from infestation or infection by parasites, to a process for the preparation of a composition for treating infested or infected animals and/or for protecting animals against infestation or infection by parasites, and to a compound according to the invention for use as a medicament.

31 Claims, 1 Drawing Sheet

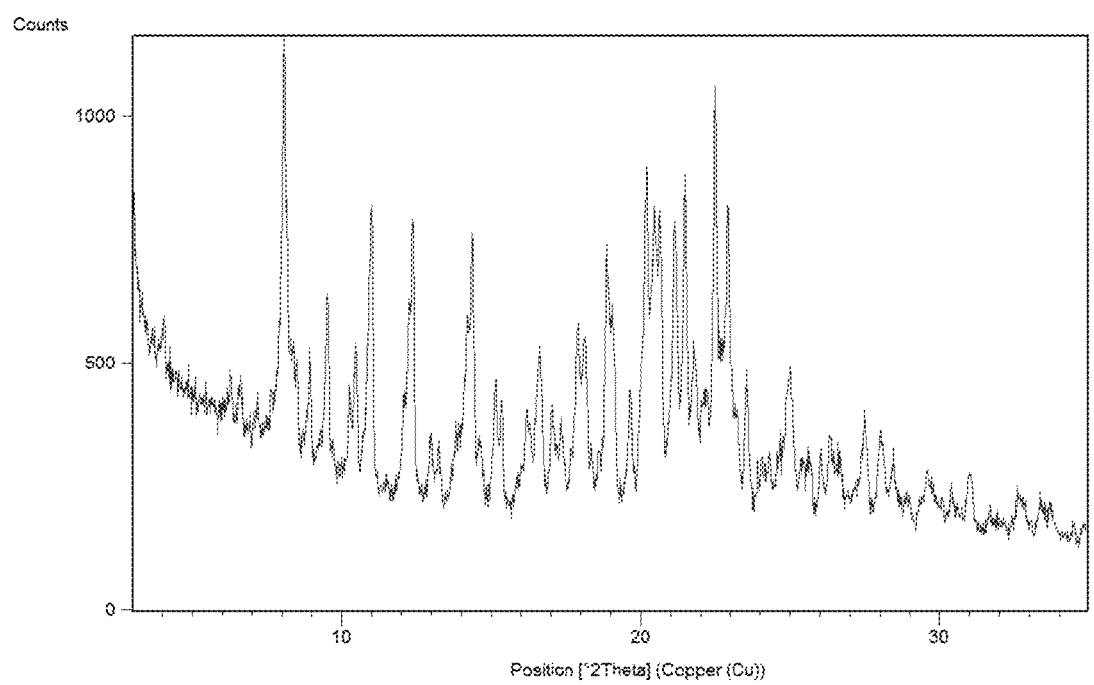

N-THIO-ANTHRANILAMIDE COMPOUNDS AND THEIR USE AS PESTICIDES

This application is a National Stage application of International Application No. PCT/EP2012/065650, filed Aug. 10, 2012, which claims the benefit of U.S. Provisional Application No. 61/522,721, filed Aug. 12, 2011, the entire contents of which are hereby incorporated herein by reference.

The present invention relates to N-thio-anthranilamide compounds and the stereoisomers, salts, tautomers and N-oxides thereof and to compositions comprising the same. The invention also relates to the use of the N-thio-anthranilamide compounds or of the compositions comprising such compounds for combating invertebrate pests. Furthermore, the invention relates to methods of applying such compounds.

Invertebrate pests and in particular insects, arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

Anthranilamide compounds have been described in a number of patent applications (e.g. WO 01/70671, WO 03/015518, WO 03/024222, WO 2006/000336, WO 2006/068669, WO 2007/043677, WO 2008/130021, WO 03/015519, WO 2004/046129). WO 03/016300 describes a generic anthranilamide formula encompassing N-thio-anthranilamide compounds. WO 03/016284 describes inter alia certain N-thio-anthranilamide compounds. WO 2007/006670 describes N-thio-anthranilamide compounds with a sulfilimine or sulfoximine group and their use as pesticides.

It is an object of the present invention to provide further compounds having a high pesticidal activity against invertebrate pests, in particular against insect pest. The compounds should show a broad activity spectrum against a large number of different invertebrate pests, in particular against difficult to control insects, arachnids and nematodes.

It has been found that the above objectives can be achieved by N-thio-anthranilamide compounds of the general formula (I), as defined below, including their stereoisomers, their salts, in particular their agriculturally or veterinarily acceptable salts, their tautomers and their N-oxides.

Therefore, in a first aspect the present invention relates to compounds of formula (I),

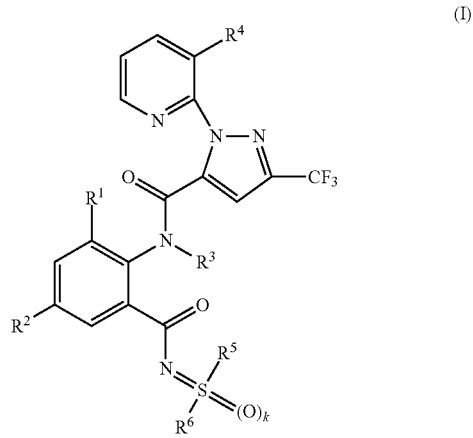

(I)

wherein
$R^1$ is selected from the group consisting of halogen and halomethyl;
$R^2$ is selected from the group consisting of hydrogen, halogen, halomethyl and cyano, in particular from the group consisting of hydrogen, halogen and cyano;
$R^3$ is selected from hydrogen, $C_1$-$C_6$ alkyl, $C_1$-$C_6$ haloalkyl, $C_2$-$C_6$-alkenyl, $C_2$-$C_6$-haloalkenyl, $C_2$-$C_6$-alkinyl, $C_2$-$C_6$-haloalkinyl, $C_3$-$C_8$-cycloalkyl, $C_3$-$C_8$-halocycloalkyl, $C_1$-$C_4$-alkoxy-$C_1$-$C_4$-alkyl, $C_1$-$C_4$-haloalkoxy-$C_1$-$C_4$-alkyl, $C(=O)R^a$, $C(=O)OR^b$ and $C(=O)NR^cR^d$;
$R^4$ is halogen;
$R^5$, $R^6$ are selected independently of one another from the group consisting of hydrogen, $C_1$-$C_{10}$-alkyl, $C_3$-$C_8$-cycloalkyl, $C_2$-$C_{10}$-alkenyl, $C_2$-$C_{10}$-alkynyl, wherein the aforementioned aliphatic and cycloaliphatic radicals may be substituted with 1 to 10 substituents $R^e$, and phenyl, which is unsubstituted or carries 1 to 5 substituents $R^f$; or
$R^5$ and $R^6$ together represent a $C_2$-$C_7$-alkylene, $C_2$-$C_7$-alkenylene or $C_6$-$C_9$-alkynylene chain forming together with the sulfur atom to which they are attached a 3-, 4-, 5-, 6-, 7-, 8-, 9- or 10-membered saturated, partially unsaturated or fully unsaturated ring, wherein 1 to 4 of the $CH_2$ groups in the $C_2$-$C_7$-alkylene chain or 1 to 4 of any of the $CH_2$ or CH groups in the $C_2$-$C_7$-alkenylene chain or 1 to 4 of any of the $CH_2$ groups in the $C_6$-$C_9$-alkynylene chain may be replaced by 1 to 4 groups independently selected from the group consisting of $C=O$, $C=S$, O, S, N, NO, SO, $SO_2$ and NH, and wherein the carbon and/or nitrogen atoms in the $C_2$-$C_7$-alkylene, $C_2$-$C_7$-alkenylene or $C_6$-$C_9$-alkynylene chain may be substituted with 1 to 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl and $C_2$-$C_6$-haloalkynyl; said substituents being identical or different from one another if more than one substituent is present;
$R^a$ is selected from the group consisting of $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, $C_1$-$C_6$-alkylthio, $C_1$-$C_6$-alkylsulfinyl, $C_1$-$C_6$-alkylsulfonyl, wherein one or more $CH_2$ groups of the aforementioned radicals may be replaced by a $C=O$ group, and/or the aliphatic and cycloaliphatic moieties of the aforementioned radicals may be unsubstituted, partially or fully halogenated and/or may carry 1 or 2 substituents selected from $C_1$-$C_4$ alkoxy; phenyl, benzyl, pyridyl and phenoxy, wherein the last four radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy, ($C_1$-$C_6$-alkoxy)carbonyl, $C_1$-$C_6$-alkylamino and di-($C_1$-$C_6$-alkyl)amino,
$R^b$ is selected from the group consisting of $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, $C_1$-$C_6$-alkylthio, $C_1$-$C_6$-alkylsulfinyl, $C_1$-$C_6$-alkylsulfonyl, wherein one or more $CH_2$ groups of the aforementioned radicals may be replaced by a $C=O$ group, and/or the aliphatic and cycloaliphatic moieties of the aforementioned radicals may be unsubstituted, partially or fully halogenated and/or may carry 1 or 2 substituents selected from $C_1$-$C_4$-alkoxy; phenyl, benzyl, pyridyl and phenoxy, wherein the last four radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;
$R^c$, $R^d$ are, independently from one another and independently of each occurrence, selected from the group consisting of hydrogen, cyano, $C_1$-$C_6$-alkyl, $C_2$-$C_6$-alkenyl, $C_2$-$C_6$-alkinyl, $C_3$-$C_8$-cycloalkyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 radicals selected from $C_1$-$C_4$-alkoxy;

$C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, phenyl, benzyl, pyridyl and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl; or $R^c$ and $R^d$, together with the nitrogen atom to which they are bound, may form a 3-, 4-, 5-, 6- or 7-membered saturated, partially unsaturated or fully unsaturated heterocyclic ring which may additionally contain 1 or 2 further heteroatoms or heteroatom groups selected from N, O, S, NO, SO and $SO_2$, as ring members, where the heterocyclic ring may optionally be substituted with halogen, $C_1$-$C_4$-haloalkyl, $C_1$-$C_4$-alkoxy or $C_1$-$C_4$-haloalkoxy;

$R^e$ is independently selected from the group consisting of halogen, cyano, nitro, —OH, —SH, —SCN, $C_1$-$C_6$-alkyl, $C_2$-$C_6$-alkenyl, $C_2$-$C_6$-alkinyl, $C_3$-$C_8$-cycloalkyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 radicals selected from $C_1$-$C_4$ alkoxy; $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, —$OR^a$, —$NR^cR^d$, —$S(O)_nR^a$, —$S(O)_nNR^cR^d$, —C(=O)$R^a$, —C(=O)$NR^cR^d$, —C(=O)$OR^b$, —C(=S)$R^a$, —C(=S)$NR^cR^d$, —C(=S)$OR^b$, —C(=S)$SR^b$, —C(=$NR^c$)$R^b$, —C(=$NR^c$)$NR^cR^d$, phenyl, benzyl, pyridyl and phenoxy, wherein the last four radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy and $C_1$-$C_6$-haloalkoxy; or two vicinal radicals $R^e$ together form a group =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

$R^f$ is independently selected from the group consisting of halogen, cyano, nitro, —OH, —SH, —SCN, $C_1$-$C_6$-alkyl, $C_2$-$C_6$-alkenyl, $C_2$-$C_6$-alkinyl, $C_3$-$C_8$-cycloalkyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 radicals selected from $C_1$-$C_4$ alkoxy;

$C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, —$OR^a$, —$NR^cR^d$, —$S(O)_nR^a$, —$S(O)_nNR^cR^d$, —C(=O)$R^a$, —C(=O)$NR^cR^d$, —C(=O)$OR^b$, —C(=S)$R^a$, —C(=S)$NR^cR^d$, —C(=S)$OR^b$, —C(=S)$SR^b$, —C(=$NR^c$)$R^b$, and —C(=$NR^c$)$NR^cR^d$;

k is 0 or 1;

n is 0, 1 or 2;

or a stereoisomer, salt, tautomer or N-oxide thereof.

Furthermore, the invention relates to processes for the synthesis of compounds according to the invention and to intermediate compounds for the synthesis of compounds of formula (I). Yet, a further aspect of the present invention relates to crystalline form of 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide which, in an X-ray powder diffractogram at 25° C. and Cu-$K_\alpha$ radiation, shows at least four, frequently at least 5, in particular at least 7, especially at least 9 or all of the following 10 reflexes, given as 2θ values: 8.07, 9.53, 11.00, 12.40, 14.31, 16.65, 18.97, 21.14, 21.48 and 22.48.

The compounds of the present invention, i.e. the compounds of formula (I), their stereoisomers, their salts, their tautomers, their polymorphs or their N-oxides, are particularly useful for controlling invertebrate pests, in particular for controlling arthropods and nematodes and especially insects. Therefore, the invention also relates to the use of a compound of the present invention, for combating or controlling invertebrate pests, in particular invertebrate pests of the group of insects, arachnids or nematodes.

The invention also relates to a composition comprising at least one compound according to the invention, including a stereoisomer, salt, tautomer or N-oxide thereof, and at least one inert liquid and/or solid carrier. In particular, the invention relates to an agricultural or veterinary composition comprising at least one compound according to the invention including a stereoisomer, an agriculturally or veterinarily acceptable salt, tautomer or an N-oxide thereof, and at least one liquid and/or solid carrier.

The present invention also relates to a method for combating or controlling invertebrate pests, especially invertebrate pests of the group of insects, arachnids or nematodes, which method comprises contacting said pest or its food supply, habitat or breeding grounds with a pesticidally effective amount of at least one compound according to the invention including a stereoisomer, salt, tautomer or N-oxide thereof or a composition according to the invention.

The present invention also relates to a method for protecting growing plants from attack or infestation by invertebrate pests, especially invertebrate pests of the group of insects, arachnids or nematodes, which method comprises contacting a plant, or soil or water in which the plant is growing or may grow, with a pesticidally effective amount of at least one compound according to the invention including a stereoisomer, salt, tautomer or N-oxide thereof or a composition according to the invention.

The present invention also relates to a method for the protection of plant propagation material, preferably seeds, from soil insects and of the seedlings' roots and shoots from soil and foliar insects comprising contacting the seeds before sowing and/or after pregermination with at least one compound according to the invention including a stereoisomer, salt, tautomer or N-oxide thereof or a composition according to the invention.

The present invention also relates to plant propagation material, preferably seed, comprising a compound according to the invention including a stereoisomer, salt, tautomer or N-oxide thereof, preferably in an amount of from 0.1 g to 10 kg per 100 kg of the plant propagation material.

The present invention also relates to the use of a compound according to the invention including a stereoisomer, salt, tautomer or N-oxide thereof or a composition according to the invention for combating or controlling invertebrate pests of the group of insects, arachnids or nematodes.

The present invention also relates to the use of a compound according to the invention including a stereoisomer, salt or N-oxide thereof or a composition according to the invention for protecting growing plants from attack or infestation by invertebrate pests of the group of insects, arachnids or nematodes.

The present invention also relates to the use of a compound according to the invention including a stereoisomer, veterinarily acceptable salt, tautomer or N-oxide thereof or a composition according to the invention for combating or controlling invertebrate parasites in and on animals.

The present invention also relates to a method for treating a non-human animal infested or infected by parasites or for preventing a non-human animal from getting infested or infected by parasites or for protecting a non-human animal against infestation or infection by parasites which comprises orally, topically or parenterally administering or applying to the non-human animal a parasiticidally effective amount of a compound according to the invention including a stereoisomer, veterinarily acceptable salt, tautomer or N-oxide thereof or a composition according to the invention.

The present invention also relates to the use of a compound according to the invention including a stereoisomer, veterinarily acceptable salt or N-oxide thereof or a composition according to the invention for the manufacture of a medicament for protecting an animal against infestation or infection by parasites or treating an animal infested or infected by parasites.

The present invention also relates to a process for the preparation of a composition for treating animals infested or infected by parasites, for preventing animals of getting infected or infested by parasites or protecting animals against infestation or infection by parasites which comprises a compound according to the invention including a stereoisomer, veterinarily acceptable salt, tautomer or N-oxide thereof.

The present invention also relates to a compound according to the invention including a stereoisomer, veterinarily acceptable salt, tautomer or N-oxide thereof for use as a medicament.

The present invention also relates to a compound according to the invention including a stereoisomer, veterinarily acceptable salt, tautomer or N-oxide thereof for use in the treatment, control, prevention or protection of animals against infestation or infection by parasites.

Depending on the substitution pattern, the compounds of the formula (I) may have one or more centers of chirality, in which case they are present as mixtures of enantiomers or diastereomers. The invention provides both the pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond, nitrogen-sulfur double bond or amide group. The term "stereoisomer(s)" encompasses both optical isomers, such as enantiomers or diastereomers, the latter existing due to more than one center of chirality in the molecule, as well as geometrical isomers (cis/trans isomers).

Depending on the substitution pattern, the compounds of the formula (I) may be present in the form of their tautomers. Hence the invention also relates to the tautomers of the formula (I) and the stereoisomers, salts, tautomers and N-oxides of said tautomers.

The term "N-oxide" includes any compound of the present invention which has at least one tertiary nitrogen atom that is oxidized to an N-oxide moiety. N-oxides of in compounds (I) can in particular be prepared by oxidizing the ring nitrogen atom(s) of the pyridine ring and/or the pyrazole ring with a suitable oxidizing agent, such as peroxo carboxylic acids or other peroxides.

The compounds of the present invention may be amorphous or may exist in one ore more different crystalline states (polymorphs) which may have different macroscopic properties such as stability or show different biological properties such as activities. The present invention includes both amorphous and crystalline compounds of formula (I), their enantiomers or diastereomers, mixtures of different crystalline states of the respective compound of formula (I), its enantiomers or diastereomers, as well as amorphous or crystalline salts thereof.

Salts of the compounds of the present invention are preferably agriculturally and veterinarily acceptable salts. They can be formed in a customary method, e.g. by reacting the compound with an acid if the compound of the present invention has a basic functionality or by reacting the compound with a suitable base if the compound of the present invention has an acidic functionality.

Suitable agriculturally acceptable salts are especially the salts of those cations or the acid addition salts of those acids whose cations and anions, respectively, do not have any adverse effect on the pesticidal action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of the present invention with an acid of the corresponding anion, preferably with hydrochloric acid, hydrobromic acid, sulfuric acid, phosphoric acid or nitric acid.

Veterinarily acceptable salts of the compounds of the present invention encompass the salts of those cations or the acid addition salts which are known and accepted in the art for the formation of salts for veterinary use. Suitable acid addition salts, e.g. formed by compounds of the present invention containing a basic nitrogen atom, e.g. an amino group, include salts with inorganic acids, for example hydrochlorides, sulphates, phosphates, and nitrates and salts of organic acids for example acetic acid, maleic acid, e.g. the monoacid salts or diacid salts of maleic acid, dimaleic acid, fumaric acid, e.g. the monoacid salts or diacid salts of fumaric acid, difumaric acid, methane sulfenic acid, methane sulfonic acid, and succinic acid.

The term "invertebrate pest" as used herein encompasses animal populations, such as arthropode pests, including insects and arachnids, as well as nematodes, which may attack plants thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "plants" comprises any types of plants including "non-cultivated plants" and in particular "cultivated plants".

The term "non-cultivated plants" refers to any wild type species or related species or related genera of a cultivated plant.

The term "cultivated plants" is to be understood as including plants which have been modified by breeding, mutagenesis or genetic engineering. Genetically modified plants are plants, the genetic material of which has been modified by the use of recombinant DNA techniques so that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides), e.g. by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat Protoc. 2007; 2(5): 1225-35., Curr Opin Chem. Biol. 2006 October; 10(5):487-91. Epub 2006 Aug 28., Biomaterials. 2001 March; 22(5):405-17, Bioconjug. Chem. 2005 Janurary-February; 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as endotoxins, e.g. CryIA(b), CryIA(c), CryIF, CryIF(a2), CryIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine. A partially or fully halogenated radical is termed below also "halo-radical". For example, partially or fully halogenated alkyl is also termed haloalkyl.

The term "alkyl" as used herein (and in the alkyl moieties of other groups comprising an alkyl group, e.g. alkoxy, alkylcarbonyl, alkylthio, alkylsulfinyl, alkylsulfonyl and alkoxyalkyl) denotes in each case a straight-chain or branched alkyl group having usually from 1 to 10 carbon atoms, frequently from 1 to 6 carbon atoms, preferably 1 to 4 carbon atoms and in particular from 1 to 3 carbon atoms. Examples of $C_1$-$C_4$-alkyl are methyl, ethyl, n-propyl, iso-propyl, n-butyl, 2-butyl (sec-butyl), isobutyl and tert-butyl. Examples for $C_1$-$C_6$-alkyl are, apart those mentioned for $C_1$-$C_4$-alkyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Examples for $C_1$-$C_{10}$-alkyl are, apart those mentioned for $C_1$-$C_6$-alkyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl, 1-propylpentyl, 2-propylpentyl, nonyl, decyl, 2-propylheptyl and 3-propylheptyl.

The term "alkylene" (or alkanediyl) as used herein in each case denotes an alkyl radical as defined above, wherein one hydrogen atom at any position of the carbon backbone is replaced by one further binding site, thus forming a bivalent moiety.

The term "haloalkyl" as used herein (and in the haloalkyl moieties of other groups comprising a haloalkyl group, e.g. haloalkoxy, haloalkylthio, haloalkylcarbonyl, haloalkylsulfonyl and haloalkylsulfinyl) denotes in each case a straight-chain or branched alkyl group having usually from 1 to 10 carbon atoms ("$C_1$-$C_{10}$-haloalkyl"), frequently from 1 to 6 carbon atoms ("$C_1$-$C_6$-haloalkyl"), more frequently 1 to 4 carbon atoms ("$C_1$-$C_{10}$-haloalkyl"), wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, more preferably from halomethyl, in particular from $C_1$-$C_2$-fluoroalkyl. Halomethyl is methyl in which 1, 2 or 3 of the hydrogen atoms are replaced by halogen atoms. Examples are bromomethyl, chloromethyl, dichloromethyl, trichloromethyl, fluoromethyl, difluoromethyl, trifluoromethyl, chlorofluoromethyl, dichlorofluoromethyl, chlorodifluoromethyl and the like. Examples for $C_1$-$C_2$-fluoroalkyl are fluoromethyl, difluoromethyl, trifluoromethyl, 1-fluoroethyl, 2-fluoroethyl, 2,2-difluoroethyl, 2,2,2-trifluoroethyl, pentafluoroethyl, and the like. Examples for $C_1$-$C_2$-haloalkyl are, apart those mentioned for $C_1$-$C_2$-fluoroalkyl, chloromethyl, dichloromethyl, trichloromethyl, bromomethyl, chlorofluoromethyl, dichlorofluoromethyl, chlorodifluoromethyl, 1-chloroethyl, 2-chloroethyl, 2,2-dichloroethyl, 2,2,2-trichloroethyl, 2-chloro-2-fluoroethyl, 2-chloro-2,2-difluoroethyl, 2,2-dichloro-2-fluoroethyl, 1-bromoethyl, and the like. Examples for $C_1$-$C_4$-haloalkyl are, apart those mentioned for $C_1$-$C_2$-haloalkyl, 1-fluoropropyl, 2-fluoropropyl, 3-fluoropropyl, 3,3-difluoropropyl, 3,3,3-trifluoropropyl, heptafluoropropyl, 1,1,1-trifluoroprop-2-yl, 3-chloropropyl, 4-chlorobutyl and the like.

The term "cycloalkyl" as used herein (and in the cycloalkyl moieties of other groups comprising a cycloalkyl group, e.g. cycloalkoxy and cycloalkylalkyl) denotes in each case a mono- or bicyclic cycloaliphatic radical having usually from 3 to 10 carbon atoms ("$C_3$-$C_{10}$-cycloalkyl"), preferably 3 to 8 carbon atoms ("$C_3$-$C_8$-cycloalkyl") or in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.1.1]hexyl, bicyclo[2.2.1]heptyl, bicyclo[3.1.1]heptyl, bicyclo[2.2.1]heptyl, bicyclo[2.2.2]octyl and bicyclo[3.2.1]octyl.

The term "halocycloalkyl" as used herein (and in the halocycloalkyl moieties of other groups comprising an halocycloalkyl group, e.g. halocycloalkylmethyl) denotes in each case a mono- or bicyclic cycloaliphatic radical having usually from 3 to 10 carbon atoms, preferably 3 to 8 carbon atoms or in particular 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "cycloalkyl-alkyl" used herein denotes a cycloalkyl group, as defined above, which is bound to the remainder of the molecule via an alkylene group. The term "$C_3$-$C_8$-cycloalkyl-$C_1$-$C_4$-alkyl" refers to a $C_3$-$C_8$-cycloalkyl group as defined above which is bound to the remainder of the molecule via a $C_1$-$C_4$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, and the like.

The term "alkenyl" as used herein denotes in each case a monounsaturated straight-chain or branched hydrocarbon radical having usually 2 to 10 ("$C_2$-$C_{10}$-alkenyl"), preferably 2 to 6 carbon atoms ("$C_2$-$C_6$-alkenyl"), in particular 2 to 4 carbon atoms ("$C_2$-$C_4$-alkenyl"), and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "alkenylene" (or alkenediyl) as used herein in each case denotes an alkenyl radical as defined above, wherein one hydrogen atom at any position of the carbon backbone is replaced by one further binding site, thus forming a bivalent moiety.

The term "haloalkenyl" as used herein, which may also be expressed as "alkenyl which may be substituted by halogen", and the haloalkenyl moieties in haloalkenyloxy, haloalkenylcarbonyl and the like refers to unsaturated straight-chain or branched hydrocarbon radicals having 2 to 10 ("$C_2$-$C_{10}$-haloalkenyl") or 2 to 6 ("$C_2$-$C_6$-haloalkenyl") or 2 to 4 ("$C_2$-$C_4$-haloalkenyl") carbon atoms and a double bond in any position, where some or all of the hydrogen atoms in these groups are replaced by halogen atoms as mentioned above, in particular fluorine, chlorine and bromine, for example chlorovinyl, chloroallyl and the like.

The term "alkynyl" as used herein denotes unsaturated straight-chain or branched hydrocarbon radicals having usually 2 to 10 ("$C_2$-$C_{10}$-alkynyl"), frequently 2 to 6 ("$C_2$-$C_6$-alkynyl"), preferably 2 to 4 carbon atoms ("$C_2$-$C_4$-alkynyl") and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

The term "alkynylene" (or alkynediyl) as used herein in each case denotes an alkynyl radical as defined above, wherein one hydrogen atom at any position of the carbon backbone is replaced by one further binding site, thus forming a bivalent moiety.

The term "haloalkynyl" as used herein, which is also expressed as "alkynyl which may be substituted by halogen", refers to unsaturated straight-chain or branched hydrocarbon radicals having usually 3 to 10 carbon atoms ("$C_2$-$C_{10}$-haloalkynyl"), frequently 2 to 6 ("$C_2$-$C_6$-haloalkynyl"), preferably 2 to 4 carbon atoms ("$C_2$-$C_4$-haloalkynyl"), and one or two triple bonds in any position (as mentioned above), where some or all of the hydrogen atoms in these groups are replaced by halogen atoms as mentioned above, in particular fluorine, chlorine and bromine.

The term "alkoxy" as used herein denotes in each case a straight-chain or branched alkyl group usually having from 1 to 10 carbon atoms ("$C_1$-$C_{10}$-alkoxy"), frequently from 1 to 6 carbon atoms ("$C_1$-$C_6$-alkoxy"), preferably 1 to 4 carbon atoms ("$C_1$-$C_4$-alkoxy"), which is bound to the remainder of the molecule via an oxygen atom. $C_1$-$C_2$-Alkoxy is methoxy or ethoxy. $C_1$-$C_4$-Alkoxy is additionally, for example, n-propoxy, 1-methylethoxy(isopropoxy), butoxy, 1-methylpropoxy(sec-butoxy), 2-methylpropoxy(isobutoxy) or 1,1-dimethylethoxy(tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "haloalkoxy" as used herein denotes in each case a straight-chain or branched alkoxy group, as defined above, having from 1 to 10 carbon atoms ("$C_1$-$C_{10}$-haloalkoxy"), frequently from 1 to 6 carbon atoms ("$C_1$-$C_6$-haloalkoxy"), preferably 1 to 4 carbon atoms ("$C_1$-$C_4$-haloalkoxy"), more preferably 1 to 3 carbon atoms ("$C_1$-$C_3$-haloalkoxy"), wherein the hydrogen atoms of this group are partially or totally replaced with halogen atoms, in particular fluorine atoms. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "alkoxyalkyl" as used herein denotes in each case alkyl usually comprising 1 to 6 carbon atoms, preferably 1 to 4 carbon atoms, wherein 1 carbon atom carries an alkoxy radical usually comprising 1 to 10, frequently 1 to 6, in particular 1 to 4, carbon atoms as defined above. "$C_1$-$C_6$-Alkoxy-$C_1$-$C_6$-alkyl" is a $C_1$-$C_6$-alkyl group, as defined above, in which one hydrogen atom is replaced by a $C_1$-$C_6$-alkoxy group, as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methyl-propoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "haloalkoxy-alkyl" as used herein denotes in each case alkyl as defined above, usually comprising 1 to 6 carbon atoms, preferably 1 to 4 carbon atoms, wherein 1 carbon atom carries an haloalkoxy radical as defined above, usually comprising 1 to 10, frequently 1 to 6, in particular 1 to 4, carbon atoms as defined above. Examples are fluoromethoxymethyl, difluoromethoxymethyl, trifluoromethoxymethyl, 1-fluoroethoxymethyl, 2-fluoroethoxymethyl, 1,1-difluoroethoxymethyl, 1,2-difluoroethoxymethyl, 2,2-difluoroethoxymethyl, 1,1,2-trifluoroethoxymethyl, 1,2,2-trifluoroethoxymethyl, 2,2,2-trifluoroethoxymethyl, pentafluoroethoxymethyl, 1-fluoroethoxy-1-ethyl, 2-fluoroethoxy-1-ethyl, 1,1-difluoroethoxy-1-ethyl, 1,2-difluoroethoxy-1-ethyl, 2,2-difluoroethoxy-1-ethyl, 1,1,2-trifluoroethoxy-1-ethyl, 1,2,2-trifluoroethoxy-1-ethyl, 2,2,2-trifluoroethoxy-1-ethyl, pentafluoroethoxy-1-ethyl, 1-fluoroethoxy-2-ethyl, 2-fluoroethoxy-2-ethyl, 1,1-difluoroethoxy-2-ethyl, 1,2-difluoroethoxy-2-ethyl, 2,2-difluoroethoxy-2-ethyl, 1,1,2-trifluoroethoxy-2-ethyl, 1,2,2-trifluoroethoxy-2-ethyl, 2,2,2-trifluoroethoxy-2-ethyl, pentafluoroethoxy-2-ethyl, and the like.

The term "alkylthio" (also alkylsulfanyl or alkyl-S—)" as used herein denotes in each case a straight-chain or branched saturated alkyl group as defined above, usually comprising 1 to 10 carbon atoms ("$C_1$-$C_{10}$-alkylthio"), frequently comprising 1 to 6 carbon atoms ("$C_1$-$C_6$-alkylthio"), preferably 1 to 4 carbon atoms ("$C_1$-$C_4$-alkylthio"), which is attached via a sulfur atom at any position in the alkyl group. $C_1$-$C_2$-Alkylthio is methylthio or ethylthio. $C_1$-$C_4$-Alkylthio is additionally, for example, n-propylthio, 1-methylethylthio(isopropylthio), butylthio, 1-methylpropylthio(sec-butylthio), 2-methylpropylthio(isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "haloalkylthio" as used herein refers to an alkylthio group as defined above wherein the hydrogen atoms are partially or fully substituted by fluorine, chlorine, bromine and/or iodine. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The terms "alkylsulfinyl" and "$S(O)_n$-alkyl" (wherein n is 1) are equivalent and, as used herein, denote an alkyl group, as defined above, attached via a sulfinyl [S(O)] group. For example, the term "$C_1$-$C_2$-alkylsulfinyl" refers to a $C_1$-$C_2$-alkyl group, as defined above, attached via a sulfinyl [S(O)] group. The term "$C_1$-$C_4$-alkylsulfinyl" refers to a $C_1$-$C_4$-alkyl group, as defined above, attached via a sulfinyl [S(O)] group. The term "$C_1$-$C_6$-alkylsulfinyl" refers to a $C_1$-$C_6$-alkyl group, as defined above, attached via a sulfinyl [S(O)] group. $C_1$-$C_2$-alkylsulfinyl is methylsulfinyl or ethylsulfinyl. $C_1$-$C_4$-alkylsulfinyl is additionally, for example, n-propylsulfinyl, 1-methylethylsulfinyl(isopropylsulfinyl), butylsulfinyl, 1-methylpropylsulfinyl(sec-butylsulfinyl), 2-methylpropylsulfinyl(isobutylsulfinyl) or 1,1-dimethylethylsulfinyl(tert-butylsulfinyl). $C_1$-$C_6$-alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The terms "alkylsulfonyl" and "$S(O)_n$-alkyl" (wherein n is 2) are equivalent and, as used herein, denote an alkyl group, as defined above, attached via a sulfonyl [$S(O)_2$] group. The term "$C_1$-$C_2$-alkylsulfonyl" refers to a $C_1$-$C_2$-alkyl group, as defined above, attached via a sulfonyl [$S(O)_2$] group. The term "$C_1$-$C_4$-alkylsulfonyl" refers to a $C_1$-$C_4$-alkyl group, as defined above, attached via a sulfonyl [$S(O)_2$] group. The term "$C_1$-$C_6$-alkylsulfonyl" refers to a $C_1$-$C_6$-alkyl group, as defined above, attached via a sulfonyl [$S(O)_2$] group. $C_1$-$C_2$-alkylsulfonyl is methylsulfonyl or ethylsulfonyl. $C_1$-$C_4$-alkylsulfonyl is additionally, for example, n-propylsulfonyl, 1-methylethylsulfonyl(isopropylsulfonyl), butylsulfonyl, 1-methylpropylsulfonyl(sec-butylsulfonyl), 2-methylpropylsulfonyl(isobutylsulfonyl) or 1,1-dimethylethylsulfonyl(tert-butylsulfonyl). $C_1$-$C_6$-alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "alkylamino" as used herein denotes in each case a group —NHR, wherein R is a straight-chain or branched alkyl group usually having from 1 to 6 carbon atoms ("$C_1$-$C_6$-alkylamino"), preferably 1 to 4 carbon atoms("$C_1$-$C_4$-alkylamino"). Examples of $C_1$-$C_6$-alkylamino are methylamino, ethylamino, n-propylamino, isopropylamino, n-butylamino, 2-butylamino, iso-butylamino, tert-butylamino, and the like.

The term "dialkylamino" as used herein denotes in each case a group-NRR', wherein R and R', independently of each other, are a straight-chain or branched alkyl group each usually having from 1 to 6 carbon atoms ("di-($C_1$-$C_6$-alkyl)-amino"), preferably 1 to 4 carbon atoms ("di-($C_1$-$C_4$-alkyl)-amino"). Examples of a di-($C_1$-$C_6$-alkyl)-amino group are dimethylamino, diethylamino, dipropylamino, dibutylamino, methyl-ethyl-amino, methyl-propyl-amino, methyl-isopropylamino, methyl-butyl-amino, methyl-isobutyl-amino, ethyl-propyl-amino, ethyl-isopropylamino, ethyl-butyl-amino, ethyl-isobutyl-amino, and the like.

The term "alkylaminosulfonyl" as used herein denotes in each case a straight-chain or branched alkylamino group as defined above, which is bound to the remainder of the molecule via a sulfonyl [$S(O)_2$] group. Examples of an alkylaminosulfonyl group are methylaminosulfonyl, ethylaminosulfonyl, n-propylaminosulfonyl, isopropylaminosulfonyl, n-butylaminosulfonyl, 2-butylaminosulfonyl, iso-butylaminosulfonyl, tert-butylaminosulfonyl, and the like.

The term "dialkylaminosulfonyl" as used herein denotes in each case a straight-chain or branched alkylamino group as defined above, which is bound to the remainder of the molecule via a sulfonyl [$S(O)_2$] group. Examples of an dialkylaminosulfonyl group are dimethylaminosulfonyl, diethylaminosulfonyl, dipropylaminosulfonyl, dibutylaminosulfonyl, methyl-ethyl-aminosulfonyl, methyl-propyl-aminosulfonyl, methyl-isopropylaminosulfonyl, methyl-butyl-aminosulfonyl, methyl-isobutyl-aminosulfonyl, ethyl-propyl-aminosulfonyl, ethyl-isopropylaminosulfonyl, ethyl-butyl-aminosulfonyl, ethyl-isobutyl-aminosulfonyl, and the like.

The suffix "-carbonyl" in a group denotes in each case that the group is bound to the remainder of the molecule via a carbonyl C=O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl.

The term "het(ero)aryl" as used herein refers to a mono-, bi- or tricyclic heteroaromatic hydrocarbon radical, preferably to a monocyclic heteroaromatic radical, such as pyridyl, pyrimidyl and the like.

The term "3-, 4-, 5-, 6- or 7-membered saturated, partially unsaturated or fully unsaturated heterocyclic ring containing 1, 2 or 3 heteroatoms or heteroatom groups selected from N, O, S, NO, SO and $SO_2$, as ring members" [wherein "fully unsaturated" also includes "aromatic"] as used herein denotes monocyclic radicals, the monocyclic radicals being saturated, partially unsaturated or fully unsaturated (including aromatic). Unsaturated rings contain at least one C—C and/or C—N and/or N—N double bond(s). Fully unsaturated rings contain as many conjugated C—C and/or C—N and/or N—N double bonds as allowed by the ring size. Fully unsaturated 5- or 6-membered heterocyclic rings are aromatic. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5-, 6- or 7-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl. A 3-, 4-, 5-, 6- or 7-membered fully unsaturated (including aromatic) heterocyclic ring is e.g. a 5- or 6-membered fully unsaturated (including aromatic) heterocyclic ring. Examples are: 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl,3-pyridazinyl, 4-pyridazinyl, 2-pyrimidinyl, 4-pyrimidinyl, 5-pyrimidinyl and 2-pyrazinyl.

When $R^5$ and $R^6$ together with the sulfur atom to which they are attached form a saturated, partially unsaturated or fully unsaturated 3-, 4-, 5-, 6-, 7-, 8-, 9- or 10-membered ring which optionally contains 1, 2, 3 or 4 further heteroatoms or heteroatom groups selected from N, O, S, NO, SO and $SO_2$, as ring members, this is an S-bound heterocyclic ring which apart the sulfur ring atom may additionally contain 1, 2, 3 or 4 further heteroatoms or heteroatom groups selected from N, O, S, NO, SO and $SO_2$, as ring members. Examples are thiiran-1-yl, thietan-1-yl, tetrahydrothien-1-yl, 1,3-dithiolan-1-yl, thian-1-yl, thiazolidin-1-yl, isothiazolidin-1-yl, thiadiazolidin-1-yl, thiomorpholin-1-yl, 2,3-dihydrothien-1-yl, 2,4-dihydrothien-1-yl, and the like.

When $R^c$ and $R^d$, together with the nitrogen atom to which they are bound form a 3-, 4-, 5-, 6- or 7-membered saturated, partially unsaturated or fully unsaturated heterocyclic ring which may additionally contain 1 or 2 further heteroatoms or heteroatom groups selected from N, O, S, NO, SO and $SO_2$, as ring members, this is an N-bound heterocyclic ring which apart the nitrogen ring atom may additionally contain 1, 2, 3 or 4 further heteroatoms or heteroatom groups selected from N, O, S, NO, SO and $SO_2$, as ring members. Examples are aziridin-1-yl, azetidin-1-yl, pyrrolidine-1-yl, pyrazolidin-1-yl, imidazolin-1-yl, oxazolidin-3-yl, isoxazolidin-3-yl, thiazolidin-1-yl, isothiazolidin-1-yl, triazolidin-1-yl, piperdon-1-yl, piperazine-1-yl, morpholin-4-yl, thiomorpholin-1-yl, 1,1-dioxothiomorpholin-4-yl, pyrrolin-1-yl, pyrrolin-1-yl, imidazolin-1-yl, dihydropyridin-1-yl, tetrahydropyridin-1-yl, pyrrol-1-yl, pyrazo-1-yl, imidazol-1-yl and the like.

The remarks made below as to preferred embodiments of the variables (substituents) of the compounds of formulae (I) and (I-a) are valid on their own as well as preferably in combination with each other, as well as in combination with the stereoisomers, salts, tautomers or N-oxides thereof.

The remarks made below concerning preferred embodiments of the variables further are valid on their own as well as preferably in combination with each other concerning the compounds of formulae (I) or (I-a), where applicable, as well as concerning the uses and methods according to the invention and the composition according to the invention.

Preferred compounds according to the invention are compounds of formulae (I) or (I-a) or a stereoisomer, salt, tautomer or N-oxide thereof, wherein the salt is an agriculturally or veterinarily acceptable salt. Further preferred compounds according to the invention are compounds of formulae (I) or (I-a) or a stereoisomer or salt thereof, especially an agriculturally or veterinarily acceptable salt. Particularly preferred compounds according to the invention are compounds of formulae (I) or (I-a) or a salt thereof, especially an agriculturally or veterinarily acceptable salt thereof.

Preferred are compounds of formula (I), wherein $R^1$ is selected from halogen and fluoromethyl, in particular from F, Cl, Br, $CF_3$ and $CHF_2$, specifically from Cl, Br and $CF_3$ and more specifically from Cl and Br.

Preferred are compounds of formula (I), wherein $R^2$ is selected from F, Cl, Br, I, $CF_3$ and CN, in particular from F, Cl, Br, $CF_3$ and CN, specifically from F, Cl, Br and CN, more specifically from Cl, Br and CN and most specifically from Cl and Br.

Preferred are compounds of formula (I), wherein $R^3$ is selected from hydrogen, $C_1$-$C_4$ alkyl, $C_1$-$C_4$ haloalkyl, $C_2$-$C_6$-alkenyl, $C_2$-$C_6$-haloalkenyl, $C_3$-$C_6$-cycloalkyl, $C_3$-$C_6$-halocycloalkyl, $C_1$-$C_2$-alkoxy-$C_1$-$C_2$-alkyl, $C_1$-$C_2$-haloalkoxy-$C_1$-$C_2$-alkyl, $C(=O)R^a$, $C(=O)OR^b$ and $C(=O)NR^cR^d$.

In particular, $R^3$ is selected from hydrogen, $C_1$-$C_2$-alkyl and $C_1$-$C_2$ haloalkyl, specifically from hydrogen, methyl and halomethyl, and more specifically is hydrogen.

Preferred are compounds of formula (I), wherein $R^4$ is selected from F, Cl and Br, specifically from Cl and Br and more specifically from Cl.

Preferred are compounds of formula (I), wherein $R^5$ and $R^6$ are independently selected from $C_1$-$C_6$-alkyl, $C_3$-$C_6$-cycloalkyl, $C_2$-$C_6$-alkenyl, $C_2$-$C_6$-alkynyl, wherein the aforementioned radicals may be substituted with 1 to 10 substituents $R^e$, and phenyl, which is unsubstituted or carries 1 to 4 radicals $R^f$, or $R^5$ and $R^6$ together represent a $C_3$-$C_7$-alkylene chain forming together with the sulfur atom to which they are attached a 4-, 5-, 6-, 7- or 8-membered saturated ring, wherein 1 or 2 of the $CH_2$ groups in the $C_3$-$C_7$-alkylene chain may be replaced by 1 or 2 groups independently selected from the group consisting of C=O, C=S, O, S, N, NO, SO, $SO_2$ and NH, and wherein the carbon and/or nitrogen atoms in the $C_3$-$C_7$-alkylene chain may be substituted with 1 to 5 substituents independently selected from the group consisting of halogen, cyano, $C_1$-$C_2$-alkyl, $C_1$-$C_2$-haloalkyl, said substituents being identical or different from one another if more than one substituent is present.

In particular, $R^5$ and $R^6$ are independently selected from $C_1$-$C_6$-alkyl, $C_3$-$C_6$-cycloalkyl, $C_2$-$C_6$-alkenyl, $C_2$-$C_6$-alkynyl, wherein the aforementioned radicals may be substituted with 1 to 4 substituents selected from halogen, cyano, $C_1$-$C_6$-alkyl and $C_3$-$C_6$-cycloalkyl, and phenyl, which is unsubstituted or carries 1, 2 or 3 radical selected from halogen, cyano, methyl, methoxy, trifluoromethyl and difluoromethyl, or $R^5$ together with $R^6$ form a bivalent moiety $(CH_2)_m$ where m is from 3 to 7 and wherein one $CH_2$ moiety may be replaced by S, SO or $SO_2$.

Especially, $R^5$ and $R^6$ are independently selected from $C_1$-$C_6$-alkyl, $C_3$-$C_6$-cycloalkyl, $C_2$-$C_6$-alkenyl, wherein the aforementioned radicals may be substituted with 1 or 2 substituents selected from F, Cl, Br, cyano, $C_1$-$C_4$-alkyl and $C_3$-$C_6$-cycloalkyl, and phenyl, which is unsubstituted or carries 1 or 2 radical selected from Cl, Br, cyano, methyl, methoxy, trifluoromethyl and difluoromethyl, or $R^5$ together with $R^6$ form a bivalent moiety $(CH_2)_m$ where m is from 3 to 6 and wherein one $CH_2$ moiety may be replaced by S, SO or $SO_2$.

Specifically, $R^5$ and $R^6$ are independently selected from the group consisting of $CH_3$, $CH_2CH_3$, $CH=CH_2$, $CH_2CH_2CH_3$, $CH(CH_3)_2$, $CH_2CH_2CH_2CH_3$, $C(CH_3)_3$, $CH_2CH(CH_3)_2$, $CH(CH_3)CH_2CH_3$, $CH_2CH_2CH_2CH_2CH_3$, $CH_2CH_2CH_2CH_2CH_2CH_3$, $CH_2CH_2CH(CH_3)_2$, $CH(CH_3)CH(CH_3)_2$, $CH_2CH_2OH$, $CH_2CH=CH_2$, $CH_2C\equiv CH$, $CH(CH_3)CH=CH_2$, $CHF_2$, $CH_2Cl$, $CH_2CH_2CN$, $CH_2CH_2Cl$, cyclopropyl, cyclobutyl, cyclopentyl, cyclohexyl, cyclopropylmethyl, 1-cyclopropylethyl, 2-cyclopropylethyl, cyclobutylmethyl, cyclopentylmethyl, cyclohexylmethyl and phenyl, or $R^5$ together with $R^6$ form a bivalent moiety selected from $(CH_2)_4$ and $CH_2SCH_2CH_2$, and more specifically from the group consisting of $CH_3$, $CH_2CH_3$, $CH=CH_2$, $CH_2CH_2CH_3$, $CH(CH_3)_2$, $CH_2CH_2CH_2CH_3$, $C(CH_3)_3$, $CH_2CH(CH_3)_2$, $CH(CH_3)CH_2CH_3$, $CH_2CH=CH_2$, $CH_2C\equiv CH$, $CH(CH_3)CH=CH_2$, $CHF_2$, $CH_2Cl$, $CH_2CH_2CN$, $CH_2CH_2Cl$, cyclopropyl, cyclobutyl, cyclopentyl, cyclohexyl, cyclopropylmethyl, 1-cyclopropylethyl, cyclopentylmethyl, cyclohexylmethyl and phenyl, or $R^5$ together with $R^6$ form a bivalent moiety selected from $(CH_2)_4$ and $CH_2SCH_2CH_2$.

Preferred are compounds of formula (I), wherein k is 0.

In this context, the variables $R^a$, $R^b$, $R^c$, $R^d$, $R^e$, $R^f$ and n, independently of each other, preferably have one of the following meanings:

$R^a$ is selected from $C_1$-$C_6$-alkyl, $C_2$-$C_6$-alkenyl, $C_3$-$C_8$-cycloalkyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 substituents selected from $C_1$-$C_4$ alkoxy; phenyl, benzyl and pyridyl, wherein the last three radicals may be unsubstituted, partially or fully halogenated and/or carry 1 or 2 substituents selected from $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl, $C_1$-$C_4$-alkylamino and di-($C_1$-$C_4$-alkyl) amino.

More preferably $R^a$ is selected from $C_1$-$C_4$-alkyl, $C_2$-$C_4$-alkenyl, wherein the aforementioned radicals may be unsubstituted, partially or fully halogenated and/or may carry 1 or 2 substituents selected from $C_1$-$C_2$ alkoxy; phenyl and benzyl, wherein the last two radicals may be unsubstituted, partially or fully halogenated and/or carry 1 or 2 substituents selected from $C_1$-$C_2$-alkyl, $C_1$-$C_2$-haloalkyl, $C_1$-$C_2$-alkoxy and $C_1$-$C_2$-haloalkoxy; and in particular selected from $C_1$-$C_4$-alkyl, $C_1$-$C_4$-haloalkyl and benzyl which may be unsubstituted, partially or fully halogenated and/or carry 1 or 2 substituents selected from methyl, halomethyl, methoxy and halomethoxy.

$R^b$ is selected from $C_1$-$C_6$-alkyl, $C_2$-$C_6$-alkenyl, $C_3$-$C_8$-cycloalkyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 substituents selected from $C_1$-$C_4$-alkoxy; phenyl, benzyl and pyridyl, wherein the last three radicals may be unsubstituted, partially or fully halogenated and/or carry 1 or 2 substituents selected from $C_1$-$C_4$-alkyl, $C_1$-$C_4$-haloalkyl, $C_1$-$C_4$-alkoxy, $C_1$-$C_4$-haloalkoxy and ($C_1$-$C_4$-alkoxy)carbonyl.

More preferably $R^b$ is selected from $C_1$-$C_4$-alkyl, $C_2$-$C_4$-alkenyl, wherein the aforementioned radicals may be unsubstituted, partially or fully halogenated and/or may carry 1 or 2 substituents selected from $C_1$-$C_2$-alkoxy; phenyl and benzyl, wherein the last two radicals may be unsubstituted, partially or fully halogenated and/or carry 1 or 2 substituents selected from $C_1$-$C_2$-alkyl, $C_1$-$C_2$-haloalkyl, $C_1$-$C_2$-alkoxy and $C_1$-$C_2$-haloalkoxy, and in particular selected from $C_1$-$C_4$-alkyl, $C_1$-$C_4$-haloalkyl and benzyl which may be unsubstituted, partially or fully halogenated and/or carry 1 or 2 substituents selected from methyl, halomethyl, methoxy and halomethoxy.

$R^c$, $R^d$ are, independently from one another and independently of each occurrence, selected from hydrogen, $C_1$-$C_6$-alkyl, $C_2$-$C_6$-alkenyl, $C_3$-$C_8$-cycloalkyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 radicals selected from $C_1$-$C_4$-alkoxy; $C_1$-$C_4$-alkylsulfonyl, phenyl and benzyl, wherein the two last mentioned radicals may be unsubstituted, partially or fully halogenated and/or carry 1 or 2 substituents selected from $C_1$-$C_4$-alkyl, $C_1$-$C_4$-haloalkyl, $C_1$-$C_4$-alkoxy and $C_1$-$C_4$ haloalkoxy; or $R^c$ and $R^d$, together with the nitrogen atom to which they are bound, may form a 5-, 6- or 7-membered saturated, partially unsaturated or fully unsaturated heterocyclic ring which may additionally contain 1 or 2 further heteroatoms or heteroatom groups selected from N, O and S, as ring members, where the heterocyclic ring may optionally be substituted with halogen, $C_1$-$C_2$-haloalkyl, $C_1$-$C_2$-alkoxy or $C_1$-$C_2$-haloalkoxy.

More preferably $R^c$, $R^d$ are, independently from one another and independently of each occurrence, selected from hydrogen, $C_1$-$C_4$-alkyl, $C_1$-$C_4$-haloalkyl and benzyl, or $R^c$ and $R^d$, together with the nitrogen atom to which they are bound, may form a 5- or 6-membered saturated or partly unsaturated heterocyclic ring. In particular, $R^c$, $R^d$ are, independently from one another and independently of each occurrence, hydrogen, $C_1$-$C_3$-alkyl, $C_1$-$C_2$-haloalkyl, benzyl, or together with the nitrogen atom to which they are bound form a pyrrolidine or a piperidine ring.

$R^e$ is selected from halogen, cyano, nitro, —OH, $C_2$-$C_4$-alkenyl, $C_3$-$C_8$-cycloalkyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 radicals selected from $C_1$-$C_4$-alkoxy; $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, —$NR^cR^d$, —C(=O)$R^a$, —C(=O)O$R^b$, phenyl, benzyl and phenoxy, wherein the last three radicals may be unsubstituted, partially or fully halogenated and/or carry 1 or 2 substituents selected from $C_1$-$C_4$-alkyl, $C_1$-$C_4$-alkoxy and $C_1$-$C_4$-haloalkoxy.

More preferably $R^e$ is selected from F, Cl, Br, cyano, nitro, —OH, $C_2$-$C_4$-alkenyl, $C_3$-$C_8$-cycloalkyl, wherein the aliphatic and cycloaliphatic moieties of the aforementioned radicals may be unsubstituted, partially or fully halogenated and/or may carry 1 or 2 radicals selected from $C_1$-$C_2$-alkoxy; $C_1$-$C_4$-alkoxy, $C_1$-$C_4$-haloalkoxy, —$NR^cR^d$, —C(=O)$R^a$, phenyl and benzyl, wherein the last two radicals may be unsubstituted, partially or fully halogenated and/or carry 1 or 2 substituents selected from $C_1$-$C_2$-alkyl, $C_1$-$C_2$-haloalkyl, $C_1$-$C_2$-alkoxy and $C_1$-$C_2$-haloalkoxy; and in particular from F, Cl, —OH, $C_1$-$C_4$-alkyl, $C_1$-$C_4$-haloalkyl, $C_1$-$C_4$-alkoxy, $C_1$-$C_4$-haloalkoxy, phenyl and benzyl, wherein the last two radicals may carry 1 or 2 substituents selected F, Cl, methyl, halomethyl, methoxy and halomethoxy.

$R^f$ is selected from halogen, cyano, nitro, —OH, $C_1$-$C_6$-alkyl, $C_2$-$C_6$-alkenyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 radicals selected from $C_1$-$C_2$ alkoxy; $C_1$-$C_4$-alkoxy, $C_1$-$C_4$-haloalkoxy, —$OR^a$, —$NR^cR^d$, —$S(O)_nR^a$, —$C(=O)R^a$ and —$C(=O)OR^b$.

More preferably $R^f$ is selected from F, Cl, Br, nitro, —OH, $C_2$-$C_4$-alkenyl, wherein the aliphatic moieties of the aforementioned radicals may be unsubstituted, partially or fully halogenated and/or may carry 1 or 2 radicals selected from $C_1$-$C_2$ alkoxy; $C_1$-$C_4$-alkoxy, $C_1$-$C_4$-haloalkoxy, —$OR^a$, —$NR^cR^d$ and $C(=O)R^a$; and in particular from F, Cl, nitro, $C_1$-$C_4$-haloalkyl, $C_1$-$C_2$-alkoxy and $C_1$-$C_2$-haloalkoxy.

n is 1 or 2, wherein, in the case of several occurrences, n may be identical or different. More preferably n is 2.

In a preferred embodiment, the compound of formula (I) is of the general formula (I-a)

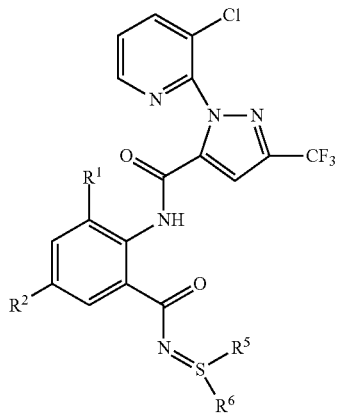

(I-a)

wherein $R^1$, $R^2$, $R^5$ and $R^6$ have one of the general meanings, or, in particular, one of the preferred meanings given above.

Particularly preferred are compounds of formula (I-a), wherein
  $R^1$ is selected from halogen and fluoromethyl, in particular from F, Cl, Br, $CF_3$ and $CHF_2$, specifically from Cl, Br and $CF_3$ and more specifically from Cl and Br;
  $R^2$ is selected from F, Cl, Br, I, $CF_3$ and CN, in particular from F, Cl, Br, $CF_3$ and CN, specifically from Cl, Br, $CF_3$ and CN, more specifically from Cl, Br and CN and most specifically from Cl and Br;
  $R^5$ and $R^6$ are independently selected from $C_1$-$C_6$-alkyl, $C_3$-$C_6$-cycloalkyl, $C_2$-$C_6$-alkenyl, $C_2$-$C_6$-alkynyl, wherein the aforementioned radicals may be substituted with 1 to 10 substituents $R^e$, and phenyl, which is unsubstituted or carries 1 to 4 radicals $R^f$, or $R^5$ and $R^6$ together represent a $C_3$-$C_7$-alkylene chain forming together with the sulfur atom to which they are attached a 4-, 5-, 6-, 7- or 8-membered saturated ring, wherein 1 or 2 of the $CH_2$ groups in the $C_3$-$C_7$-alkylene chain may be replaced by 1 or 2 groups independently selected from the group consisting of C=O, C=S, O, S, N, NO, SO, $SO_2$ and NH, and wherein the carbon and/or nitrogen atoms in the $C_3$-$C_7$-alkylene chain may be substituted with 1 to 5 substituents independently selected from the group consisting of halogen, cyano, $C_1$-$C_2$-alkyl, $C_1$-$C_2$-haloalkyl, said substituents being identical or different from one another if more than one substituent is present.

Especially preferred are compounds of formula (I-a), wherein
  $R^1$ is selected from F, Cl, Br, $CF_3$ and $CHF_2$, specifically from Cl, Br and $CF_3$ and more specifically from Cl and Br;
  $R^2$ is selected from F, Cl, Br, I, $CF_3$ and CN, in particular from F, Cl, Br, $CF_3$ and CN, specifically from Cl, Br, $CF_3$ and CN, more specifically from Cl, Br and CN and most specifically from Cl and Br;
  $R^5$ and $R^6$ are independently selected from $C_1$-$C_6$-alkyl, $C_3$-$C_6$-cycloalkyl, $C_2$-$C_6$-alkenyl, $C_2$-$C_6$-alkynyl, wherein the aforementioned radicals may be substituted with 1 to 4 substituents selected from halogen, OH, cyano, $C_1$-$C_6$-alkyl and $C_3$-$C_6$-cycloalkyl, and phenyl, which is unsubstituted or carries 1, 2 or 3 radical selected from halogen, cyano, methyl, methoxy, trifluoromethyl and difluoromethyl, or $R^5$ together with $R^6$ form a bivalent moiety $(CH_2)_m$ where m is from 3 to 7 and wherein one $CH_2$ moiety may be replaced by S, SO or $SO_2$.

Specifically preferred are compounds of formula (I-a), wherein
  $R^1$ is selected from Cl, Br and $CF_3$ and more specifically from Cl and Br;
  $R^2$ is selected from Cl, Br, $CF_3$ and CN, in particular from Cl, Br and CN and more specifically from Cl and Br;
  $R^5$ and $R^6$ are independently selected from $C_1$-$C_6$-alkyl, $C_3$-$C_6$-cycloalkyl, $C_2$-$C_6$-alkenyl, wherein the aforementioned radicals may be substituted with 1 or 2 substituents selected from OH, F, Cl, Br, cyano, $C_1$-$C_4$-alkyl and $C_3$-$C_6$-cycloalkyl, and phenyl, which is unsubstituted or carries 1 or 2 radical selected from Cl, Br, cyano, methyl, methoxy, trifluoromethyl and difluoromethyl, or $R^5$ together with $R^6$ form a bivalent moiety $(CH_2)_m$ where m is from 3 to 6 and wherein one $CH_2$ moiety may be replaced by S, SO or $SO_2$.

More specifically preferred are compounds of formula (I-a), wherein
  $R^1$ is selected from Cl and Br;
  $R^2$ is selected from Cl and Br;
  $R^5$ and $R^6$ are independently selected from the group consisting of $CH_3$, $CH_2CH_3$, CH=$CH_2$, $CH_2CH_2CH_3$, $CH(CH_3)_2$, $CH_2CH_2CH_2CH_3$, $C(CH_3)_3$, $CH_2CH(CH_3)_2$, $CH(CH_3)CH_2CH_3$, $CH_2CH_2CH_2CH_2CH_3$, $CH_2CH_2CH_2CH_2CH_2CH_3$, $CH_2CH_2CH(CH_3)_2$, $CH(CH_3)CH(CH_3)_2$, $CH_2CH_2OH$, $CH_2CH$=$CH_2$, $CH_2C$≡$CH$, $CH(CH_3)CH$=$CH_2$, $CHF_2$, $CH_2Cl$, $CH_2CH_2CN$, $CH_2CH_2Cl$, cyclopropyl, cyclobutyl, cyclopentyl, cyclohexyl, cyclopropylmethyl, 1-cyclopropylethyl, 2-cyclopropylethyl, cyclobutylmethyl, cyclopentylmethyl, cyclohexylmethyl and phenyl, or $R^5$ together with $R^6$ form a bivalent moiety selected from $(CH_2)_4$ and $CH_2SCH_2CH_2$, and especially from $CH_3$, $CH_2CH_3$, CH=$CH_2$, $CH_2CH_2CH_3$, $CH(CH_3)_2$, $CH_2CH_2CH_2CH_3$, $C(CH_3)_3$, $CH_2CH(CH_3)_2$, $CH(CH_3)CH_2CH_3$, $CH_2CH$=$CH_2$, $CH_2C$≡$CH$, $CH(CH_3)CH$=$CH_2$, $CHF_2$, $CH_2Cl$, $CH_2CH_2CN$, $CH_2CH_2Cl$, cyclopropyl, cyclobutyl, cyclopentyl, cyclohexyl, cyclopropylmethyl, 1-cyclopropylethyl, cyclopentylmethyl, cyclohexylmethyl and phenyl, or $R^5$ together with $R^6$ form a bivalent moiety selected from $(CH_2)_4$ and $CH_2SCH_2CH_2$.

Examples of preferred compounds are the individual compounds compiled in the tables 1 to 22 below, Moreover, the meanings mentioned below for the individual variables in the tables are per se, independently of the combination in which they are mentioned, a particularly preferred embodiment of the substituents in question.

Table 1 Compounds of the formula (I-a) in which $R^1$ is F, $R^2$ is Cl and the combination of $R^5$ and $R^6$ for a compound corresponds in each case to one row of Table A;

Table 2 Compounds of the formula (I-a) in which $R^1$ is Cl, $R^2$ is Cl and the combination of $R^5$ and $R^6$ for a compound corresponds in each case to one row of Table A;

Table 3 Compounds of the formula (I-a) in which $R^1$ is Br, $R^2$ is Cl and the combination of $R^5$ and $R^6$ for a compound corresponds in each case to one row of Table A;

Table 4 Compounds of the formula (I-a) in which $R^1$ is $CF_3$, $R^2$ is Cl and the combination of $R^5$ and $R^6$ for a compound corresponds in each case to one row of Table A;

Table 5 Compounds of the formula (I-a) in which $R^1$ is $CHF_2$, $R^2$ is Cl and the combination of $R^5$ and $R^6$ for a compound corresponds in each case to one row of Table A;

Table 6 Compounds of the formula (I-a) in which $R^1$ is F, $R^2$ is F and the combination of $R^5$ and $R^6$ for a compound corresponds in each case to one row of Table A;

Table 7 Compounds of the formula (I-a) in which $R^1$ is Cl, $R^2$ is F and the combination of $R^5$ and $R^6$ for a compound corresponds in each case to one row of Table A;

Table 8 Compounds of the formula (I-a) in which $R^1$ is Br, $R^2$ is F and the combination of $R^5$ and $R^6$ for a compound corresponds in each case to one row of Table A;

Table 9 Compounds of the formula (I-a) in which $R^1$ is $CF_3$, $R^2$ is F and the combination of $R^5$ and $R^6$ for a compound corresponds in each case to one row of Table A;

Table 10 Compounds of the formula (I-a) in which $R^1$ is $CHF_2$, $R^2$ is F and the combination of $R^5$ and $R^6$ for a compound corresponds in each case to one row of Table A;

Table 11 Compounds of the formula (I-a) in which $R^1$ is F, $R^2$ is Br and the combination of $R^5$ and $R^6$ for a compound corresponds in each case to one row of Table A;

Table 12 Compounds of the formula (I-a) in which $R^1$ is Cl, $R^2$ is Br and the combination of $R^5$ and $R^6$ for a compound corresponds in each case to one row of Table A;

Table 13 Compounds of the formula (I-a) in which $R^1$ is Br, $R^2$ is Br and the combination of $R^5$ and $R^6$ for a compound corresponds in each case to one row of Table A;

Table 14 Compounds of the formula (I-a) in which $R^1$ is $CF_3$, $R^2$ is Br and the combination of $R^5$ and $R^6$ for a compound corresponds in each case to one row of Table A;

Table 15 Compounds of the formula (I-a) in which $R^1$ is $CHF_2$, $R^2$ is Br and the combination of $R^5$ and $R^6$ for a compound corresponds in each case to one row of Table A;

Table 16 Compounds of the formula (I-a) in which $R^1$ is F, $R^2$ is CN and the combination of $R^5$ and $R^6$ for a compound corresponds in each case to one row of Table A;

Table 17 Compounds of the formula (I-a) in which $R^1$ is Cl, $R^2$ is CN and the combination of $R^5$ and $R^6$ for a compound corresponds in each case to one row of Table A;

Table 18 Compounds of the formula (I-a) in which $R^1$ is Br, $R^2$ is CN and the combination of $R^5$ and $R^6$ for a compound corresponds in each case to one row of Table A;

Table 19 Compounds of the formula (I-a) in which $R^1$ is $CF_3$, $R^2$ is CN and the combination of $R^5$ and $R^6$ for a compound corresponds in each case to one row of Table A;

Table 20 Compounds of the formula (I-a) in which $R^1$ is $CHF_2$, $R^2$ is CN and the combination of $R^5$ and $R^6$ for a compound corresponds in each case to one row of Table A;

Table 21 Compounds of the formula (I-a) in which $R^1$ is Cl, $R^2$ is $CF_3$ and the combination of $R^5$ and $R^6$ for a compound corresponds in each case to one row of Table A;

Table 22 Compounds of the formula (I-a) in which $R^1$ is Br, $R^2$ is $CF_3$ and the combination of $R^5$ and $R^6$ for a compound corresponds in each case to one row of Table A;

TABLE A

| | $R^5$ | $R^6$ |
|---|---|---|
| A-1 | $CH_3$ | $CH_3$ |
| A-2 | $C_2H_5$ | $CH_3$ |
| A-3 | $CH=CH_2$ | $CH_3$ |
| A-4 | $CH_2CH_2CH_3$ | $CH_3$ |
| A-5 | $CH(CH_3)_2$ | $CH_3$ |
| A-6 | $CH_2CH_2CH_2CH_3$ | $CH_3$ |
| A-7 | $C(CH_3)_3$ | $CH_3$ |
| A-8 | $CH_2CH(CH_3)_2$ | $CH_3$ |
| A-9 | $CH(CH_3)CH_2CH_3$ | $CH_3$ |
| A-10 | $CH_2CH=CH_2$ | $CH_3$ |
| A-11 | $CH_2C\equiv CH$ | $CH_3$ |
| A-12 | $CH(CH_3)CH=CH_2$ | $CH_3$ |
| A-13 | $CHF_2$ | $CH_3$ |
| A-14 | $CH_2Cl$ | $CH_3$ |
| A-15 | $CH_2CH_2CN$ | $CH_3$ |
| A-16 | $CH_2CH_2Cl$ | $CH_3$ |
| A-17 | $c-C_3H_5$ | $CH_3$ |
| A-18 | $c-C_4H_7$ | $CH_3$ |
| A-19 | $c-C_5H_9$ | $CH_3$ |
| A-20 | $c-C_6H_{11}$ | $CH_3$ |
| A-21 | $CH_2-c-C_3H_5$ | $CH_3$ |
| A-22 | $CH(CH_3)-c-C_3H_5$ | $CH_3$ |
| A-23 | $CH_2-c-C_5H_9$ | $CH_3$ |
| A-24 | $CH_2-c-C_6H_{11}$ | $CH_3$ |
| A-25 | $C_6H_5$ | $CH_3$ |
| A-26 | $CH_3$ | $C_2H_5$ |
| A-27 | $C_2H_5$ | $C_2H_5$ |
| A-28 | $CH=CH_2$ | $C_2H_5$ |
| A-29 | $CH_2CH_2CH_3$ | $C_2H_5$ |
| A-30 | $CH(CH_3)_2$ | $C_2H_5$ |
| A-31 | $CH_2CH_2CH_2CH_3$ | $C_2H_5$ |
| A-32 | $C(CH_3)_3$ | $C_2H_5$ |
| A-33 | $CH_2CH(CH_3)_2$ | $C_2H_5$ |
| A-34 | $CH(CH_3)CH_2CH_3$ | $C_2H_5$ |
| A-35 | $CH_2CH=CH_2$ | $C_2H_5$ |
| A-36 | $CH_2C\equiv CH$ | $C_2H_5$ |
| A-37 | $CH(CH_3)CH=CH_2$ | $C_2H_5$ |
| A-38 | $CHF_2$ | $C_2H_5$ |
| A-39 | $CH_2Cl$ | $C_2H_5$ |
| A-40 | $CH_2CH_2CN$ | $C_2H_5$ |
| A-41 | $CH_2CH_2Cl$ | $C_2H_5$ |
| A-42 | $c-C_3H_5$ | $C_2H_5$ |
| A-43 | $c-C_4H_7$ | $C_2H_5$ |
| A-44 | $c-C_5H_9$ | $C_2H_5$ |
| A-45 | $c-C_6H_{11}$ | $C_2H_5$ |
| A-46 | $CH_2-c-C_3H_5$ | $C_2H_5$ |
| A-47 | $CH(CH_3)-c-C_3H_5$ | $C_2H_5$ |
| A-48 | $CH_2-c-C_5H_9$ | $C_2H_5$ |
| A-49 | $CH_2-c-C_6H_{11}$ | $C_2H_5$ |
| A-50 | $C_6H_5$ | $C_2H_5$ |
| A-51 | $CH_3$ | $CH=CH_2$ |
| A-52 | $C_2H_5$ | $CH=CH_2$ |
| A-53 | $CH=CH_2$ | $CH=CH_2$ |
| A-54 | $CH_2CH_2CH_3$ | $CH=CH_2$ |
| A-55 | $CH(CH_3)_2$ | $CH=CH_2$ |
| A-56 | $CH_2CH_2CH_2CH_3$ | $CH=CH_2$ |
| A-57 | $C(CH_3)_3$ | $CH=CH_2$ |
| A-58 | $CH_2CH(CH_3)_2$ | $CH=CH_2$ |
| A-59 | $CH(CH_3)CH_2CH_3$ | $CH=CH_2$ |
| A-60 | $CH_2CH=CH_2$ | $CH=CH_2$ |
| A-61 | $CH_2C\equiv CH$ | $CH=CH_2$ |
| A-62 | $CH(CH_3)CH=CH_2$ | $CH=CH_2$ |
| A-63 | $CHF_2$ | $CH=CH_2$ |
| A-64 | $CH_2Cl$ | $CH=CH_2$ |
| A-65 | $CH_2CH_2CN$ | $CH=CH_2$ |

TABLE A-continued

|       | R⁵                                    | R⁶                                              |
|-------|---------------------------------------|-------------------------------------------------|
| A-66  | CH₂CH₂Cl                              | CH=CH₂                                          |
| A-67  | c-C₃H₅                                | CH=CH₂                                          |
| A-68  | c-C₄H₇                                | CH=CH₂                                          |
| A-69  | c-C₅H₉                                | CH=CH₂                                          |
| A-70  | c-C₆H₁₁                               | CH=CH₂                                          |
| A-71  | CH₂-c-C₃H₅                            | CH=CH₂                                          |
| A-72  | CH(CH₃)-c-C₃H₅                        | CH=CH₂                                          |
| A-73  | CH₂-c-C₅H₉                            | CH=CH₂                                          |
| A-74  | CH₂-c-C₆H₁₁                           | CH=CH₂                                          |
| A-75  | C₆H₅                                  | CH=CH₂                                          |
| A-76  | CH₃                                   | CH₂CH₂CH₃                                       |
| A-77  | C₂H₅                                  | CH₂CH₂CH₃                                       |
| A-78  | CH=CH₂                                | CH₂CH₂CH₃                                       |
| A-79  | CH₂CH₂CH₃                             | CH₂CH₂CH₃                                       |
| A-80  | CH(CH₃)₂                              | CH₂CH₂CH₃                                       |
| A-81  | CH₂CH₂CH₂CH₃                          | CH₂CH₂CH₃                                       |
| A-82  | C(CH₃)₃                               | CH₂CH₂CH₃                                       |
| A-83  | CH₂CH(CH₃)₂                           | CH₂CH₂CH₃                                       |
| A-84  | CH(CH₃)CH₂CH₃                         | CH₂CH₂CH₃                                       |
| A-85  | CH₂CH=CH₂                             | CH₂CH₂CH₃                                       |
| A-86  | CH₂C≡CH                               | CH₂CH₂CH₃                                       |
| A-87  | CH(CH₃)CH=CH₂                         | CH₂CH₂CH₃                                       |
| A-88  | CHF₂                                  | CH₂CH₂CH₃                                       |
| A-89  | CH₂Cl                                 | CH₂CH₂CH₃                                       |
| A-90  | CH₂CH₂CN                              | CH₂CH₂CH₃                                       |
| A-91  | CH₂CH₂Cl                              | CH₂CH₂CH₃                                       |
| A-92  | c-C₃H₅                                | CH₂CH₂CH₃                                       |
| A-93  | c-C₄H₇                                | CH₂CH₂CH₃                                       |
| A-94  | c-C₅H₉                                | CH₂CH₂CH₃                                       |
| A-95  | c-C₆H₁₁                               | CH₂CH₂CH₃                                       |
| A-96  | CH₂-c-C₃H₅                            | CH₂CH₂CH₃                                       |
| A-97  | CH(CH₃)-c-C₃H₅                        | CH₂CH₂CH₃                                       |
| A-98  | CH₂-c-C₅H₉                            | CH₂CH₂CH₃                                       |
| A-99  | CH₂-c-C₆H₁₁                           | CH₂CH₂CH₃                                       |
| A-100 | C₆H₅                                  | CH₂CH₂CH₃                                       |
| A-101 | CH₃                                   | CH(CH₃)₂                                        |
| A-102 | C₂H₅                                  | CH(CH₃)₂                                        |
| A-103 | CH=CH₂                                | CH(CH₃)₂                                        |
| A-104 | CH₂CH₂CH₃                             | CH(CH₃)₂                                        |
| A-105 | CH(CH₃)₂                              | CH(CH₃)₂                                        |
| A-106 | CH₂CH₂CH₂CH₃                          | CH(CH₃)₂                                        |
| A-107 | C(CH₃)₃                               | CH(CH₃)₂                                        |
| A-108 | CH₂CH(CH₃)₂                           | CH(CH₃)₂                                        |
| A-109 | CH(CH₃)CH₂CH₃                         | CH(CH₃)₂                                        |
| A-110 | CH₂CH=CH₂                             | CH(CH₃)₂                                        |
| A-111 | CH₂C≡CH                               | CH(CH₃)₂                                        |
| A-112 | CH(CH₃)CH=CH₂                         | CH(CH₃)₂                                        |
| A-113 | CHF₂                                  | CH(CH₃)₂                                        |
| A-114 | CH₂Cl                                 | CH(CH₃)₂                                        |
| A-115 | CH₂CH₂CN                              | CH(CH₃)₂                                        |
| A-116 | CH₂CH₂Cl                              | CH(CH₃)₂                                        |
| A-117 | c-C₃H₅                                | CH(CH₃)₂                                        |
| A-118 | c-C₄H₇                                | CH(CH₃)₂                                        |
| A-119 | c-C₅H₉                                | CH(CH₃)₂                                        |
| A-120 | c-C₆H₁₁                               | CH(CH₃)₂                                        |
| A-121 | CH₂-c-C₃H₅                            | CH(CH₃)₂                                        |
| A-122 | CH(CH₃)-c-C₃H₅                        | CH(CH₃)₂                                        |
| A-123 | CH₂-c-C₅H₉                            | CH(CH₃)₂                                        |
| A-124 | CH₂-c-C₆H₁₁                           | CH(CH₃)₂                                        |
| A-125 | C₆H₅                                  | CH(CH₃)₂                                        |
| A-126 | CH₃                                   | CH₂CH₂CH₂CH₃                                    |
| A-127 | C₂H₅                                  | CH₂CH₂CH₂CH₃                                    |
| A-128 | CH=CH₂                                | CH₂CH₂CH₂CH₃                                    |
| A-129 | CH₂CH₂CH₃                             | CH₂CH₂CH₂CH₃                                    |
| A-130 | CH(CH₃)₂                              | CH₂CH₂CH₂CH₃                                    |
| A-131 | CH₂CH₂CH₂CH₃                          | CH₂CH₂CH₂CH₃                                    |
| A-132 | C(CH₃)₃                               | CH₂CH₂CH₂CH₃                                    |
| A-133 | CH₂CH(CH₃)₂                           | CH₂CH₂CH₂CH₃                                    |
| A-134 | CH(CH₃)CH₂CH₃                         | CH₂CH₂CH₂CH₃                                    |
| A-135 | CH₂CH=CH₂                             | CH₂CH₂CH₂CH₃                                    |
| A-136 | CH₂C≡CH                               | CH₂CH₂CH₂CH₃                                    |
| A-137 | CH(CH₃)CH=CH₂                         | CH₂CH₂CH₂CH₃                                    |
| A-138 | CHF₂                                  | CH₂CH₂CH₂CH₃                                    |
| A-139 | CH₂Cl                                 | CH₂CH₂CH₂CH₃                                    |
| A-140 | CH₂CH₂CN                              | CH₂CH₂CH₂CH₃                                    |
| A-141 | CH₂CH₂Cl                              | CH₂CH₂CH₂CH₃                                    |
| A-142 | c-C₃H₅                                | CH₂CH₂CH₂CH₃                                    |
| A-143 | c-C₄H₇                                | CH₂CH₂CH₂CH₃                                    |
| A-144 | c-C₅H₉                                | CH₂CH₂CH₂CH₃                                    |
| A-145 | c-C₆H₁₁                               | CH₂CH₂CH₂CH₃                                    |
| A-146 | CH₂-c-C₃H₅                            | CH₂CH₂CH₂CH₃                                    |
| A-147 | CH(CH₃)-c-C₃H₅                        | CH₂CH₂CH₂CH₃                                    |
| A-148 | CH₂-c-C₅H₉                            | CH₂CH₂CH₂CH₃                                    |
| A-149 | CH₂-c-C₆H₁₁                           | CH₂CH₂CH₂CH₃                                    |
| A-150 | C₆H₅                                  | CH₂CH₂CH₂CH₃                                    |
| A-151 | CH₃                                   | C(CH₃)₃                                         |
| A-152 | C₂H₅                                  | C(CH₃)₃                                         |
| A-153 | CH=CH₂                                | C(CH₃)₃                                         |
| A-154 | CH₂CH₂CH₃                             | C(CH₃)₃                                         |
| A-155 | CH(CH₃)₂                              | C(CH₃)₃                                         |
| A-156 | CH₂CH₂CH₂CH₃                          | C(CH₃)₃                                         |
| A-157 | C(CH₃)₃                               | C(CH₃)₃                                         |
| A-158 | CH₂CH(CH₃)₂                           | C(CH₃)₃                                         |
| A-159 | CH(CH₃)CH₂CH₃                         | C(CH₃)₃                                         |
| A-160 | CH₂CH=CH₂                             | C(CH₃)₃                                         |
| A-161 | CH₂C≡CH                               | C(CH₃)₃                                         |
| A-162 | CH(CH₃)CH=CH₂                         | C(CH₃)₃                                         |
| A-163 | CHF₂                                  | C(CH₃)₃                                         |
| A-164 | CH₂Cl                                 | C(CH₃)₃                                         |
| A-165 | CH₂CH₂CN                              | C(CH₃)₃                                         |
| A-166 | CH₂CH₂Cl                              | C(CH₃)₃                                         |
| A-167 | c-C₃H₅                                | C(CH₃)₃                                         |
| A-168 | c-C₄H₇                                | C(CH₃)₃                                         |
| A-169 | c-C₅H₉                                | C(CH₃)₃                                         |
| A-170 | c-C₆H₁₁                               | C(CH₃)₃                                         |
| A-171 | CH₂-c-C₃H₅                            | C(CH₃)₃                                         |
| A-172 | CH(CH₃)-c-C₃H₅                        | C(CH₃)₃                                         |
| A-173 | CH₂-c-C₅H₉                            | C(CH₃)₃                                         |
| A-174 | CH₂-c-C₆H₁₁                           | C(CH₃)₃                                         |
| A-175 | C₆H₅                                  | C(CH₃)₃                                         |
| A-176 | CH₃                                   | CH₂CH(CH₃)₂                                     |
| A-177 | C₂H₅                                  | CH₂CH(CH₃)₂                                     |
| A-178 | CH=CH₂                                | CH₂CH(CH₃)₂                                     |
| A-179 | CH₂CH₂CH₃                             | CH₂CH(CH₃)₂                                     |
| A-180 | CH(CH₃)₂                              | CH₂CH(CH₃)₂                                     |
| A-181 | CH₂CH₂CH₂CH₃                          | CH₂CH(CH₃)₂                                     |
| A-182 | C(CH₃)₃                               | CH₂CH(CH₃)₂                                     |
| A-183 | CH₂CH(CH₃)₂                           | CH₂CH(CH₃)₂                                     |
| A-184 | CH(CH₃)CH₂CH₃                         | CH₂CH(CH₃)₂                                     |
| A-185 | CH₂CH=CH₂                             | CH₂CH(CH₃)₂                                     |
| A-186 | CH₂C≡CH                               | CH₂CH(CH₃)₂                                     |
| A-187 | CH(CH₃)CH=CH₂                         | CH₂CH(CH₃)₂                                     |
| A-188 | CHF₂                                  | CH₂CH(CH₃)₂                                     |
| A-189 | CH₂Cl                                 | CH₂CH(CH₃)₂                                     |
| A-190 | CH₂CH₂CN                              | CH₂CH(CH₃)₂                                     |
| A-191 | CH₂CH₂Cl                              | CH₂CH(CH₃)₂                                     |
| A-192 | c-C₃H₅                                | CH₂CH(CH₃)₂                                     |
| A-193 | c-C₄H₇                                | CH₂CH(CH₃)₂                                     |
| A-194 | c-C₅H₉                                | CH₂CH(CH₃)₂                                     |
| A-195 | c-C₆H₁₁                               | CH₂CH(CH₃)₂                                     |
| A-196 | CH₂-c-C₃H₅                            | CH₂CH(CH₃)₂                                     |
| A-197 | CH(CH₃)-c-C₃H₅                        | CH₂CH(CH₃)₂                                     |
| A-198 | CH₂-c-C₅H₉                            | CH₂CH(CH₃)₂                                     |
| A-199 | CH₂-c-C₆H₁₁                           | CH₂CH(CH₃)₂                                     |
| A-200 | C₆H₅                                  | CH₂CH(CH₃)₂                                     |
| A-201 | CH₃                                   | CH(CH₃)CH₂CH₃                                   |
| A-202 | C₂H₅                                  | CH(CH₃)CH₂CH₃                                   |
| A-203 | CH=CH₂                                | CH(CH₃)CH₂CH₃                                   |
| A-204 | CH₂CH₂CH₃                             | CH(CH₃)CH₂CH₃                                   |
| A-205 | CH(CH₃)₂                              | CH(CH₃)CH₂CH₃                                   |
| A-206 | CH₂CH₂CH₂CH₃                          | CH(CH₃)CH₂CH₃                                   |
| A-207 | C(CH₃)₃                               | CH(CH₃)CH₂CH₃                                   |
| A-208 | CH₂CH(CH₃)₂                           | CH(CH₃)CH₂CH₃                                   |
| A-209 | CH(CH₃)CH₂CH₃                         | CH(CH₃)CH₂CH₃                                   |
| A-210 | CH₂CH=CH₂                             | CH(CH₃)CH₂CH₃                                   |
| A-211 | CH₂C≡CH                               | CH(CH₃)CH₂CH₃                                   |
| A-212 | CH(CH₃)CH=CH₂                         | CH(CH₃)CH₂CH₃                                   |
| A-213 | CHF₂                                  | CH(CH₃)CH₂CH₃                                   |
| A-214 | CH₂Cl                                 | CH(CH₃)CH₂CH₃                                   |
| A-215 | CH₂CH₂CN                              | CH(CH₃)CH₂CH₃                                   |
| A-216 | CH₂CH₂Cl                              | CH(CH₃)CH₂CH₃                                   |
| A-217 | c-C₃H₅                                | CH(CH₃)CH₂CH₃                                   |
| A-218 | c-C₄H₇                                | CH(CH₃)CH₂CH₃                                   |
| A-219 | c-C₅H₉                                | CH(CH₃)CH₂CH₃                                   |
| A-220 | c-C₆H₁₁                               | CH(CH₃)CH₂CH₃                                   |
| A-221 | CH₂-c-C₃H₅                            | CH(CH₃)CH₂CH₃                                   |

TABLE A-continued

| | R⁵ | R⁶ |
|---|---|---|
| A-222 | CH(CH₃)-c-C₃H₅ | CH(CH₃)CH₂CH₃ |
| A-223 | CH₂-c-C₅H₉ | CH(CH₃)CH₂CH₃ |
| A-224 | CH₂-c-C₆H₁₁ | CH(CH₃)CH₂CH₃ |
| A-225 | C₆H₅ | CH(CH₃)CH₂CH₃ |
| A-226 | CH₃ | CH₂CH=CH₂ |
| A-227 | C₂H₅ | CH₂CH=CH₂ |
| A-228 | CH=CH₂ | CH₂CH=CH₂ |
| A-229 | CH₂CH₂CH₃ | CH₂CH=CH₂ |
| A-230 | CH(CH₃)₂ | CH₂CH=CH₂ |
| A-231 | CH₂CH₂CH₂CH₃ | CH₂CH=CH₂ |
| A-232 | C(CH₃)₃ | CH₂CH=CH₂ |
| A-233 | CH₂CH(CH₃)₂ | CH₂CH=CH₂ |
| A-234 | CH(CH₃)CH₂CH₃ | CH₂CH=CH₂ |
| A-235 | CH₂CH=CH₂ | CH₂CH=CH₂ |
| A-236 | CH₂C≡CH | CH₂CH=CH₂ |
| A-237 | CH(CH₃)CH=CH₂ | CH₂CH=CH₂ |
| A-238 | CHF₂ | CH₂CH=CH₂ |
| A-239 | CH₂Cl | CH₂CH=CH₂ |
| A-240 | CH₂CH₂CN | CH₂CH=CH₂ |
| A-241 | CH₂CH₂Cl | CH₂CH=CH₂ |
| A-242 | c-C₃H₅ | CH₂CH=CH₂ |
| A-243 | c-C₄H₇ | CH₂CH=CH₂ |
| A-244 | c-C₅H₉ | CH₂CH=CH₂ |
| A-245 | c-C₆H₁₁ | CH₂CH=CH₂ |
| A-246 | CH₂-c-C₃H₅ | CH₂CH=CH₂ |
| A-247 | CH(CH₃)-c-C₃H₅ | CH₂CH=CH₂ |
| A-248 | CH₂-c-C₅H₉ | CH₂CH=CH₂ |
| A-249 | CH₂-c-C₆H₁₁ | CH₂CH=CH₂ |
| A-250 | C₆H₅ | CH₂CH=CH₂ |
| A-251 | CH₃ | CH₂C≡CH |
| A-252 | C₂H₅ | CH₂C≡CH |
| A-253 | CH=CH₂ | CH₂C≡CH |
| A-254 | CH₂CH₂CH₃ | CH₂C≡CH |
| A-255 | CH(CH₃)₂ | CH₂C≡CH |
| A-256 | CH₂CH₂CH₂CH₃ | CH₂C≡CH |
| A-257 | C(CH₃)₃ | CH₂C≡CH |
| A-258 | CH₂CH(CH₃)₂ | CH₂C≡CH |
| A-259 | CH(CH₃)CH₂CH₃ | CH₂C≡CH |
| A-260 | CH₂CH=CH₂ | CH₂C≡CH |
| A-261 | CH2C≡CH | CH₂C≡CH |
| A-262 | CH(CH₃)CH=CH₂ | CH₂C≡CH |
| A-263 | CHF₂ | CH₂C≡CH |
| A-264 | CH₂Cl | CH₂C≡CH |
| A-265 | CH₂CH₂CN | CH₂C≡CH |
| A-266 | CH₂CH₂Cl | CH₂C≡CH |
| A-267 | c-C₃H₅ | CH₂C≡CH |
| A-268 | c-C₄H₇ | CH₂C≡CH |
| A-269 | c-C₅H₉ | CH₂C≡CH |
| A-270 | c-C₆H₁₁ | CH₂C≡CH |
| A-271 | CH₂-c-C₃H₅ | CH₂C≡CH |
| A-272 | CH(CH₃)-c-C₃H₅ | CH₂C≡CH |
| A-273 | CH₂-c-C₅H₉ | CH₂C≡CH |
| A-274 | CH₂-c-C₆H₁₁ | CH₂C≡CH |
| A-275 | C₆H₅ | CH₂C≡CH |
| A-276 | CH₃ | CH(CH₃)CH=CH₂ |
| A-277 | C₂H₅ | CH(CH₃)CH=CH₂ |
| A-278 | CH=CH₂ | CH(CH₃)CH=CH₂ |
| A-279 | CH₂CH₂CH₃ | CH(CH₃)CH=CH₂ |
| A-280 | CH(CH₃)₂ | CH(CH₃)CH=CH₂ |
| A-281 | CH₂CH₂CH₂CH₃ | CH(CH₃)CH=CH₂ |
| A-282 | C(CH₃)₃ | CH(CH₃)CH=CH₂ |
| A-283 | CH₂CH(CH₃)₂ | CH(CH₃)CH=CH₂ |
| A-284 | CH(CH₃)CH₂CH₃ | CH(CH₃)CH=CH₂ |
| A-285 | CH₂CH=CH₂ | CH(CH₃)CH=CH₂ |
| A-286 | CH₂C≡CH | CH(CH₃)CH=CH₂ |
| A-287 | CH(CH₃)CH=CH₂ | CH(CH₃)CH=CH₂ |
| A-288 | CHF₂ | CH(CH₃)CH=CH₂ |
| A-289 | CH₂Cl | CH(CH₃)CH=CH₂ |
| A-290 | CH₂CH₂CN | CH(CH₃)CH=CH₂ |
| A-291 | CH₂CH₂Cl | CH(CH₃)CH=CH₂ |
| A-292 | c-C₃H₅ | CH(CH₃)CH=CH₂ |
| A-293 | c-C₄H₇ | CH(CH₃)CH=CH₂ |
| A-294 | c-C₅H₉ | CH(CH₃)CH=CH₂ |
| A-295 | c-C₆H₁₁ | CH(CH₃)CH=CH₂ |
| A-296 | CH₂-c-C₃H₅ | CH(CH₃)CH=CH₂ |
| A-297 | CH(CH₃)-c-C₃H₅ | CH(CH₃)CH=CH₂ |
| A-298 | CH₂-c-C₅H₉ | CH(CH₃)CH=CH₂ |
| A-299 | CH₂-c-C₅H₉ | CH(CH₃)CH=CH₂ |
| A-300 | C₆H₅ | CH(CH₃)CH=CH₂ |
| A-301 | CH₃ | CHF₂ |
| A-302 | C₂H₅ | CHF₂ |
| A-303 | CH=CH₂ | CHF₂ |
| A-304 | CH₂CH₂CH₃ | CHF₂ |
| A-305 | CH(CH₃)₂ | CHF₂ |
| A-306 | CH₂CH₂CH₂CH₃ | CHF₂ |
| A-307 | C(CH₃)₃ | CHF₂ |
| A-308 | CH₂CH(CH₃)₂ | CHF₂ |
| A-309 | CH(CH₃)CH₂CH₃ | CHF₂ |
| A-310 | CH₂CH=CH₂ | CHF₂ |
| A-311 | CH₂C≡CH | CHF₂ |
| A-312 | CH(CH₃)CH=CH₂ | CHF₂ |
| A-313 | CHF₂ | CHF₂ |
| A-314 | CH₂Cl | CHF₂ |
| A-315 | CH₂CH₂CN | CHF₂ |
| A-316 | CH₂CH₂Cl | CHF₂ |
| A-317 | c-C₃H₅ | CHF₂ |
| A-318 | c-C₄H₇ | CHF₂ |
| A-319 | c-C₅H₉ | CHF₂ |
| A-320 | c-C₆H₁₁ | CHF₂ |
| A-321 | CH₂-c-C₃H₅ | CHF₂ |
| A-322 | CH(CH₃)-c-C₃H₅ | CHF₂ |
| A-323 | CH₂-c-C₅H₉ | CHF₂ |
| A-324 | CH₂-c-C₆H₁₁ | CHF₂ |
| A-325 | C₆H₅ | CHF₂ |
| A-326 | CH₃ | CH₂Cl |
| A-327 | C₂H₅ | CH₂Cl |
| A-328 | CH=CH₂ | CH₂Cl |
| A-329 | CH₂CH₂CH₃ | CH₂Cl |
| A-330 | CH(CH₃)₂ | CH₂Cl |
| A-331 | CH₂CH₂CH₂CH₃ | CH₂Cl |
| A-332 | C(CH₃)₃ | CH₂Cl |
| A-333 | CH₂CH(CH₃)₂ | CH₂Cl |
| A-334 | CH(CH₃)CH₂CH₃ | CH₂Cl |
| A-335 | CH₂CH=CH₂ | CH₂Cl |
| A-336 | CH₂C≡CH | CH₂Cl |
| A-337 | CH(CH₃)CH=CH₂ | CH₂Cl |
| A-338 | CHF₂ | CH₂Cl |
| A-339 | CH₂Cl | CH₂Cl |
| A-340 | CH₂CH₂CN | CH₂Cl |
| A-341 | CH₂CH₂Cl | CH₂Cl |
| A-342 | c-C₃H₅ | CH₂Cl |
| A-343 | c-C₄H₇ | CH₂Cl |
| A-344 | c-C₅H₉ | CH₂Cl |
| A-345 | c-C₆H₁₁ | CH₂Cl |
| A-346 | CH₂-c-C₃H₅ | CH₂Cl |
| A-347 | CH(CH₃)-c-C₃H₅ | CH₂Cl |
| A-348 | CH₂-c-C₅H₉ | CH₂Cl |
| A-349 | CH₂-c-C₆H₁₁ | CH₂Cl |
| A-350 | C₆H₅ | CH₂Cl |
| A-351 | CH₃ | CH₂CH₂CN |
| A-352 | C₂H₅ | CH₂CH₂CN |
| A-353 | CH=CH₂ | CH₂CH₂CN |
| A-354 | CH₂CH₂CH₃ | CH₂CH₂CN |
| A-355 | CH(CH₃)₂ | CH₂CH₂CN |
| A-356 | CH₂CH₂CH₂CH₃ | CH₂CH₂CN |
| A-357 | C(CH₃)₃ | CH₂CH₂CN |
| A-358 | CH₂CH(CH₃)₂ | CH₂CH₂CN |
| A-359 | CH(CH₃)CH₂CH₃ | CH₂CH₂CN |
| A-360 | CH₂CH=CH₂ | CH₂CH₂CN |
| A-361 | CH₂C≡CH | CH₂CH₂CN |
| A-362 | CH(CH₃)CH=CH₂ | CH₂CH₂CN |
| A-363 | CHF₂ | CH₂CH₂CN |
| A-364 | CH₂Cl | CH₂CH₂CN |
| A-365 | CH₂CH₂CN | CH₂CH₂CN |
| A-366 | CH₂CH₂Cl | CH₂CH₂CN |
| A-367 | c-C₃H₅ | CH₂CH₂CN |
| A-368 | c-C₄H₇ | CH₂CH₂CN |
| A-369 | c-C₅H₉ | CH₂CH₂CN |
| A-370 | c-C₆H₁₁ | CH₂CH₂CN |
| A-371 | CH₂-c-C₃H₅ | CH₂CH₂CN |
| A-372 | CH(CH₃)-c-C₃H₅ | CH₂CH₂CN |
| A-373 | CH₂-c-C₅H₉ | CH₂CH₂CN |
| A-374 | CH₂-c-C₅H₉ | CH₂CH₂CN |
| A-375 | C₆H₅ | CH₂CH₂CN |
| A-376 | CH₃ | CH₂CH₂Cl |
| A-377 | C₂H₅ | CH₂CH₂Cl |

TABLE A-continued

| | R⁵ | R⁶ |
|---|---|---|
| A-378 | CH=CH₂ | CH₂CH₂Cl |
| A-379 | CH₂CH₂CH₃ | CH₂CH₂Cl |
| A-380 | CH(CH₃)₂ | CH₂CH₂Cl |
| A-381 | CH₂CH₂CH₂CH₃ | CH₂CH₂Cl |
| A-382 | C(CH₃)₃ | CH₂CH₂Cl |
| A-383 | CH₂CH(CH₃)₂ | CH₂CH₂Cl |
| A-384 | CH(CH₃)CH₂CH₃ | CH₂CH₂Cl |
| A-385 | CH₂CH=CH₂ | CH₂CH₂Cl |
| A-386 | CH₂C≡CH | CH₂CH₂Cl |
| A-387 | CH(CH₃)CH=CH₂ | CH₂CH₂Cl |
| A-388 | CHF₂ | CH₂CH₂Cl |
| A-389 | CH₂Cl | CH₂CH₂Cl |
| A-390 | CH₂CH₂CN | CH₂CH₂Cl |
| A-391 | CH₂CH₂Cl | CH₂CH₂Cl |
| A-392 | c-C₃H₅ | CH₂CH₂Cl |
| A-393 | c-C₄H₇ | CH₂CH₂Cl |
| A-394 | c-C₅H₉ | CH₂CH₂Cl |
| A-395 | c-C₆H₁₁ | CH₂CH₂Cl |
| A-396 | CH₂-c-C₃H₅ | CH₂CH₂Cl |
| A-397 | CH(CH₃)-c-C₃H₅ | CH₂CH₂Cl |
| A-398 | CH₂-c-C₅H₉ | CH₂CH₂Cl |
| A-399 | CH₂-c-C₆H₁₁ | CH₂CH₂Cl |
| A-400 | C₆H₅ | CH₂CH₂Cl |
| A-401 | CH₃ | c-C₃H₅ |
| A-402 | C₂H₅ | c-C₃H₅ |
| A-403 | CH=CH₂ | c-C₃H₅ |
| A-404 | CH₂CH₂CH₃ | c-C₃H₅ |
| A-405 | CH(CH₃)₂ | c-C₃H₅ |
| A-406 | CH₂CH₂CH₂CH₃ | c-C₃H₅ |
| A-407 | C(CH₃)₃ | c-C₃H₅ |
| A-408 | CH₂CH(CH₃)₂ | c-C₃H₅ |
| A-409 | CH(CH₃)CH₂CH₃ | c-C₃H₅ |
| A-410 | CH₂CH=CH₂ | c-C₃H₅ |
| A-411 | CH₂C≡CH | c-C₃H₅ |
| A-412 | CH(CH₃)CH=CH₂ | c-C₃H₅ |
| A-413 | CHF₂ | c-C₃H₅ |
| A-414 | CH₂Cl | c-C₃H₅ |
| A-415 | CH₂CH₂CN | c-C₃H₅ |
| A-416 | CH₂CH₂Cl | c-C₃H₅ |
| A-417 | c-C₃H₅ | c-C₃H₅ |
| A-418 | c-C₄H₇ | c-C₃H₅ |
| A-419 | c-C₅H₉ | c-C₃H₅ |
| A-420 | c-C₆H₁₁ | c-C₃H₅ |
| A-421 | CH₂-c-C₃H₅ | c-C₃H₅ |
| A-422 | CH(CH₃)-c-C₃H₅ | c-C₃H₅ |
| A-423 | CH₂-c-C₅H₉ | c-C₃H₅ |
| A-424 | CH₂-c-C₆H₁₁ | c-C₃H₅ |
| A-425 | C₆H₅ | c-C₃H₅ |
| A-426 | CH₃ | c-C₄H₇ |
| A-427 | C₂H₅ | c-C₄H₇ |
| A-428 | CH=CH₂ | c-C₄H₇ |
| A-429 | CH₂CH₂CH₃ | c-C₄H₇ |
| A-430 | CH(CH₃)₂ | c-C₄H₇ |
| A-431 | CH₂CH₂CH₂CH₃ | c-C₄H₇ |
| A-432 | C(CH₃)₃ | c-C₄H₇ |
| A-433 | CH₂CH(CH₃)₂ | c-C₄H₇ |
| A-434 | CH(CH₃)CH₂CH₃ | c-C₄H₇ |
| A-435 | CH₂CH=CH₂ | c-C₄H₇ |
| A-436 | CH₂C≡CH | c-C₄H₇ |
| A-437 | CH(CH₃)CH=CH₂ | c-C₄H₇ |
| A-438 | CHF₂ | c-C₄H₇ |
| A-439 | CH₂Cl | c-C₄H₇ |
| A-440 | CH₂CH₂CN | c-C₄H₇ |
| A-441 | CH₂CH₂Cl | c-C₄H₇ |
| A-442 | c-C₃H₅ | c-C₄H₇ |
| A-443 | c-C₄H₇ | c-C₄H₇ |
| A-444 | c-C₅H₉ | c-C₄H₇ |
| A-445 | c-C₆H₁₁ | c-C₄H₇ |
| A-446 | CH₂-c-C₃H₅ | c-C₄H₇ |
| A-447 | CH(CH₃)-c-C₃H₅ | c-C₄H₇ |
| A-448 | CH₂-c-C₅H₉ | c-C₄H₇ |
| A-449 | CH₂-c-C₆H₁₁ | c-C₄H₇ |
| A-450 | C₆H₅ | c-C₄H₇ |
| A-451 | CH₃ | c-C₅H₉ |
| A-452 | C₂H₅ | c-C₅H₉ |
| A-453 | CH=CH₂ | c-C₅H₉ |
| A-454 | CH₂CH₂CH₃ | c-C₅H₉ |
| A-455 | CH(CH₃)₂ | c-C₅H₉ |
| A-456 | CH₂CH₂CH₂CH₃ | c-C₅H₉ |
| A-457 | C(CH₃)₃ | c-C₅H₉ |
| A-458 | CH₂CH(CH₃)₂ | c-C₅H₉ |
| A-459 | CH(CH₃)CH₂CH₃ | c-C₅H₉ |
| A-460 | CH₂CH=CH₂ | c-C₅H₉ |
| A-461 | CH₂C≡CH | c-C₅H₉ |
| A-462 | CH(CH₃)CH=CH₂ | c-C₅H₉ |
| A-463 | CHF₂ | c-C₅H₉ |
| A-464 | CH₂Cl | c-C₅H₉ |
| A-465 | CH₂CH₂CN | c-C₅H₉ |
| A-466 | CH₂CH₂Cl | c-C₅H₉ |
| A-467 | c-C₃H₅ | c-C₅H₉ |
| A-468 | c-C₄H₇ | c-C₅H₉ |
| A-469 | c-C₅H₉ | c-C₅H₉ |
| A-470 | c-C₆H₁₁ | c-C₅H₉ |
| A-471 | CH₂-c-C₃H₅ | c-C₅H₉ |
| A-472 | CH(CH₃)-c-C₃H₅ | c-C₅H₉ |
| A-473 | CH₂-c-C₅H₉ | c-C₅H₉ |
| A-474 | CH₂-c-C₆H₁₁ | c-C₅H₉ |
| A-475 | C₆H₅ | c-C₅H₉ |
| A-476 | CH₃ | c-C₆H₁₁ |
| A-477 | C₂H₅ | c-C₆H₁₁ |
| A-478 | CH=CH₂ | c-C₆H₁₁ |
| A-479 | CH₂CH₂CH₃ | c-C₆H₁₁ |
| A-480 | CH(CH₃)₂ | c-C₆H₁₁ |
| A-481 | CH₂CH₂CH₂CH₃ | c-C₆H₁₁ |
| A-482 | C(CH₃)₃ | c-C₆H₁₁ |
| A-483 | CH₂CH(CH₃)₂ | c-C₆H₁₁ |
| A-484 | CH(CH₃)CH₂CH₃ | c-C₆H₁₁ |
| A-485 | CH₂CH=CH₂ | c-C₆H₁₁ |
| A-486 | CH₂C≡CH | c-C₆H₁₁ |
| A-487 | CH(CH₃)CH=CH₂ | c-C₆H₁₁ |
| A-488 | CHF₂ | c-C₆H₁₁ |
| A-489 | CH₂Cl | c-C₆H₁₁ |
| A-490 | CH₂CH₂CN | c-C₆H₁₁ |
| A-491 | CH₂CH₂Cl | c-C₆H₁₁ |
| A-492 | c-C₃H₅ | c-C₆H₁₁ |
| A-493 | c-C₄H₇ | c-C₆H₁₁ |
| A-494 | c-C₅H₉ | c-C₆H₁₁ |
| A-495 | c-C₆H₁₁ | c-C₆H₁₁ |
| A-496 | CH₂-c-C₃H₅ | c-C₆H₁₁ |
| A-497 | CH(CH₃)-c-C₃H₅ | c-C₆H₁₁ |
| A-498 | CH₂-c-C₅H₉ | c-C₆H₁₁ |
| A-499 | CH₂-c-C₆H₁₁ | c-C₆H₁₁ |
| A-500 | C₆H₅ | c-C₆H₁₁ |
| A-501 | CH₃ | CH₂-c-C₃H₅ |
| A-502 | C₂H₅ | CH₂-c-C₃H₅ |
| A-503 | CH=CH₂ | CH₂-c-C₃H₅ |
| A-504 | CH₂CH₂CH₃ | CH₂-c-C₃H₅ |
| A-505 | CH(CH₃)₂ | CH₂-c-C₃H₅ |
| A-506 | CH₂CH₂CH₂CH₃ | CH₂-c-C₃H₅ |
| A-507 | C(CH₃)₃ | CH₂-c-C₃H₅ |
| A-508 | CH₂CH(CH₃)₂ | CH₂-c-C₃H₅ |
| A-509 | CH(CH₃)CH₂CH₃ | CH₂-c-C₃H₅ |
| A-510 | CH₂CH=CH₂ | CH₂-c-C₃H₅ |
| A-511 | CH₂C≡CH | CH₂-c-C₃H₅ |
| A-512 | CH(CH₃)CH=CH₂ | CH₂-c-C₃H₅ |
| A-513 | CHF₂ | CH₂-c-C₃H₅ |
| A-514 | CH₂Cl | CH₂-c-C₃H₅ |
| A-515 | CH₂CH₂CN | CH₂-c-C₃H₅ |
| A-516 | CH₂CH₂Cl | CH₂-c-C₃H₅ |
| A-517 | c-C₃H₅ | CH₂-c-C₃H₅ |
| A-518 | c-C₄H₇ | CH₂-c-C₃H₅ |
| A-519 | c-C₅H₉ | CH₂-c-C₃H₅ |
| A-520 | c-C₆H₁₁ | CH₂-c-C₃H₅ |
| A-521 | CH₂-c-C₃H₅ | CH₂-c-C₃H₅ |
| A-522 | CH(CH₃)-c-C₃H₅ | CH₂-c-C₃H₅ |
| A-523 | CH₂-c-C₅H₉ | CH₂-c-C₃H₅ |
| A-524 | CH₂-c-C₆H₁₁ | CH₂-c-C₃H₅ |
| A-525 | C₆H₅ | CH₂-c-C₃H₅ |
| A-526 | CH₃ | CH(CH₃)-c-C₃H₅ |
| A-527 | C₂H₅ | CH(CH₃)-c-C₃H₅ |
| A-528 | CH=CH₂ | CH(CH₃)-c-C₃H₅ |
| A-529 | CH₂CH₂CH₃ | CH(CH₃)-c-C₃H₅ |
| A-530 | CH(CH₃)₂ | CH(CH₃)-c-C₃H₅ |
| A-531 | CH₂CH₂CH₂CH₃ | CH(CH₃)-c-C₃H₅ |
| A-532 | C(CH₃)₃ | CH(CH₃)-c-C₃H₅ |
| A-533 | CH₂CH(CH₃)₂ | CH(CH₃)-c-C₃H₅ |

TABLE A-continued

| | R⁵ | R⁶ |
|---|---|---|
| A-534 | CH(CH₃)CH₂CH₃ | CH(CH₃)-c-C₃H₅ |
| A-535 | CH₂CH=CH₂ | CH(CH₃)-c-C₃H₅ |
| A-536 | CH₂C≡CH | CH(CH₃)-c-C₃H₅ |
| A-537 | CH(CH₃)CH=CH₂ | CH(CH₃)-c-C₃H₅ |
| A-538 | CHF₂ | CH(CH₃)-c-C₃H₅ |
| A-539 | CH₂Cl | CH(CH₃)-c-C₃H₅ |
| A-540 | CH₂CH₂CN | CH(CH₃)-c-C₃H₅ |
| A-541 | CH₂CH₂Cl | CH(CH₃)-c-C₃H₅ |
| A-542 | c-C₃H₅ | CH(CH₃)-c-C₃H₅ |
| A-543 | c-C₄H₇ | CH(CH₃)-c-C₃H₅ |
| A-544 | c-C₅H₉ | CH(CH₃)-c-C₃H₅ |
| A-545 | c-C₆H₁₁ | CH(CH₃)-c-C₃H₅ |
| A-546 | CH₂-c-C₃H₅ | CH(CH₃)-c-C₃H₅ |
| A-547 | CH(CH₃)-c-C₃H₅ | CH(CH₃)-c-C₃H₅ |
| A-548 | CH₂-c-C₅H₉ | CH(CH₃)-c-C₃H₅ |
| A-549 | CH₂-c-C₆H₁₁ | CH(CH₃)-c-C₃H₅ |
| A-550 | C₆H₅ | CH(CH₃)-c-C₃H₅ |
| A-551 | CH₃ | CH₂-c-C₅H₉ |
| A-552 | C₂H₅ | CH₂-c-C₅H₉ |
| A-553 | CH=CH₂ | CH₂-c-C₅H₉ |
| A-554 | CH₂CH₂CH₃ | CH₂-c-C₅H₉ |
| A-555 | CH(CH₃)₂ | CH₂-c-C₅H₉ |
| A-556 | CH₂CH₂CH₂CH₃ | CH₂-c-C₅H₉ |
| A-557 | C(CH₃)₃ | CH₂-c-C₅H₉ |
| A-558 | CH₂CH(CH₃)₂ | CH₂-c-C₅H₉ |
| A-559 | CH(CH₃)CH₂CH₃ | CH₂-c-C₅H₉ |
| A-560 | CH₂CH=CH₂ | CH₂-c-C₅H₉ |
| A-561 | CH₂C≡CH | CH₂-c-C₅H₉ |
| A-562 | CH(CH₃)CH=CH₂ | CH₂-c-C₅H₉ |
| A-563 | CHF₂ | CH₂-c-C₅H₉ |
| A-564 | CH₂Cl | CH₂-c-C₅H₉ |
| A-565 | CH₂CH₂CN | CH₂-c-C₅H₉ |
| A-566 | CH₂CH₂Cl | CH₂-c-C₅H₉ |
| A-567 | c-C₃H₅ | CH₂-c-C₅H₉ |
| A-568 | c-C₄H₇ | CH₂-c-C₅H₉ |
| A-569 | c-C₅H₉ | CH₂-c-C₅H₉ |
| A-570 | c-C₆H₁₁ | CH₂-c-C₅H₉ |
| A-571 | CH₂-c-C₃H₅ | CH₂-c-C₅H₉ |
| A-572 | CH(CH₃)-c-C₃H₅ | CH₂-c-C₅H₉ |
| A-573 | CH₂-c-C₅H₉ | CH₂-c-C₅H₉ |
| A-574 | CH₂-c-C₆H₁₁ | CH₂-c-C₅H₉ |
| A-575 | C₆H₅ | CH₂-c-C₅H₉ |
| A-576 | CH₃ | CH₂-c-C₆H₁₁ |
| A-577 | C₂H₅ | CH₂-c-C₆H₁₁ |
| A-578 | CH=CH₂ | CH₂-c-C₆H₁₁ |
| A-579 | CH₂CH₂CH₃ | CH₂-c-C₆H₁₁ |
| A-580 | CH(CH₃)₂ | CH₂-c-C₆H₁₁ |
| A-581 | CH₂CH₂CH₂CH₃ | CH₂-c-C₆H₁₁ |
| A-582 | C(CH₃)₃ | CH₂-c-C₆H₁₁ |
| A-583 | CH₂CH(CH₃)₂ | CH₂-c-C₆H₁₁ |
| A-584 | CH(CH₃)CH₂CH₃ | CH₂-c-C₆H₁₁ |
| A-585 | CH₂CH=CH₂ | CH₂-c-C₆H₁₁ |
| A-586 | CH₂C≡CH | CH₂-c-C₆H₁₁ |
| A-587 | CH(CH₃)CH=CH₂ | CH₂-c-C₆H₁₁ |
| A-588 | CHF₂ | CH₂-c-C₆H₁₁ |
| A-589 | CH₂Cl | CH₂-c-C₆H₁₁ |
| A-590 | CH₂CH₂CN | CH₂-c-C₆H₁₁ |
| A-591 | CH₂CH₂Cl | CH₂-c-C₆H₁₁ |
| A-592 | c-C₃H₅ | CH₂-c-C₆H₁₁ |
| A-593 | c-C₄H₇ | CH₂-c-C₆H₁₁ |
| A-594 | c-C₅H₉ | CH₂-c-C₆H₁₁ |
| A-595 | c-C₆H₁₁ | CH₂-c-C₆H₁₁ |
| A-596 | CH₂-c-C₃H₅ | CH₂-c-C₆H₁₁ |
| A-597 | CH(CH₃)-c-C₃H₅ | CH₂-c-C₆H₁₁ |
| A-598 | CH₂-c-C₅H₉ | CH₂-c-C₆H₁₁ |
| A-599 | CH₂-c-C₆H₁₁ | CH₂-c-C₆H₁₁ |
| A-600 | C₆H₅ | CH₂-c-C₆H₁₁ |
| A-601 | CH₃ | C₆H₅ |
| A-602 | C₂H₅ | C₆H₅ |
| A-603 | CH=CH₂ | C₆H₅ |
| A-604 | CH₂CH₂CH₃ | C₆H₅ |
| A-605 | CH(CH₃)₂ | C₆H₅ |
| A-606 | CH₂CH₂CH₂CH₃ | C₆H₅ |
| A-607 | C(CH₃)₃ | C₆H₅ |
| A-608 | CH₂CH(CH₃)₂ | C₆H₅ |
| A-609 | CH(CH₃)CH₂CH₃ | C₆H₅ |
| A-610 | CH₂CH=CH₂ | C₆H₅ |
| A-611 | CH₂C≡CH | C₆H₅ |
| A-612 | CH(CH₃)CH=CH₂ | C₆H₅ |
| A-613 | CHF₂ | C₆H₅ |
| A-614 | CH₂Cl | C₆H₅ |
| A-615 | CH₂CH₂CN | C₆H₅ |
| A-616 | CH₂CH₂Cl | C₆H₅ |
| A-617 | c-C₃H₅ | C₆H₅ |
| A-618 | c-C₄H₇ | C₆H₅ |
| A-619 | c-C₅H₉ | C₆H₅ |
| A-620 | c-C₆H₁₁ | C₆H₅ |
| A-621 | CH₂-c-C₃H₅ | C₆H₅ |
| A-622 | CH(CH₃)-c-C₃H₅ | C₆H₅ |
| A-623 | CH₂-c-C₅H₉ | C₆H₅ |
| A-624 | CH₂-c-C₆H₁₁ | C₆H₅ |
| A-625 | C₆H₅ | C₆H₅ |
| A-626 | CH₃ | CH₂-c-C₄H₇ |
| A-627 | C₂H₅ | CH₂-c-C₄H₇ |
| A-628 | CH=CH₂ | CH₂-c-C₄H₇ |
| A-629 | CH₂CH₂CH₃ | CH₂-c-C₄H₇ |
| A-630 | CH(CH₃)₂ | CH₂-c-C₄H₇ |
| A-631 | CH₂CH₂CH₂CH₃ | CH₂-c-C₄H₇ |
| A-632 | C(CH₃)₃ | CH₂-c-C₄H₇ |
| A-633 | CH₂CH(CH₃)₂ | CH₂-c-C₄H₇ |
| A-634 | CH(CH₃)CH₂CH₃ | CH₂-c-C₄H₇ |
| A-635 | CH₂CH=CH₂ | CH₂-c-C₄H₇ |
| A-636 | CH₂C≡CH | CH₂-c-C₄H₇ |
| A-637 | CH(CH₃)CH=CH₂ | CH₂-c-C₄H₇ |
| A-638 | CHF₂ | CH₂-c-C₄H₇ |
| A-639 | CH₂Cl | CH₂-c-C₄H₇ |
| A-640 | CH₂CH₂CN | CH₂-c-C₄H₇ |
| A-641 | CH₂CH₂Cl | CH₂-c-C₄H₇ |
| A-642 | c-C₃H₅ | CH₂-c-C₄H₇ |
| A-643 | c-C₄H₇ | CH₂-c-C₄H₇ |
| A-644 | c-C₅H₉ | CH₂-c-C₄H₇ |
| A-645 | c-C₆H₁₁ | CH₂-c-C₄H₇ |
| A-646 | CH₂-c-C₃H₅ | CH₂-c-C₄H₇ |
| A-647 | CH(CH₃)-c-C₃H₅ | CH₂-c-C₄H₇ |
| A-648 | CH₂-c-C₅H₉ | CH₂-c-C₄H₇ |
| A-649 | CH₂-c-C₆H₁₁ | CH₂-c-C₄H₇ |
| A-650 | C₆H₅ | CH₂-c-C₄H₇ |
| A-651 | CH₃ | CH₂CH₂-c-C₃H₅ |
| A-652 | C₂H₅ | CH₂CH₂-c-C₃H₅ |
| A-653 | CH=CH₂ | CH₂CH₂-c-C₃H₅ |
| A-654 | CH₂CH₂CH₃ | CH₂CH₂-c-C₃H₅ |
| A-655 | CH(CH₃)₂ | CH₂CH₂-c-C₃H₅ |
| A-656 | CH₂CH₂CH₂CH₃ | CH₂CH₂-c-C₃H₅ |
| A-657 | C(CH₃)₃ | CH₂CH₂-c-C₃H₅ |
| A-658 | CH₂CH(CH₃)₂ | CH₂CH₂-c-C₃H₅ |
| A-659 | CH(CH₃)CH₂CH₃ | CH₂CH₂-c-C₃H₅ |
| A-660 | CH₂CH=CH₂ | CH₂CH₂-c-C₃H₅ |
| A-661 | CH₂C≡CH | CH₂CH₂-c-C₃H₅ |
| A-662 | CH(CH₃)CH=CH₂ | CH₂CH₂-c-C₃H₅ |
| A-663 | CHF₂ | CH₂CH₂-c-C₃H₅ |
| A-664 | CH₂Cl | CH₂CH₂-c-C₃H₅ |
| A-665 | CH₂CH₂CN | CH₂CH₂-c-C₃H₅ |
| A-666 | CH₂CH₂Cl | CH₂CH₂-c-C₃H₅ |
| A-667 | c-C₃H₅ | CH₂CH₂-c-C₃H₅ |
| A-668 | c-C₄H₇ | CH₂CH₂-c-C₃H₅ |
| A-669 | c-C₅H₉ | CH₂CH₂-c-C₃H₅ |
| A-670 | c-C₆H₁₁ | CH₂CH₂-c-C₃H₅ |
| A-671 | CH₂-c-C₃H₅ | CH₂CH₂-c-C₃H₅ |
| A-672 | CH(CH₃)-c-C₃H₅ | CH₂CH₂-c-C₃H₅ |
| A-673 | CH₂-c-C₅H₉ | CH₂CH₂-c-C₃H₅ |
| A-674 | CH₂-c-C₆H₁₁ | CH₂CH₂-c-C₃H₅ |
| A-675 | C₆H₅ | CH₂CH₂-c-C₃H₅ |
| A-676 | CH₃ | CH₂(CH₂)₃CH₃ |
| A-677 | C₂H₅ | CH₂(CH₂)₃CH₃ |
| A-678 | CH=CH₂ | CH₂(CH₂)₃CH₃ |
| A-679 | CH₂CH₂CH₃ | CH₂(CH₂)₃CH₃ |
| A-680 | CH(CH₃)₂ | CH₂(CH₂)₃CH₃ |
| A-681 | CH₂CH₂CH₂CH₃ | CH₂(CH₂)₃CH₃ |
| A-682 | C(CH₃)₃ | CH₂(CH₂)₃CH₃ |
| A-683 | CH₂CH(CH₃)₂ | CH₂(CH₂)₃CH₃ |
| A-684 | CH(CH₃)CH₂CH₃ | CH₂(CH₂)₃CH₃ |
| A-685 | CH₂CH=CH₂ | CH₂(CH₂)₃CH₃ |
| A-686 | CH₂C≡CH | CH₂(CH₂)₃CH₃ |
| A-687 | CH(CH₃)CH=CH₂ | CH₂(CH₂)₃CH₃ |
| A-688 | CHF₂ | CH₂(CH₂)₃CH₃ |
| A-689 | CH₂Cl | CH₂(CH₂)₃CH₃ |

TABLE A-continued

| | R⁵ | R⁶ |
|---|---|---|
| A-690 | CH₂CH₂CN | CH₂(CH₂)₃CH₃ |
| A-691 | CH₂CH₂Cl | CH₂(CH₂)₃CH₃ |
| A-692 | c-C₃H₅ | CH₂(CH₂)₃CH₃ |
| A-693 | c-C₄H₇ | CH₂(CH₂)₃CH₃ |
| A-694 | c-C₅H₉ | CH₂(CH₂)₃CH₃ |
| A-695 | c-C₆H₁₁ | CH₂(CH₂)₃CH₃ |
| A-696 | CH₂-c-C₃H₅ | CH₂(CH₂)₃CH₃ |
| A-697 | CH(CH₃)-c-C₃H₅ | CH₂(CH₂)₃CH₃ |
| A-698 | CH₂-c-C₅H₉ | CH₂(CH₂)₃CH₃ |
| A-699 | CH₂-c-C₆H₁₁ | CH₂(CH₂)₃CH₃ |
| A-700 | C₆H₅ | CH₂(CH₂)₃CH₃ |
| A-701 | CH₃ | CH(CH₃)CH(CH₃)₂ |
| A-702 | C₂H₅ | CH(CH₃)CH(CH₃)₂ |
| A-703 | CH=CH₂ | CH(CH₃)CH(CH₃)₂ |
| A-704 | CH₂CH₂CH₃ | CH(CH₃)CH(CH₃)₂ |
| A-705 | CH(CH₃)₂ | CH(CH₃)CH(CH₃)₂ |
| A-706 | CH₂CH₂CH₂CH₃ | CH(CH₃)CH(CH₃)₂ |
| A-707 | C(CH₃)₃ | CH(CH₃)CH(CH₃)₂ |
| A-708 | CH₂CH(CH₃)₂ | CH(CH₃)CH(CH₃)₂ |
| A-709 | CH(CH₃)CH₂CH₃ | CH(CH₃)CH(CH₃)₂ |
| A-710 | CH₂CH=CH₂ | CH(CH₃)CH(CH₃)₂ |
| A-711 | CH₂C≡CH | CH(CH₃)CH(CH₃)₂ |
| A-712 | CH(CH₃)CH=CH₂ | CH(CH₃)CH(CH₃)₂ |
| A-713 | CHF₂ | CH(CH₃)CH(CH₃)₂ |
| A-714 | CH₂Cl | CH(CH₃)CH(CH₃)₂ |
| A-715 | CH₂CH₂CN | CH(CH₃)CH(CH₃)₂ |
| A-716 | CH₂CH₂Cl | CH(CH₃)CH(CH₃)₂ |
| A-717 | c-C₃H₅ | CH(CH₃)CH(CH₃)₂ |
| A-718 | c-C₄H₇ | CH(CH₃)CH(CH₃)₂ |
| A-719 | c-C₅H₉ | CH(CH₃)CH(CH₃)₂ |
| A-720 | c-C₆H₁₁ | CH(CH₃)CH(CH₃)₂ |
| A-721 | CH₂-c-C₃H₅ | CH(CH₃)CH(CH₃)₂ |
| A-722 | CH(CH₃)-c-C₃H₅ | CH(CH₃)CH(CH₃)₂ |
| A-723 | CH₂-c-C₅H₉ | CH(CH₃)CH(CH₃)₂ |
| A-724 | CH₂-c-C₆H₁₁ | CH(CH₃)CH(CH₃)₂ |
| A-725 | C₆H₅ | CH(CH₃)CH(CH₃)₂ |
| A-726 | CH₃ | CH₂(CH₂)₄CH₃ |
| A-727 | C₂H₅ | CH₂(CH₂)₄CH₃ |
| A-728 | C(CH₃)₃ | CH₂(CH₂)₄CH₃ |
| A-729 | CH₂(CH₂)₄CH₃ | CH₂(CH₂)₄CH₃ |
| A-730 | CH₃ | 2-EtHex |
| A-731 | C₂H₅ | 2-EtHex |
| A-732 | C(CH₃)₃ | 2-EtHex |
| A-733 | 2-EtHex | 2-EtHex |
| A-734 | CH₃ | CH₂CH₂OH |
| A-735 | C₂H₅ | CH₂CH₂OH |
| A-736 | C(CH₃)₃ | CH₂CH₂OH |
| A-737 | CH₂CH₂CH₂CH₃ | CH₂CH₂OH |
| A-738 | CH₂(CH₂)₃CH₃ | CH₂CH₂OH |
| A-739 | CH₂CH₂OH | CH₂CH₂OH |
| A-740 | CH₂-c-C₄H₇ | CH₂-c-C₄H₇ |
| A-741 | CH₂CH₂-c-C₃H₅ | CH₂CH₂-c-C₃H₅ |
| A-742 | CH(CH₃)CH(CH₃)₂ | CH(CH₃)CH(CH₃)₂ |
| A-743 | CH₂(CH₂)₃CH₃ | CH₂(CH₂)₃CH₃ |
| A-744 | | (CH₂)₄ |
| A-745 | | CH₂CH₂SCH₂ | c-C₃H₅: cyclopropyl; c-C₄H₇: cyclobutyl; c-C₅H₉: cyclopentyl; c-C₆H₁₁: cyclohexyl; CH₂-c-C₃H₅: cyclopropylmethyl; CH(CH₃)-c-C₃H₅: 1-cyclopylethyl; CH₂-c-C₅H₉: cyclopentylmethyl; CH₂-c-C₆H₁₁: cyclohexylmethyl; C₆H₅: phenyl; CH₂CH₂-c-C₃H₅: 2-cyclopropylethyl; CH₂-c-C₄H₇: 2-cyclobutylmethyl; 2 EtHex: CH₂CH(C₂H₅)(CH₂)₃CH₃

The compounds of the formula (I) can be prepared by the standard methods of organic chemistry, e.g. by the methods described hereinafter in schemes 1 to 6 and in the synthesis descriptions of the working examples. The substituents, variables and indices in schemes 1 to 6 are as defined above for formula (I), if not otherwise specified.

The compounds of formula (I) can be prepared as shown in the Scheme 1 below.

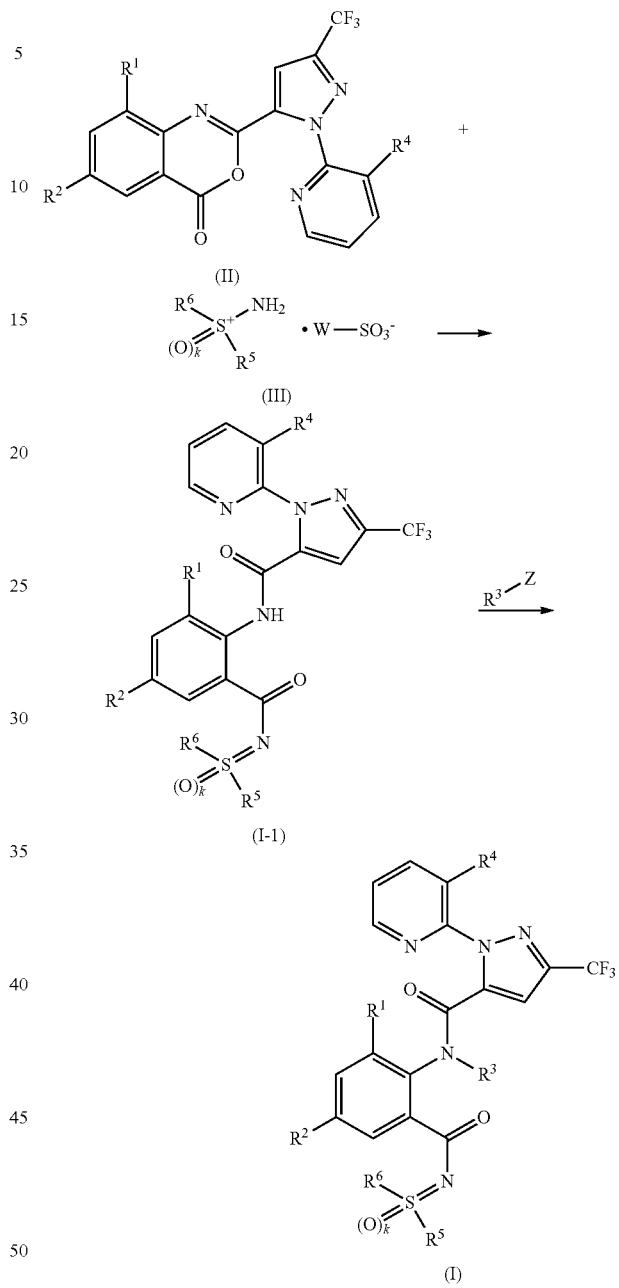

Scheme 1:

Compounds of formula (II) are reacted with compounds of formula (III), in which W can be any group which does not disturb the reaction, such as OH, NH₂, optionally substituted alkyl, optionally substituted aryl or optionally substituted hetaryl, but which is preferably an aromatic group, such as phenyl, optionally substituted with one or more radicals such as defined as R', for example 2,4,6-trimethylphenyl, to give compounds of formula (I-1). The reaction is suitably carried out in a polar or apolar aprotic solvent, such as N,N-dimethylformamide, tetrahydrofuran, dioxane, acetonitrile, dimethylsulfoxide, pyridine, dichloromethane, benzene, toluene, the xylenes or chlorobenzene or mixtures of such solvents, in a temperature range of from 0° C. and 100° C., preferably of from 20° C. and 90° C. The reaction is suitably carried out in the presence of a base. Suitable bases include but are not limited to oxo bases and amine bases. Suitable oxo bases include but are not limited to hydroxides, in particular alkalimetal hydroxides such as lithium, sodium or potassium hydroxide, carbonates, in particular alkalimetal carbonates, such as lithium, sodium or potassium carbonates, hydrogen carbonates, in particular alkalimetal hydrogen carbonates, such as lithium, sodium or potassium hydrogen carbonates, phosphates or hydrogenphosphates, in particular alkalimetal phosphates or hydrogenphosphates, such as lithium, sodium or potassium phosphate, or lithium, sodium or potassium hydrogen phosphate, alkoxides, in particular alkalimetal alkoxides such as sodium or potassium methoxide, sodium or potassium ethoxide or sodium or potassium tert-butanolate, carboxylates, in particular alkalimetal carboxylates, such as lithium, sodium or potassium formiate, lithium, sodium or potassium acetate or lithium, sodium or potassium propionate. Suitable amine bases include but are not limited to ammonia and organic amines, in particular aliphatic or cycloaliphatic amines, e.g. di-$C_1$-$C_4$-alkylamines, tri-$C_1$-$C_4$-alkylamines, $C_3$-$C_6$-cycloalkylamines, $C_3$-$C_6$-cycloalkyl-di-$C_1$-$C_4$-alkylamines or cyclic amines such as dimethylamine, diethylamine, diisopropylamine, cyclohexylamine, dimethylcyclohexylamine, trimethylamine, diethylamine or triethylamine, piperidine and N-methylpiperidine. Preferred bases are oxo bases, in particular alkalimetal alkoxides, which are also termed alkalimetal alkanolates, especially sodium and potassium alkanolates such as sodium methoxides, potassium methoxide, sodium ethoxide, potassium ethoxide, sodium tert-butanolate or potassium tert-butanolate. Mixtures of oxo bases and amine bases may also be used. Compound of formula (III) is typically employed in an amount of from 0.9 to 5 mol, preferably from 0.9 to 3 mol, more preferably from 0.9 to 1.5 mol and in particular from 0.95 to 1.2 mol per mol of the compound of formula (II) used.

For converting compounds of formula (I-1) in which $R^3$ is H into compounds (I) in which $R^3$ is not H, compounds of formula (I-1) can be reacted with compounds of formula $R^3$—Z, wherein $R^3$ is not H and Z is a leaving group, such as for example a bromine, chlorine or iodine atom or a tosylate, mesylate or triflate, to give compounds of formula (I). The reaction is suitably carried out in the presence of a base such as sodium hydride or potassium hydride, suitably in a polar aprotic solvent such as N,N-dimethylformamide, tetrahydrofuran, dioxane, acetonitrile, dimethylsulfoxide or pyridine, or mixtures of these solvents, in a temperature range of from 0° C. and 100 C. In case k is 0 in compounds of formulae (I-1) or (I), a subsequent oxidation reaction in analogy to methods described for example by Dillard et al, Journal of Medicinal Chemistry (1980), 23, 717-722, may be performed to yield compounds of the aforementioned formulae (I-1) or (I), in which k is 1. Other preparation methods for compounds of formula (I) may also be adapted from analogous reactions, as for example described in WO 2007/006670.

Compounds of formula (III) can be obtained as shown in Scheme 2 below.

Scheme 2:

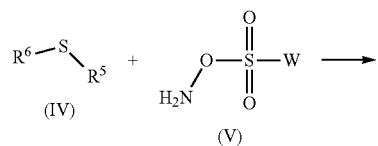

(IV)      (V)

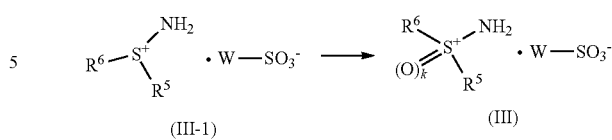

(III-1)      (III)

lp;1pReaction of a sulfonyl hydroxylamine of formula (V), in which W is as defined for scheme 1 and is preferably an aromatic group such as phenyl, optionally substituted with one or more radicals, such as defined as $R^f$, with a sulfide of formula (IV) yields compounds of formula (III-1), corresponding to compounds of formula III in which k is 0, which is described in more detail e.g. by Fujii et al., Heteroatom Chemistry (2004), 15(3), 246-250 or by Young et al, Journal of Organic Chemistry, 1987, (52), 2695-2699. The reaction may also be carried out in analogy to reactions known from literature, in which $R^5$ and $R^6$ have other meanings than in the present invention. In analogy to the described methods an amination reaction of the sulfide of formula (IV) may also be accomplished by applying reagents such as sulfoperamidic acid (W=OH). Compounds of formula (III), in which k is 1, may be obtained from compounds of formula (III-1) by oxidation with an appropriate oxidant, in analogy to described methods as described by, for example, Dillard et al, Journal of Medicinal Chemistry (1980), 23, 717-722. Further preparation methods may also be found in WO 2007/006670 and the references cited therein.

Alternatively, compounds of formula (I), in which k is 0, can also be prepared as shown in scheme 3. Reaction of a compound of formula (VI) with an activated sulfoxide of formula (VII) yields a compound of formula (I), in which k is 0, in analogy to those reactions known from literature, in which the substituents have other meanings than in the present invention, as for example described by Sharma et al, Journal of Organic Chemistry (1975), 40, 2758-2764. Compounds of formula (VI) can be prepared in analogy to the methods described in WO 2009/085816.

Scheme 3:

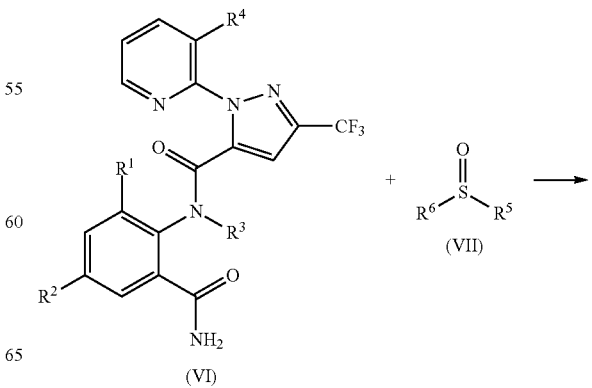

(VI)      (VII)

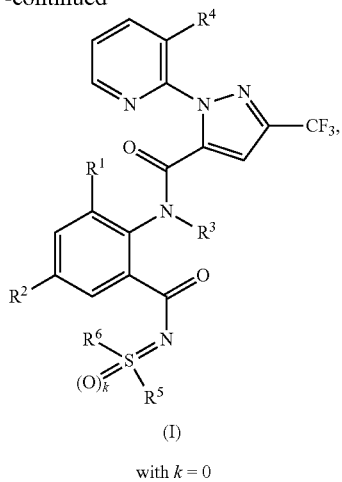

(I)

with k = 0

Alternatively, compounds of formula (I) can also be prepared as shown in scheme 4. Reaction of a compound of formula (VI) with a sulfide of formula (IV) yields a compound of formula (I), in which k is 0, in analogy to methods known in the literature, e.g. Ried et al, Chemische Berichte (1984), 117, 2779-2784. The compound of formula (I), in which k is 0, can be further oxidized by known methods to a compound of formula (I), in which k is 1.

Scheme 4:

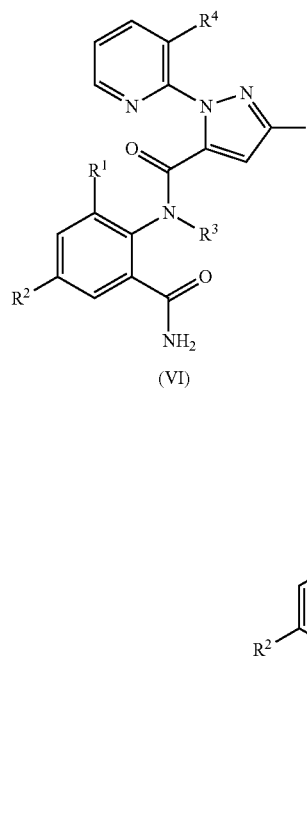

Alternatively, compounds of formula (I) can also be prepared as shown in scheme 5. Reaction of a compound of formula (VII) with a carboxylic acid derivative (VIII) yields compound (I). Z is a leaving group, such as halogen, in particular Cl, an anhydride residue or an active ester residue.

Especially in case of Z being halogen the reaction is suitably carried out in the presence of a base. Suitable bases are for example carbonates, such as lithium, sodium or potassium carbonates, amines, such as trimethylamine or triethylamine, and basic N-heterocycles, such as pyridine, 2,6-dimethylpyridine or 2,4,6-trimethylpyridine. Suitable solvents are in particular aprotic solvents such as pentane, hexane, heptane, octane, cyclohexane, dichloromethane, chloroform, 1,2-dichlorethane, benzene, chlorobenzene, toluene, the xylenes, dichlorobenzene, trimethylbenzene, pyridine, 2,6-dimethylpyridine, 2,4,6-trimethylpyridine, acetonitrile, diethyl ether, tetrahydrofuran, 2-methyl tetrahydrofuran, methyl tert-butylether, 1,4-dioxane, N,N-dimethyl formamide, N-methylpyrrolidinone or mixtures thereof.

Scheme 5

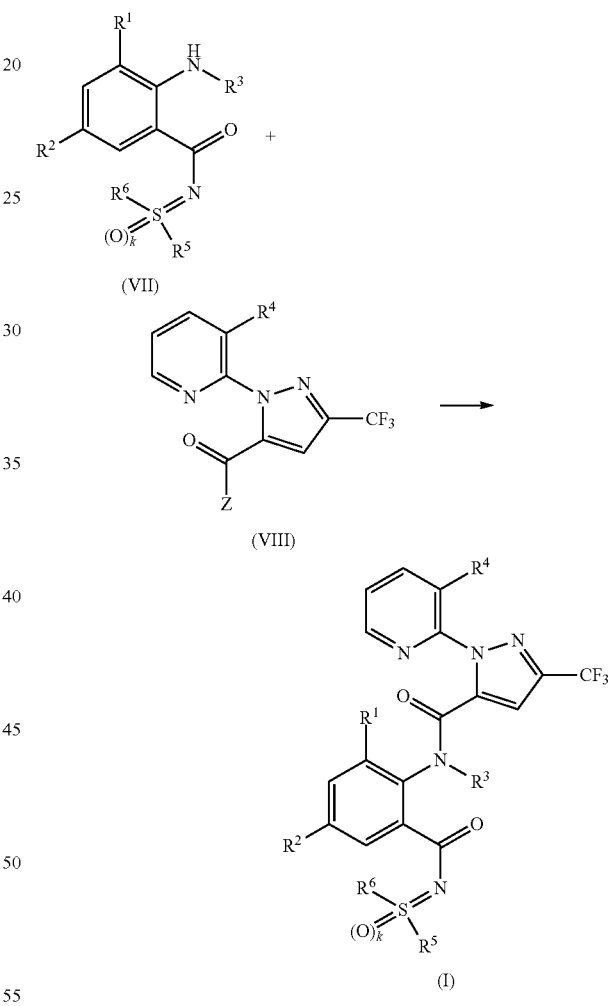

As shown in scheme 6 below the compound of formula (VII) can be obtained by reacting the benzoxazinone (IX) with the sulfinium salt (X) or with the sulfinimin compound of formula (III') which may be an aforementioned compound of formula (III). $A^-$ is the equivalent of an anion, preferably of an anion having a $pK_B$ of at least 10, as determined under standard conditions (298 K, 1.103 bar) in water. Anion equivalent means the amount of anion required to achieve electroneutrality. For example, if the anion carries one negative charge the equivalent is 1, while if the anione carries two negative charges the equivalent is ½. Suitable anions include inorganic ions such as $SO_4^{2-}$, $HSO_4^-$, $Cl^-$, $ClO_4^-$, $BF_4^-$, $PF_6^-$, $HPO_4^-$, and organic anions such as methylsulfonate, trifluoromethylsulfonate, trifluoroacetate, phenylsulfonate, toluenesulfonate, mesitylene sulfonate and the like. The reaction is suitably carried out in the presence of a base. Suitable bases include hydroxides, such as lithium, sodium or potassium hydroxide, carbonates, such as lithium, sodium or potassium carbonates, hydrogen carbonates, such as lithium, sodium or potassium hydrogen carbonates, phosphates, such as lithium, sodium or potassium phosphate, hydrogen phosphate, such as lithium, sodium or potassium hydrogen phosphate, alkoxides, such as sodium or potassium methoxide, sodium or potassium ethoxide or sodium or potassium tert-butanolate, carboxylates, such as lithium, sodium or potassium formiate, lithium, sodium or potassium acetate or lithium, sodium or potassium propionate, ammonia and amines, such as dimethylamine, trimethylamine, diethylamine or triethylamine. Suitable solvents can be protic or aprotic. Examples for aprotic solvents are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride, chloroform or 1,2-dichlorethane, aromatic hydrocarbons, such as benzene, toluene, the xylenes or chlorobenzene, open-chained ethers, such as diethylether, methyl-tert-butyl ether or methyl-isobutyl ether, cyclic ethers, such as tetrahydrofuran, 1,4-dioxane or 2-methyl tetrahydrofuran, or esters, such as ethyl acetate or ethyl propionate. Furthermore, pyridine, 2,6-dimethylpyridine, 2,4,6-trimethylpyridine, N,N-dimethyl formamide, N-methylpyrrolidinone or mixtures of solvents mentioned above or below are suitable. Examples for polar protic solvents are $C_1$-$C_4$-alcohols such as methanol, ethanol, propanol and isopropanol, glycols, such as ethylene glycol and diethylene glycol, and mixtures thereof.

As a rule, the compounds of formula (I) including their stereoisomers, salts, tautomers and N-oxides, and their precursors in the synthesis process [especially (I-1), (II), (III), (III-1), (IV), (V), (VI), (VII)], can be prepared by the methods described above. If individual compounds can not be prepared via the above-described routes, they can be prepared by derivatization of other compounds (I) or the respective precursor or by customary modifications of the synthesis routes described. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

As pointed out above, a further aspect of the present invention relates to a crystalline form of 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide. 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide is a compound of formula I, where both $R^1$ and $R^2$ are chloro, $R^3$ is hydrogen, $R^4$ is chloro and both $R^5$ and $R^6$ are ethyl. This compound is hereinafter also

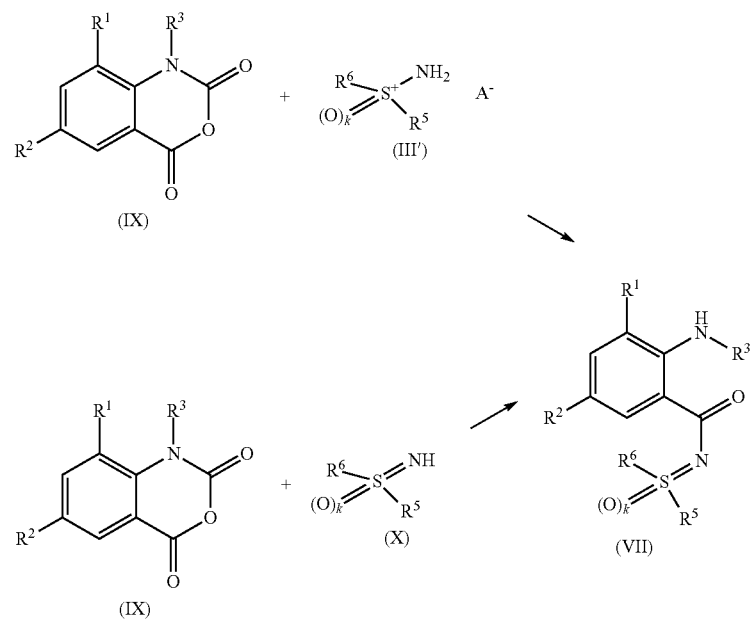

Scheme 6

The compound of formula (III') can be prepared by reacting a sulfide or sulfoxide $S(O)_k R^5 R^6$ with an amination agent, such as aminoxysulfonic acid $NH_2OSO_3H$. The preparation via the sulfide can be carried out in accordance to scheme 2.

termed as compound I-1. The procedure described in scheme 6 above yields the compound of formula I in high yield and high purity, thereby allowing to obtain a form of the compound I-1. This crystalline form is termed form A of I-1.

Form A of I-1 is a stable crystalline form, which forms compact square and rhombic crystals and thus allows a much easier handling than amorphous I-1. Form A of I-1 is a stable crystalline anhydrate, which is essentially free from solvent in the crystal lattice. Form A of I-1 has generally a purity with regard to the compound I-1 of at least 95% by weight.

Referring to form A of I-1, the term "essentially free from solvent" means that the inventive form A of I-1 comprises no detectable amounts of solvents incorporated into the crystal lattice, i.e. the amount of solvent in the crystal lattice is less than 10 mol %, in particular not more than 5 mol %, based on the compound I-1.

Form A of I-1 can be identified by means of X-ray powder diffractometry on the basis of its diffraction diagram. Thus, an X-ray powder diffractogram recorded at 25° C. using Cu-K$_\alpha$ radiation (1.54178 Å) shows as a rule at least 4, frequently at least 5, in particular at least 7, especially at least 9 and specifically all of the 10 reflexes detailed in the table hereinbelow as 2θ values, or as interplanar spacings d:

X-ray powder data of form A of I-1

| 2θ | d [Å] |
|---|---|
| 8.07 ± 0.2 | 10.95 ± 0.3 |
| 9.53 ± 0.2 | 9.28 ± 0.3 |
| 11.00 ± 0.2 | 8.04 ± 0.3 |
| 12.40 ± 0.2 | 7.14 ± 0.3 |
| 14.30 ± 0.2 | 6.19 ± 0.3 |
| 16.65 ± 0.2 | 5.32 ± 0.3 |
| 18.97 ± 0.2 | 4.68 ± 0.3 |
| 21.14 ± 0.2 | 4.30 ± 0.3 |
| 21.48 ± 0.2 | 4.14 ± 0.3 |
| 22.47 ± 0.2 | 3.96 ± 0.3 |

Besides X-ray powder diffractometry, differential scanning calorimetry (DSC) may also be employed for identifying form A of I-1. Form A of I-1 shows a thermogram with a characteristic melting peak in the range between 185 and 189° C. The peak maximum is typically in the range of approximately 186-187° C. The melting points indicated herein refer to data determined by means of differential scanning calorimetry (DSC, crucible material aluminum, heating rate 10 K/min).

Crystallization can be achieved by conventional techniques such as evaporation crystallization or crystallization from a hot solution of I-1 in a suitable aprotic organic solvent such as toluene, xylene, diethyl ether, diisopropyl ether, methyl tert-butyl ether or acetonitrile. For crystallization from hot solvent or evaporation crystallization, the compound I-1 is dissolved in a suitable aprotic organic solvents such as toluene, xylene or acetonitrile. Crystallization can be effected by cooling. Alternatively, crystallization can be effected by removing solvent, e.g. by evaporation. Addition of seed crystals will help to achieve quantitative conversion of the compound I-1 into its crystalline form. However, seed crystals are not necessary. Preferably, crystallization is performed at temperatures in the range from −10 to 100° C., in particular from 0 to 50° C.

Due to their excellent activity, the compounds of the present invention may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of the present invention or a composition as defined above.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of the present invention as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects.

The invention further provides an agricultural composition for combating invertebrate pests, which comprises such an amount of at least one compound according to the invention and at least one inert liquid and/or solid agronomically acceptable carrier that has a pesticidal action and, if desired, at least one surfactant.

Such a composition may comprise a single active compound of the present invention or a mixture of several active compounds of the present invention. The composition according to the present invention may comprise an individual isomer or mixtures of isomers or a salt as well as individual tautomers or mixtures of tautomers.

The compounds of the present invention, including their salts, stereoisomers and tautomers, are in particular suitable for efficiently controlling arthropodal pests such as arachnids, myriapedes and insects as well as nematodes. They are especially suitable for efficiently combating or controlling the following pests:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Pieris rapae, Plathypena scabra, Plutella xylostella, Pseudoplusia includens, Rhyacionia frustrana, Scrobipalpula absoluta, Sitotroga cerealella, Sparganothis pilleriana, Spodoptera* frugiperda, Spodoptera littoralis, Spodoptera litura, Thaumatopoea pityocampa, Tortrix viridana, Trichoplusia ni and Zeiraphera canadensis;

beetles (Coleoptera), for example Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga sp., Phyllopertha horticola, Phyllotreta nemorum, Phyllotreta striolata, Popillia japonica, Sitona lineatus and Sitophilus granaria;

flies, mosquitoes (Diptera), e.g. Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates spp., Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga spp., Simulium vittatum, Stomoxys calcitrans, Tabanus bovinus, Tabanus atratus, Tabanus lineola, and Tabanus similis, Tipula oleracea, and Tipula paludosa;

thrips (Thysanoptera), e.g. Dichromothrips corbetti, Dichromothrips ssp., Frankliniella fusca, Frankliniella occidentalis, Frankliniella tritici, Scirtothrips citri, Thrips oryzae, Thrips palmi and Thrips tabaci;

termites (Isoptera), e.g. Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis, and Coptotermes formosanus;

cockroaches (Blattaria-Blattodea), e.g. Blattella germanica, Blattella asahinae, Periplaneta americana, Periplaneta japonica, Periplaneta brunnea, Periplaneta fuligginosa, Periplaneta australasiae, and Blatta orientalis;

bugs, aphids, leafhoppers, whiteflies, scale insects, cicadas (Hemiptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma spp., and Arilus critatus;

ants, bees, wasps, sawflies (Hymenoptera), e.g. Athalia rosae, Atta cephalotes, Atta capiguara, Atta cephalotes, Atta laevigata, Atta robusta, Atta sexdens, Atta texana, Crematogaster spp., Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus spp., Vespula squamosa, Paravespula vulgaris, Paravespula pennsylvanica, Paravespula germanica, Dolichovespula maculata, Vespa crabro, Polistes rubiginosa, Camponotus floridanus, and Linepithema humile;

crickets, grasshoppers, locusts (Orthoptera), e.g. Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera, and Locustana pardalina; arachnoidea, such as arachnids (Acarina), e.g. of the families Argasidae, Ixodidae and Sarcoptidae, such as Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, *Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis;* Araneida, e.g. *Latrodectus mactans,* and *Loxosceles reclusa;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp., earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

The compounds of the present invention, including their salts, stereoisomers and tautomers, are also suitable for controlling nematodes:plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of the present invention, including their salts, stereoisomers and tautomers, are particularly useful for controlling insects, preferably sucking or piercing and chewing and biting insects such as insects from the genera Lepidoptera, Coleoptera and Hemiptera, in particular Lepidoptera, Coleoptera and true bugs.

The compounds of the present invention, including their salts, stereoisomers and tautomers, are moreover useful for controlling insects of the orders Thysanoptera, Diptera (especially flies, mosquitos), Hymenoptera (especially ants) and Isoptera (especially termites).

The compounds of the present invention, including their salts, stereoisomers and tautomers, are particularly useful for controlling insects of the orders Lepidoptera and Coleoptera.

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling invertebrate pests on cultivated plants or in the protection of materials and which does not result in a substantial damage to the treated plants or material. Such an amount can vary in a broad range and is dependent on various factors, such as the invertebrate (e.g. insect) species to be controlled, the treated cultivated plant or material, the climatic conditions and the specific compound I used.

The compounds I, their stereoisomers, N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005 (see also for review U.S. Pat. No. 3,060,084, EP-A 707 445 (for liquid concentrates), Browning, "Agglomeration", Chemical Engineering, Dec. 4, 1967, 147-48, Perry's Chemical Engineers Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989, D. A. Knowles, Chemistry and Technology of Agrochemical Formulations, Kluwer Academic Publishers, Dordrecht, 1998 (ISBN 0-7514-0443-8).

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsititued fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)

5-25 wt % of a compound I according to the invention and I-10 wt % dispersant (e.g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)

5-40 wt % of a compound I according to the invention and I-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0, 1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

iv) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water up to 100%. This mixture is stirred for 1 h to produce spontaneously a thermodynamically stable microemulsion.

iv) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to I-10 wt %. The wt % relate to the total CS composition.

ix) Dustable Powders (DP, DS)

1-10 wt % of a compound I according to the invention are ground finely and mixed intimately with up to 100 wt % solid carrier, e.g. finely divided kaolin.

x) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xi) Ultra-Low Volume Liquids (UL)

1-50 wt % of a compound I according to the invention are dissolved in up to 100 wt % organic solvent, e.g. aromatic hydrocarbon.

The compositions types i) to xi) may optionally comprise further auxiliaries, such as 0, 1-1 wt % bactericides, 5-15 wt % anti-freezing agents, 0, 1-1 wt % anti-foaming agents, and 0, 1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds I and/or active substances from the groups A) to O), may be mixed by the user in a spray tank and further auxiliaries and additives may be added, if appropriate.

In a further embodiment, either individual components of the composition according to the invention or partially premixed components, e.g. components comprising compounds I and/or active substances from the groups A) to O), can be applied jointly (e.g. after tank mix) or consecutively.

The application of the compounds of formula I or the salts thereof or the herbicidal agents or pesticidal agents containing them is effected, if the formulation is not already ready for use, in the form of aqueous spray fluids. These are prepared by dilution of the aforesaid formulations containing the compound of formula I or a salt thereof with water. The spray fluids can also contain other components in dissolved, emulsified or suspended form, for example fertilizers, active substances of other herbicidal or growth-regulating active substance groups, other active substances, for example active substances for combating animal pests or phyto-pathogenic fungi or bacteria, and also mineral salts which are used for the elimination of nutritional and trace element deficiencies, and non-phytotoxic oils and oil concentrates. As a rule, these components are added to the spray fluid before, during or after the dilution of the formulations according to the invention.

Aqueous use forms can be prepared from the aforementioned formulations i) to x) such as emulsion concentrates, pastes or wettable powders (sprayable powders) or oil dispersions) by adding water or by adding the formulation to water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

In the methods and uses of this invention, the compounds according to the invention may be applied with other active compounds or active ingredients, for example with other pesticides, insecticides, acaricides, fungicides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The invention also relates to a pesticidal combination, comprising at least one compound of the formula I, in particular exactly one compound of the formula I and at least one active compound as mentioned above, in particular at least one active compound from the group of insecticides, acaricides, fungicides, herbicides, plant growth regulators, safeners and nematicides, especially from the group M of pesticides as defined hereinafter and from the group F of fungicides as defined hereinafter.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide and the phtalamid compound (R)—, (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4), 4-[5-(3,5-Dichlorophenyl)-5-trifluoromethyl-4,5-dihydro-isoxazol-3-yl]-N-[(methoxyimino)methyl]-2-methylbenzamide (M22.5) 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M22.6), 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethyl-carbamoyl)-methyl]-amide (M22.7) and 5-[5-(3,5-Dichloro-4-fluoro-phenyl)-5-trifluoromethyl-4,5-dihydro-isoxazol-3-yl]-2-[1,2,4]triazol-1-yl-benzonitrile (M22.8);

M.23. Anthranilamide compounds: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide(M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide(M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11), N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12) and N-(2-carbamoyl-4-chloro-6-methyl-phenyl)2-(3-chloro-2-pyridyl)-5(thriflourmethyl)pyrazole-3-carboxamide (M23.13);

M.24. Malononitrile compounds: 2-(2,2,3,3,4,4,5,5-octafluoropentyl)-2-(3,3,3-trifluoro-propyl)malononitrile $(CF_2HCF_2CF_2CF_2CH_2C(CN)_2CH_2CH_2CF_3)$ (M24.1) and 2-(2,2,3,3,4,4,5,5-octafluoropentyl)-2-(3,3,4,4,4-pentafluorobutyl)-malonodinitrile $(CF_2HCF_2CF_2—CF_2CH_2C(CN)_2CH_2CH_2CF_2CF_3)$ (M24.2);

M.25. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds: 4-{[(6-Bromopyrid-3-yl)methyl](2-fluoroethyl)amino}furan-2(5H)-on (M26.1), 4-{[(6-Fluoropyrid-3-yl)methyl](2,2-difluoroethyl)amino}furan-2(5H)-on (M26.2), 4-{[(2-Chloro1,3-thiazolo-5-yl)methyl](2-fluoroethyl)amino}furan-2(5H)-on (M26.3), 4-{[(6-Chloropyrid-3-yl)methyl](2-fluoroethyl)amino}furan-2(5H)-on (M26.4), 4-{[(6-Chloropyrid-3-yl)methyl] (2,2-difluoroethyl)amino}furan-2(5H)-on (M26.5), 4-{[(6-Chloro-5-fluoropyrid-3-yl)methyl](methyl)amino}furan-2(5H)-on (M26.6), 4-{[(5,6-Dichloropyrid-3-yl)methyl](2-fluoro-ethyl)amino}furan-2(5H)-on (M26.7), 4-{[(6-Chloro-5-fluoropyrid-3-yl)methyl](cyclopro-pyl)amino}furan-2(5H)-on (M26.8), 4-{[(6-Chloropyrid-3-yl)methyl](cyclopropyl)amino}furan-2(5H)-on (M26.9) and 4-{[(6-Chloropyrid-3-yl)methyl](methyl)amino}furan-2 (5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropyl-acetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane(M27.3).

The commercially available compounds of the group M may be found in The Pesticide Manual, 13th Edition, British Crop Protection Council (2003) among other publications. Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779.-AKD 1022 and its preparation have been described in U.S. Pat. No. 6,300,348.-M21.1 is known from WO 2007/101540.-Isoxazolines M22.1 to M22.8 have been described in e.g. WO2005/085216, WO 2007/079162, WO 2007/026965, WO 2009/126668 and WO2009/051956. Anthranilamides M23.1 to M23.6 have been described in WO 2008/72743 and WO 200872783, those M23.7 to M23.12 in WO 2007/043677. Malononitriles M24.1 and M24.2 have been described in WO 02/089579, WO 02/090320, WO 02/090321, WO 04/006677, WO 05/068423, WO 05/068432 and WO 05/063694. Aminofuranones M26.1 to M6.10 have been described eg. in WO 2007/115644. Alkynylether M27.1 is described e.g. in JP 2006131529. Organic sulfur compounds have been described in WO 2007060839. Pyripyropene derivative M27.2 has been described in WO 2008/66153 and WO 2008/108491. Pyridazin M27.3 has been described in JP 2008/115155.

The following list F of active substances, in conjunction with which the compounds according to the invention can be used, is intended to illustrate the possible combinations but does not limit them:

F.I) Respiration Inhibitors

F.I-1) Inhibitors of complex III at Qo site (e.g. strobilurins)
strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)-phenyl)-2-methoxyimino-N methyl-acetamide;
oxazolidinediones and imidazolinones: famoxadone, fenamidone;

F.I-2) Inhibitors of complex II (e.g. carboxamides):
carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;

F.I-3) Inhibitors of complex III at Qi site: cyazofamid, amisulbrom;

F.I-4) Other respiration inhibitors (complex I, uncouplers)
diflumetorim; tecnazen; ferimzone; ametoctradin; silthiofam;
nitrophenyl derivates: binapacryl, dinobuton, dinocap, fluazinam, nitrthal-isopropyl,
organometal compounds: fentin salts, such as fentin-acetate, fentin chloride or fentin hydroxide;

F.II) Sterol biosynthesis inhibitors (SBI fungicides)

F.II-1) C14 demethylase inhibitors (DMI fungicides, e.g. triazoles, imidazoles)
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole;
imidazoles: imazalil, pefurazoate, oxpoconazole, prochloraz, triflumizole; pyrimidines, pyridines and piperazines: fenarimol, nuarimol, pyrifenox, triforine;

F.II-2) Delta 14-reductase inhitors (Amines, e.g. morpholines, piperidines)
morpholines: aldimorph, dodemorph, dodemorph-acetate, fenpropimorph, tridemorph;
piperidines: fenpropidin, piperalin;
spiroketalamines: spiroxamine;

F.II-3) Inhibitors of 3-keto reductase: hydroxyanilides: fenhexamid;

F.III) Nucleic acid synthesis inhibitors

F.III-1) RNA, DNA synthesis phenylamides or acyl amino acid fungicides: benalaxyl, benalaxyl-M, kiralaxyl, metalaxyl, metalaxyl-M (mefenoxam), ofurace, oxadixyl;
isoxazoles and iosothiazolones: hymexazole, octhilinone;

F.III-2) DNA topisomerase inhibitors: oxolinic acid;

F.II-3) Nucleotide metabolism (e.g. adenosin-deaminase) hydroxy(2-amino)-pyrimidines: bupirimate;

F.IV) Inhibitors of cell division and or cytoskeleton

F.IV-1) Tubulin inhibitors: benzimidazoles and thiophanates: benomyl, carbendazim, fuberidazole, thiabendazole, thiophanate-methyl;
triazolopyrimidines: 5-chloro-7 (4-methylpiperidin-1-yl)-6-(2,4,6-trifluorophenyl)-[1,2,4]triazolo[1,5a]pyrimidine F.IV-2) Other cell division inhibitors
benzamides and phenyl acetamides: diethofencarb, ethaboxam, pencycuron, fluopicolide, zoxamide;

F.IV-3) Actin inhibitors: benzophenones: metrafenone;

F.V) Inhibitors of amino acid and protein synthesis

F.V-1) Mmethionine synthesis inhibitors (anilino-pyrimidines)
anilino-pyrimidines: cyprodinil, mepanipyrim, nitrapyrin, pyrimethanil;

F.V-2) Protein synthesis inhibitors (anilino-pyrimidines)
antibiotics: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI-1) MAP/Histidine kinase inhibitors (e.g. anilino-pyrimidines)
dicarboximides: fluoroimid, iprodione, procymidone, vinclozolin;
phenylpyrroles: fenpiclonil, fludioxonil;

F.VI-2) G protein inhibitors: quinolines: quinoxyfen;

F.VII) Lipid and membrane synthesis inhibitors

F.VII-1) Phospholipid biosynthesis inhibitors
organophosphorus compounds: edifenphos, iprobenfos, pyrazophos;
dithiolanes: isoprothiolane;

F.VII-2) Lipid peroxidation
aromatic hydrocarbons: dicloran, quintozene, tecnazene, tolclofos-methyl, biphenyl, chloroneb, etridiazole;

F.VII-3) Carboxyl acid amides (CAA fungicides)
cinnamic or mandelic acid amides: dimethomorph, flumorph, mandipropamid, pyrimorph;
valinamide carbamates: benthiavalicarb, iprovalicarb, pyribencarb, valifenalate and N-(1-(1-(4-cyano-phenyl)ethanesulfonyl)-but-2-yl)carbamic acid-(4-fluorophenyl) ester;

F.VII-4) Compounds affecting cell membrane permeability and fatty acids
carbamates: propamocarb, propamocarb-hydrochlorid F.VIII) Inhibitors with Multi Site Action F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines: guanidine, dodine, dodine free base, guazatine, guazatine-acetate, iminoctadine, iminoctadine-triacetate, iminoctadine-tris(albesilate);

F.VIII-5) Ahtraquinones: dithianon;
F.IX) Cell wall synthesis inhibitors
F.IX-1) Inhibitors of glucan synthesis: validamycin, polyoxin B;
F.IX-2) Melanin synthesis inhibitors: pyroquilon, tricyclazole, carpropamide, dicyclomet, fenoxanil;
F.X) Plant defence inducers
F.X-1) Salicylic acid pathway: acibenzolar-5-methyl;
F.X-2) Others: probenazole, isotianil, tiadinil, prohexadione-calcium;
phosphonates: fosetyl, fosetyl-aluminum, phosphorous acid and its salts;
F.XI) Unknown mode of action:
bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;
F.XI) Growth regulators:
abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;
F.XII) Biological control agents
antifungal biocontrol agents: *Bacillus substilis* strain with NRRL No. B-21661 (e.g. RHAPSODY®, SERENADE® MAX and SERENADE® ASO from AgraQuest, Inc., USA.), *Bacillus pumilus* strain with NRRL No. B-30087 (e.g. SONATA® and BALLAD® Plus from AgraQuest, Inc., USA), *Ulocladium oudemansii* (e.g. the product BOTRY-ZEN from BotriZen Ltd., New Zealand), Chitosan (e.g. ARMOUR-ZEN from BotriZen Ltd., New Zealand).

The invertebrate pest (also referred to as "animal pest"), i.e. the insects, arachnids and nematodes, the plant, soil or water in which the plant is growing or may grow can be contacted with the compounds of the present invention or composition(s) comprising them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

The compounds of the present invention or the pesticidal compositions comprising them may be used to protect growing plants and crops from attack or infestation by animal pests, especially insects, acaridae or arachnids by contacting the plant/crop with a pesticidally effective amount of compounds of the present invention. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

Moreover, invertebrate pests may be controlled by contacting the target pest, its food supply, habitat, breeding ground or its locus with a pesticidally effective amount of compounds of the present invention. As such, the application may be carried out before or after the infection of the locus, growing crops, or harvested crops by the pest.

The compounds of the present invention can also be applied preventively to places at which occurrence of the pests is expected.

The compounds of the present invention may be also used to protect growing plants from attack or infestation by pests by contacting the plant with a pesticidally effective amount of compounds of the present invention. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 1 g to 600 g per hectare, more desirably from 5 g to 500 g per hectare.

The compounds of the present invention are effective through both contact (via soil, glass, wall, bed net, carpet, plant parts or animal parts), and ingestion (bait, or plant part).

The compounds of the present invention may also be applied against non-crop insect pests, such as ants, termites, wasps, flies, mosquitos, crickets, or cockroaches. For use against said non-crop pests, compounds of the present invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active ingredient.

Formulations of compounds of the present invention as aerosols (e.g. in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used. For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of the present invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of the present invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the present invention are also suitable for the treatment of plant propagation material, especially seeds, in order to protect them from insect pest, in particular from soil-living insect pests and the resulting plant's roots and shoots against soil pests and foliar insects.

The compounds of the present invention are particularly useful for the protection of the seed from soil pests and the resulting plant's roots and shoots against soil pests and foliar insects. The protection of the resulting plant's roots and shoots is preferred. More preferred is the protection of resulting plant's roots and shoots from chewing and biting insects, wherein the protection from Lepidoptera and Coleoptera is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the present invention, including a salt thereof. Particularly preferred is a method, wherein the plant's roots and shoots are protected, more preferably a method, wherein the plants roots and shoots are protected form chewing and biting insects, most preferably a method, wherein the plants roots and shoots are protected from Lepidoptera and Coleoptera.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting. The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing *Bacillus thuringiensis* toxins (Bt toxins) which make the plants resistant to certain pests (EP-A 142 924, EP-A 193 259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
  A Soluble concentrates (SL, LS)
  D Emulsions (EW, EO, ES)
  E Suspensions (SC, OD, FS)
  F Water-dispersible granules and water-soluble granules (WG, SG)
  G Water-dispersible powders and water-soluble powders (WP, SP, WS)
  H Gel-Formulations (GF)
  I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds of the present invention are generally from 0.1 g to 10 kg per 100 kg of seed, preferably from 0.5 g to 5 kg per 100 kg of seed, more preferably from 1 g to 1000 g per 100 kg of seed and in particular from 1 g to 200 g per 100 kg of seed.

The invention therefore also relates to seed comprising a compound of the present invention, including an agriculturally useful salt of it, as defined herein. The amount of the compound of the present invention, including an agriculturally useful salt thereof will in general vary from 0.1 g to 10 kg per 100 kg of seed, preferably from 0.5 g to 5 kg per 100 kg of seed, in particular from 1 g to 1000 g per 100 kg of seed. For specific crops such as lettuce the rate can be higher.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of the present invention into contact with each other, and "seed dressing" to methods of seed treatment which provide the seeds with an amount of the compounds of the present invention, i.e. which generate a seed comprising a compound of the present invention. In principle, the treatment can be applied to the seed at any time from the harvest of the seed to the sowing of the seed. The seed can be treated immediately before, or during, the planting of the seed, for example using the "planters box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of the present invention, including their stereoisomers, veterinarily acceptable salts or N-oxides, are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions comprising a parasiticidally effective amount of compounds of the present invention, including their stereoisomers, veterinarily acceptable salts or N-oxides, and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of the present invention, including its stereoisomers, veterinarily acceptable salts or N-oxides, or a composition comprising it.

The invention also provides a process for the preparation of a composition for treating, controlling, preventing or protecting animals against infestation or infection by parasites which comprises a parasiticidally effective amount of a compound of the present invention, including its stereoisomers, veterinarily acceptable salts or N-oxides, or a composition comprising it. Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula (I) and their stereoisomers, veterinarily acceptable salts, tautomers and N-oxides, are suitable for combating endo- and ectoparasites in and on animals.

The compounds of the present invention, especially compounds of formula (I) and their stereoisomers, veterinarily acceptable salts, tautomers and N-oxides, and compositions comprising them are preferably used for controlling and preventing infestations of and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of the present invention, including their stereoisomers, veterinarily acceptable salts or N-oxides, and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention, including their stereoisomers, veterinarily acceptable salts or N-oxides, and compositions comprising them are suitable for systemic and/or non-systemic control of ecto- and/or endoparasites. They are active against all or some stages of development.

The compounds of the present invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans,* and *Nosopsyllus fasciatus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates spp., Hypoderma lineata, Leptoconops torrens, Lucilia caprina, Lucilia cuprina, Lucilia sericata, Lycoria pectoralis, Mansonia spp., Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga sp., Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, roundworms Nematoda:

wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis spp, Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,* intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., thorny headed worms (Acanthocephala), e.g. *Acanthocephalus* spp., *Macracanthorhynchus hirudinaceus* and *Oncicola* spp, Planarians (Plathelminthes):

flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The present invention relates to the therapeutic and the non-therapeutic use of compounds of the present invention and compositions comprising them for controlling and/or combating parasites in and/or on animals. The compounds of the present invention and compositions comprising them may be used to protect the animals from attack or infestation by parasites by contacting them with a parasiticidally effective amount of compounds of the present invention and compositions containing them.

The compounds of the present invention and compositions comprising them can be effective through both contact (via soil, glass, wall, bed net, carpet, blankets or animal parts) and ingestion (e.g. baits). As such, "contacting" includes both direct contact (applying the pesticidal mixtures/compositions containing the compounds of the present invention directly on the parasite, which may include an indirect contact at its locus-P, and optionally also administrating the pesticidal mixtures/composition directly on the animal to be protected) and indirect contact (applying the compounds/compositions to the locus of the parasite). The contact of the parasite through application to its locus is an example of a non-therapeutic use of compounds of the present invention. "Locus-P" as used above means the habitat, food supply, breeding ground, area, material or environment in which a parasite is growing or may grow outside of the animal.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions of the present invention. A parasiticidally effective amount of the compositions will also vary according to the prevailing conditions such as desired parasiticidal effect and duration, target species, mode of application, and the like.

The compounds of the present invention can also be applied preventively to places at which occurrence of the pests or parasites are expected.

Administration can be carried out both prophylactically and therapeutically. Administration of the active compounds is carried out directly or in the form of suitable preparations, orally, topically/dermally or parenterally.

EXAMPLES

The present invention is now illustrated in further details by the following examples and figures, without imposing any limitation thereto.

FIG. 1: X-ray Powder Diffractogramm (XRPD) of crystalline form of 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide, obtained from the example S.6.

Preparation Examples

Compounds can be characterized e.g. by coupled High Performance Liquid Chromatography/mass spectrometry (HPLC/MS), by $^1$H-NMR and/or by their melting points.

The following analytical procedures were employed:

Analytical HPLC column 1: RP-18 column Chromolith Speed ROD (from Merck KGaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

Analytical UPLC column 2: RP-18 column Kinetex 1.7 μm XB-C18 100A; 50×2.1 mm (from Phenomenex Inc., USA). Elution: acetonitrile+0.1% trifluoroacetic acid (TFA)/water+ 0.1% trifluoroacetic acid (TFA) in a ratio of from 5:95 to 95:5 in 1.5 minutes at 60° C.

MS-method: ESI positive.

$^1$H-NMR, respectively $^{13}$C-NMR: The signals are characterized by chemical shift (ppm, 6 [delta]) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplett, q=quartett, t=triplett, d=doublet and s=singulett.

The X-ray powder diffractograms (XRPD) reported herein and displayed in FIG. 1 was recorded using a Panalytical X'Pert Pro diffractometer (manufacturer: Panalytical) in reflection geometry in the range from 2θ=3°-35° C. with increments of 0.0167° C. using Cu-Kα radiation (at 25° C.). The recorded 2θ values were used to calculate the stated interplanar spacings d. The intensity of the peaks (y-axis: linear intensity counts) is plotted versus the 2θ angle (x-axis in degrees 2θ).

DSC was performed on a Mettler Toledo DSC 822e module. Tha samples were placed in crimped but vented aluminium pans. The samples size in each case was 5 to 10 mg. The thermal behaviour was analized in the range 30-300° C. The heating rate was 5 to 10° C./min. The samples were purged with a stream of nitrogen flowing at 150 ml/during the experiment. Melting points values were confirmed by a Mettler Hot Stage in combination with a light microscope.

Abbreviations used are: h for hour(s), min for minute(s) and room temperature for 20-25° C.

A. Synthesis Examples

Starting Materials

Substituted 1H-benzo[d][1,3]oxazine-2,4-diones such as 6,8-dichloro-1H-benzo[d][1,3]oxazine-2,4-dione, 6,8-dibromo-1H-benzo[d][1,3]oxazine-2,4-dione, 6-bromo-8-chloro-1H-benzo[d][1,3]oxazine-2,4-dione, 8-bromo-6-chloro-1H-benzo[d][1,3]oxazine-2,4-dione, 8-chloro-6-trifluoromethyl-1H-benzo[d][1,3]oxazine-2,4-dione, 8-bromo-6-trifluoromethyl-1H-benzo[d][1,3]oxazine-2,4-dione, 8-chloro-6-cyano-1H-benzo[d][1,3]oxazine-2,4-dione, 6-chloro-8-trifluoromethyl-1H-benzo[d][1,3]oxazine-2,4-dione and 6-bromo-8-trifluoromethyl-1H-benzo[d][1,3]oxazine-2,4-dione can be prepared according to WO 2007/43677 or by the following protocol:

To a solution of substituted anthranilic acid (39.9 mmol) in dioxane (170 mL) is added phosgene (20% in toluene, 42.0 mL, 79.9 mmol) over a period of 15 mins. The reaction is stirred at ambient temperature for 48 h and then concentrated in vacuo. The resulting solid is crushed and further dried in vacuo to yield the desired product, which can be used without further purification.

S,S-Diisopropyl-S-aminosulfonium 2,4,6-trimethylbenzenesulfonat, 2,4,6-trimethyl-benzenesulfonate 1-amino-tetrahydro-$\lambda^4$-thiophenium and 2,4,6-trimethyl-benzenesulfonate 1-amino-$\lambda^4$-1,3-ditholanium were prepared according to Y. Tamura et al, Tetrahedron, 1975, 31, 3035-3040.

S,S-Dimethyl Sulfinium Sulfate

To a solution of sodium methylate (15.76 g of a 30% solution in methanol, 87.54 mmol, 1.100 equiv.) in methanol (60 mL) was added dimethyl sulphide (5.44 g, 6.40 mL, 87.6 mmol, 1.10 equiv.) at −5-0° C. To this mixture was added a pre-cooled solution (−20° C.) of hydroxylamine-O-sulfonic acid (9.00 g, 79.6 mmol) in methanol (60 mL) and the internal temperature was maintained at −5 to 0° C. After stirring at room temperature over night, all solids were removed by filtration. The filtrate was concentrated in vacuo and the residue was triturated with acetonitrile (50 mL) to yield the title compound (7.88 g, 39%).

S,S-diethyl sulfinium sulfate, S-ethyl-S-cyclopropyl sulfiniumsulfate, S-cyclopropyl-S-isopropyl sulfinium sulfate, S,S-bis(2-methylpropyl)sulfiniumsulfate, S-ethyl-S-isopropyl sulfinium sulfate, S,S-bis(cyclopropylmethyl) sulfinium sulfate, S,S-bis(2-cyclopropylethyl)sulfinium sulfate, S,S-bis(cyclobutylmethyl)sulfinium sulfate, S,S-bis (cyclopentylmethyl)sulfinium sulfate, S-cyclopropylmethyl-S-ethyl sulfinium sulfate, S-cyclopropylmethyl-S-2-propyl sulfinium sulfate, S-(2-cyclopropylethyl)-S-ethyl sulfinium sulfate, S-(2-cyclopropylethyl)-S-isopropyl sulfinium sulfate, S-(1-cyclopropylethyl)-S-isopropyl sulfinium sulfate, S-cyclobutylmethyl-S-ethyl sulfinium sulfate, S-cyclopentylmethyl-S-ethyl sulfinium sulfate, S-cyclobutylmethyl-S-isopropyl sulfinium sulfate, S-cyclopentylmethyl-S-isopropyl sulfinium sulfate, S,S-di-n-propyl sulfinium sulfate, S,S-di-n-butyl sulfinium sulfate, S,S-di-n-pentyl sulfinium sulfate, S,S-di-n-hexyl sulfinium sulfate, S,S-bis(2-ethylhexyl)sulfinium sulfate, S,S-bis(3-methyl-2-butyl)sulfinium sulfate S,S-bis(3-methyl-1-butyl)sulfinium sulfate, S-3-Methyl-2-butyl-S-ethyl sulfinium sulfate, S-3-Methyl-2-butyl-S-isopropyl sulfinium sulfate and S,S-bis(2-hydroxyethyl) sulfinium sulfate can be prepared by analogy to S,S-Dimethyl sulfinium sulfate.

2-(3-Chloro-pyridin-2-yl)-5-trifluoromethyl-2H-pyrazole-3-carbonyl chloride is known from WO2003/106427 A2.

Example S.1

2-(3-chloro-2-pyridyl)-N-[2,4-dichloro-6-[(bis-2-propyl-$\lambda^4$-sulfanylidene)carbamoyl]phenyl]-5-(trifluoromethyl)pyrazole-3-carboxamide Step 1: Synthesis of 2-amino-N-(bis-2-propyl-$\lambda^4$-sulfanylidene)-3,5-dichloro-benzamide To a suspension of 6,8-dichloro-1H-benzo[d][1,3]oxazine-2,4-dione (45.0 g, 70.7 mmol) in methylene chloride (500 mL) was added S,S-Diisopropyl-S-aminosulfonium 2,4,6-trimethyl-phenylsulfonate (77.6 g, 234 mmol). The reaction mixture was cooled to 0° C. and potassium tert-butanolate (8.73 g, 77.8 mmol) was added after which the reaction was allowed to come to room temperature and stirred for 16 h. Water (200 mL) and methylene chloride (50 mL) were then added, the organic phase was separated and the aqueous phase further extracted with methylene chloride (2×100 mL). The combined organic extracts were dried (MgSO$_4$) and concentrated in vacuo to afford the title compound (62.8 g, quant.).

Step 2: Synthesis of 2-(3-chloro-2-pyridyl)-N-[2,4-dichloro-6-[(bis-2-propyl-$\lambda^4$-sulfanylidene)carbamoyl]phenyl]-5-(trifluoromethyl)pyrazole-3-carboxamide To a solution of the 2-amino-N-(bis-2-propyl-$\lambda^4$-sulfanylidene)-3,5-dichloro-benzamide (26.2 g, 81.6 mmol) and potassium carbonate (12.4 g, 89.7 mmol) in toluene (80 mL) was added N,N-dimethylaminopyridine (0.50 g, 4.1 mmol). The reaction was then heated to 50° C. and 2-(3-chloro-pyridin-2-yl)-5-trifluoromethyl-2H-pyrazole-3-carbonyl chloride (32.3 g, 93.8 mmol) was added dropwise. After stirring for 2 h at this temperature water was added (50 mL) and the reaction stirred for a further 15 min, then cooled to 0° C. and stirred for a further 30 min. The resulting solid was filtered and washed with water and toluene (minimal) to afford the title compound (32.0 g, 66%).

Characterization by HPLC-MS: 3.890 min (column 1), M=596.00.

Example S.2

2-(3-chloro-2-pyridyl)-N-[2-bromo-4-chloro-6-[(tetrahydro-$\lambda^4$-thiophen idene)carbamoyl]phenyl]-5-(trifluoromethyl)pyrazole-3-carboxamide Step 1: Synthesis of 8-Bromo-6-chloro-1H-benzo[d][1,3]oxazine-2,4-dione To a solution of 2-amino-3-bromo-5-chlorobenzoic acid (10.0 g, 39.9 mmol) in dioxane (170 mL) was added phosgene (20% in toluene, 42.0 mL, 79.9 mmol) over a period of 15 min. The reaction was stirred at room temperature for 48 h and then concentrated in vacuo. The resulting solid was crushed and further dried in vacuo to yield the title compound (12.6 g, 114%), which was used in the following step without further purification.

Step 2: Synthesis of 8-bromo-6-chloro-2-[2-(3-chloro-pyridin-2-yl)-5-trifluoromethyl-2H-pyrazol-3-yl]-benzo[d][1,3]oxazin-4-one To a suspension of 8-Bromo-6-chloro-1H-benzo[d][1,3]oxazine-2,4-dione (5.0 g, 18.1 mmol) in acetonitrile (10 mL) was added a solution of 2-(3-chloro-pyridin-2-yl)-5-trifluoromethyl-2H-pyrazole-3-carbonyl chloride (6.45 g, 20.8 mmol) in acetonitrile (8 mL). After stirring for 5 min pyridine (10.4 mL) was added dropwise. The reaction was stirred for a further 30 min at room temperature, then heated to 100° C. for 4 h and stirred for a further 16 h at room temperature. The reaction was then cooled in an ice-bath and the resulting white solid filtered and washed with cold acetonitrile to obtain the title compound (5.88 g, 64%).

Step 3: Synthesis of 2-(3-chloro-2-pyridyl)-N-[2-bromo-4-chloro-6-[(tetrahydro-$\lambda^4$-thiophen idene)carbamoyl]phenyl]-5-(trifluoromethyl)pyrazole-3-carboxamide To a stirred solution of 8-bromo-6-chloro-2-[2-(3-chloro-pyridin-2-yl)-5-trifluoromethyl-2H-pyrazol-3-yl]-benzo[d][1,3]oxazin-4-one (0.4 g, 0.79 mmol) in dimethylsulfoxide (10 mL) was added 2,4,6-trimethyl-benzenesulfonate 1-amino-tetrahydro-$\lambda^4$-thiophenium (0.48 g, 1.58 mmol) followed by potassium butanolate (89 mg, 0.79 mmol). The reaction was stirred at room temperature for 24 h and then poured onto an aqueous solution of ammonium chloride (10% (w/w), 10 mL). The resulting solid was filtered off and then dried in vacuo. The residue was purified via column chromatography (methylene chloride/methanol) to afford the title compound (140 mg, 29%).

Characterization by HPLC-MS: 3.537 min (column 1), M=609.85.

Example S.3

2-(3-chloro-2-pyridyl)-N-[2,4-dichloro-6-[(tetrahydro-$\lambda^4$-thiophen idene)carbamoyl]phenyl]-5-(trifluoromethyl)pyrazole-3-carboxamide Step 1: Synthesis of 2-(3-chloro-2-pyridyl)-N-[2,4-dichloro-6-hydroxycarbonyl-phenyl]-5-(trifluoromethyl)pyrazole-3-carboxamide To a solution of 3,5-dichloroanthranilic acid (7.89 g, 38.3 mmol) in methylene chloride (130 mL) at 0° C. was added triethylamine (18.6 mL, 134.0 mmol). A solution of 2-(3-chloro-pyridin-2-yl)-5-trifluoromethyl-2H-pyrazole-3-carbonyl chloride (13.7 g, 44.0 mmol) in methylene chloride (130 mL) at 0° C. was then added, the reaction allowed to warm to room temperature and then stirred further for 16 h. The reaction was concentrated in vacuo and used directly in the following reaction step.

Step 2: Synthesis of 6,8-dichloro-2-[2-(3-chloro-pyridin-2-yl)-5-trifluoromethyl-2H-pyrazol-3-yl]benzo[d][1,3]oxazin-4-one To a solution of 2-(3-chloro-2-pyridyl)-N-[2,4-dichloro-6-hydroxycarbonyl-phenyl]-5-(trifluoromethyl)pyrazole-3-carboxamide (18.4 g, 38.3 mmol) in methylene chloride (130 mL) was added acetic anhydride (39.4 mL, 417 mmol). The reaction was then heated to 55° C. for 2 h and then stirred for a further 16 h at room temperature. The resulting solid was filtered and washed with cold methylene chloride. Trituration with diethyl ether afforded the title compound (10.1 g, 57%).

Step 3: Synthesis of 2-(3-chloro-2-pyridyl)-N-[2,4-dichloro-6-[(tetrahydro-$\lambda^4$-thiophen idene)carbamoyl]phenyl]-5-(trifluoromethyl)pyrazole-3-carboxamide To a stirred solution 6,8-dichloro-2-[2-(3-chloro-pyridin-2-yl)-5-trifluoromethyl-2H-pyrazol-3-yl]-benzo[d][1,3]oxazin-4-one (0.35 g, 0.76 mmol) in dimethylsulfoxide (12 mL) was added 2,4,6-trimethyl-benzenesulfonate 1-amino-tetrahydro-$\lambda^4$-thiophenium (0.46 g, 1.58 mmol) followed by potassium tert-butanolate (85 mg, 0.79 mmol). The reaction was stirred at room temperature for 24 h and then poured onto an aqueous solution of ammonium chloride (10% (w/w), 10 mL). The resulting solid was filtered off and then dried in vacuo. The residue was purified via trituration with diethyl ether to afford the title compound (110 mg, 26%).

Characterization by HPLC-MS: 3.543 min (column 1), M=564.00.

Example S.6

N-[4,6-dichloro-2-[(diethyl-$\lambda^4$-sulfanylidene)carbamoyl]-phenyl]-2-(3-chloro-2-pyridyl)-5-(trifluoromethyl)pyrazole-3-carboxamide A solution of 6,8-dichloro-1H-3,1-benzoxazine-2,4-dione (187.8 g, 0.81 mol) was added to a suspension of diethyl sulfinium sulfate (173.4 g, 0.56 mol, 0.70 equiv.) in DMSO (1000 mL) followed by addition of triethylamine (93.84 g, 1.15 equiv.) at room temperature. The mixture was stirred for 6 h, and then added dropwise to ice-water. The resulting precipitate was collected by filtration, washed sequentially with water and petrol ether and dried in a vacuum oven to yield the title compound (223.4 g, 94%). HPLC: r.t. 3.312, m/z 293.05 (column 1)

A solution of 2-(3-chloro-2-pyridyl)-5-(trifluoromethyl)pyrazole-3-carbonyl chloride (210.7 g, 0.68 mol, 1.10 equiv.) in acetonitrile (500 mL) was added at 22° C. to a suspension of potassium carbonate (103.34 g, 0.74 mol, 1.20 equiv) and 2-amino-3,5-dichloro-N-(diethyl-$\lambda^4$-sulfanylidene)-benzamide (181.79 g, 0.62 mol, 1.00 equiv) in acetonitrile (2 L). After 2.5 h at this temperature, the reaction mixture was poured into ice-water with stirring. The resulting precipitate was collected by filtration and washed with water and petrol ether. Trituration from diisopropyl ether yielded the crystalline title compound (305 g, 87%).

Characterization by $^1$H-NMR (400 MHz, DMSO-$d_6$): $\delta$[delta]=1.15 (t, 6H), 2.95 (m, 2H), 3.08 (m, 2H), 7.70 (dd, 1H), 7.79 (s, 2H), 7.91 (s, 1H), 8.22 (d, 1H), 8.55 (d, 1H), 10.76 (s, 1H). HPLC: r.t. 1.235, m/z 568 (column 2).

The thus obtained crystalline material was analyzed by means of DSC and by means of X-ray powder diffractometry (XRPD). The data revealed that form A of N-[4,6-dichloro-2-[(diethyl-$\lambda^4$-sulfanylidene)carbamoyl]-phenyl]-2-(3-chloro-2-pyridyl)-5-(trifluoromethyl)pyrazole-3-carboxamide was obtained.

The compounds of examples S.4 to S.52 were prepared by analogy to the methods described for examples S1 to S3 and S.6. The compounds of examples S.1 to S.52 correspond to compound of formula C.1:

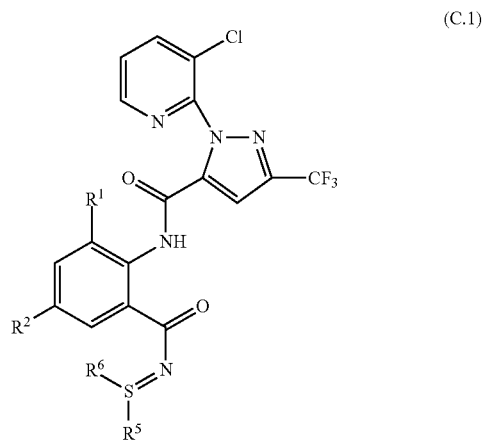

(C.1)

wherein $R^1$, $R^2$, $R^5$ and $R^6$ of each compound example are as defined in table C.1 below. In table C.1 the following abbreviations are used:

Et: Ethyl
n-Pr: n-propyl
i-Pr: isopropyl
3-Me-2-Bu: 3-methyl-2-butyl
3-Me-1-Bu: 3-methyl-1-butyl
n-Bu: n-butyl
n-Pe: n-pentyl
n-Hex: n-hexyl
2-EtHex: 2-ethylhexyl
c-Pr: cyclopropyl
c-Bu: cyclobutyl
c-Pe: cyclopentyl

TABLE C.1

| Ex. | $R^1$ | $R^2$ | $R^5$ | $R^6$ | HPLC-MS: $R_t$ (min) and | [M + H] |
|---|---|---|---|---|---|---|
| S.1 | Cl | Cl | CH(CH$_3$)$_2$ | CH(CH$_3$)$_2$ | 3.890 (column 1) | 596.00 |
| S.2 | Br | Cl | —CH$_2$—CH$_2$—CH$_2$—CH$_2$— | | 3.537 (column 1) | 609.85 |
| S.3 | Cl | Cl | —CH$_2$—CH$_2$—CH$_2$—CH$_2$— | | 3.543 (column 1) | 564.00 |
| S.4 | Cl | Cl | —CH$_2$—S—CH$_2$—CH$_2$— | | 3.613 (column 1) | 583.85 |
| S.5 | Cl | Cl | CH$_3$ | CH$_3$ | 3.372 (column 1) | 539.95 |
| S.6 | Cl | Cl | CH$_2$CH$_3$ | CH$_2$CH$_3$ | 3.496 (column 1) | 567.90 |
| S.7 | Cl | Cl | CH(CH$_3$)$_2$ | CH$_2$CH$_3$ | 1.303 (column 2) | 581.8 |
| S.8 | Cl | Cl | cyclopropyl | CH$_2$CH$_3$ | 1.253 (column 2) | 578.1 |
| S.9 | Cl | Cl | CH$_2$CH(CH$_3$)$_2$ | CH$_2$CH(CH$_3$)$_2$ | 1.408 (column 2) | 623.8 |
| S.10 | Cl | Cl | cyclopropyl | CH(CH$_3$)$_2$ | 1.284 (column 2) | 593.9 |
| S.11 | Cl | Cl | CH$_2$—c-Pr | CH$_2$—c-Pr | 1.518 (column 2) | 620.0 |
| S.12 | Cl | Cl | CH$_2$—c-Pr | Et | 3.704 (column 1) | 594.0 |

TABLE C.1-continued

| Ex. | $R^1$ | $R^2$ | $R^5$ | $R^6$ | HPLC-MS: $R_t$ (min) and | $[M + H]$ |
|---|---|---|---|---|---|---|
| S.13 | Cl | Cl | n-Pr | n-Pr | 3.981 (column 1) | 595.95 |
| S.14 | Br | Cl | i-Pr | i-Pr | 3.630 (column 1) | 639.90 |
| S.15 | Cl | Br | i-Pr | i-Pr | 3.710 (column 1) | 639.90 |
| S.16 | $CF_3$ | Cl | i-Pr | i-Pr | 1.169 (column 2) | 628.1 |
| S.17 | Br | Br | Et | Et | 1.218 (column 2) | 655.9 |
| S.18 | Cl | Cl | $CH_2$—c-Pr | i-Pr | 3.993 (column 1) | 607.95 |
| S.19 | Br | Cl | Et | Et | 3.633 (column 1) | 611.85 |
| S.20 | Cl | Br | Et | Et | 3.704 (column 1) | 611.85 |
| S.21 | Br | Br | i-Pr | i-Pr | 3.665 (column 1) | 683.90 |
| S.22 | Cl | Cl | i-Pr | 2-Me-3-Bu | 1.409 (column 2) | 623.9 |
| S.23 | $CF_3$ | Br | Et | Et | 1.248 (column 2) | 645.9 |
| S.24 | $CF_3$ | Br | i-Pr | i-Pr | 1.308 (column 2) | 673.9 |
| S.25 | $CF_3$ | Cl | Et | Et | 1.231 (column 2) | 600.0 |
| S.26 | Cl | Cl | i-Pr | $CH(CH_3)$—c-Pr | 1.263 (column 2) | 553.9 |
| S.27 | Br | $CF_3$ | Et | Et | 1.301 (column 2) | 646.1 |
| S.28 | Br | $CF_3$ | i-Pr | i-Pr | 1.350 (column 2) | 674 |
| S.29 | Cl | CN | i-Pr | i-Pr | 1.262 (column 2) | 585.3 |
| S.30 | Cl | $CF_3$ | Et | Et | 1.284 (column 2) | 600.1 |
| S.31 | Cl | $CF_3$ | i-Pr | i-Pr | 1.358 (column 2) | 628.1 |
| S.32 | Cl | Cl | 3-Me-2-Bu | 3-Me-2-Bu | 1.488 (column 2) | 652.1 |
| S.33 | Cl | Cl | 3-Me-2-Bu | Et | 1.351 (column 2) | 610 |
| S.34 | Cl | CN | Et | Et | 1.171 (column 2) | 557.3 |
| S.35 | Cl | CN | $CH_2$—c-Pr | $CH_2$—c-Pr | 1.287 (column 2) | 609.1 |
| S.36 | Cl | CN | $CH_2$—c-Pr | Et | 1.236 (column 2) | 583.2 |
| S.37 | Cl | CN | $CH_2$—c-Pr | i-Pr | 1.271 (column 2) | 597.1 |
| S.38 | Cl | Cl | n-Pe | n-Pe | 1.508 (column 2) | 652.1 |
| S.39 | Cl | Cl | 3-Me-1-Bu | 3-Me-1-Bu | 1.489 (column 2) | 652.1 |
| S.40 | Cl | Cl | $CH_2$—c-Bu | $CH_2$—c-Bu | 1.449 (column 2) | 648.1 |
| S.41 | Cl | Cl | Et | $CH_2$—c-Bu | 1.344 (column 2) | 607.9 |
| S.42 | Cl | Cl | n-Hex | n-Hex | 1.588 (column 2) | 680.3 |
| S.43 | Cl | Cl | 2-EtHex | 2-EtHex | 1.679 (column 2) | 461.4 |
| S.44 | Cl | Cl | $CH_2CH_2OH$ | $CH_2CH_2OH$ | 1.064 (column 2) | 600 |
| S.45 | Cl | Cl | $CH_2CH_2$—c-Pr | $CH_2CH_2$—c-Pr | 1.427 (column 2) | 648 |
| S.46 | Cl | Cl | $CH_2CH_2$—c-Pr | i-Pr | 1.374 (column 2) | 622.2 |
| S.47 | Cl | Cl | $CH_2CH_2$—c-Pr | Et | 1.319 (column 2) | 608.2 |
| S.48 | Cl | Cl | $CH_2$—c-Bu | i-Pr | 1.372 (column 2) | 622.2 |
| S.49 | Cl | Cl | Et | Et | 1.242 (column 2) | 584.2 |
| S.50 | Cl | Cl | $CH_2$—c-Pe | $CH_2$—c-Pe | 1.514 (column 2) | 676.2 |

TABLE C.1-continued

| Ex. | R¹ | R² | R⁵ | R⁶ | HPLC-MS: $R_t$ (min) and [M + H] | |
|---|---|---|---|---|---|---|
| S.51 | Cl | Cl | CH₂—c-Pe | Et | 1.385 (column 2) | 620.2 |
| S.52 | Cl | Cl | CH₂—c-Pe | i-Pr | 1.401 (column 2) | 636 |

B. Biological Examples

The activity of the compounds of formula (I) of the present invention could be demonstrated and evaluated in biological tests described in the following.

If not otherwise specified, test solutions were prepared as follow:

The active compound is dissolved at the desired concentration in a mixture of 1:1 (vol:vol) distilled water:acteon. The test solution was prepared at the day of use.

Test solutions were prepared in general at concentrations of 2500 ppm, 1415 ppm, 1000 ppm, 500 ppm, 300 ppm, 100 ppm, 50 ppm, 30 ppm and 5 ppm (wt/vol).

B.1 Cowpea Aphid (*Aphis craccivora*)

The active compound is dissolved at the desired concentration in a mixture of 1:1 (vol:vol) distilled water:acetone. Surfactant (Alkamuls® EL 620) is added at a rate of 0.1% (vol/vol). The test solution is prepared at the day of use.

Potted cowpea plants were colonized with approximately 50 to 100 aphids of various stages by manually transferring a leaf tissue cut from infested plant 24 hours before application. Plants were sprayed after the pest population has been recorded. Treated plants are maintained on light carts at about 28° C. Percent mortality was assessed after 72 hours.

In this test, compounds S.1, S.2, S.3, S.4, S.5, S.6, S.7, S.8, S.10, S.11, S.12, S.13, S.14,
S.15, S.17, S.18, S.19, S.20, S.21, S.22, S.25, S.26, S.42, S.44 and S.46 at 300 ppm showed over 75% mortality in comparison with untreated controls.

B.2 Diamond Back Moth (*Plutella xylostella*)

The active compound is dissolved at the desired concentration in a mixture of 1:1 (vol:vol) distilled water:acetone. Surfactant (Alkamuls® EL 620) is added at a rate of 0.1% (vol/vol).The test solution is prepared at the day of use.

Leaves of cabbage were dipped in test solution and air-dried. Treated leaves were placed in petri dish eslined with moist filter paper and inoculated with ten 3rd instar larvae. Mortality was recorded 72 hours after treatment. Feeding damages were also recorded using a scale of 0-100%.

In this test, compounds S.1, S.2, S.3, S.4, S.5, S.6, S.7, S.8, S.9, S.10, S.11, S.12, S.13, S.14, S.15, S.16, S.17, S.18, S.19, S.20, S.21, S.22, S.23, S.24, S.25, S.26, S.27, S.28, S.29, S.30, S.31, S.32, S.33, S.34, S.35, S.36, S.37, S.38, S.39, S.40, S.41, S.42, S.44, S.45 and S.46 at 300 ppm showed over 75% mortality in comparison with untreated controls.

B.3 Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5 to 8 adult aphids were placed on the artificial membrane inside the microtiter plate wells. The aphids were then allowed to suck on the treated aphid diet and incubated at about 23+1° C. and about 50+5% relative humidity for 3 days. Aphid mortality and fecundity was then visually assessed.

In this test, compounds S.1, S.2, S.3, S.4, S.5, S.6, S.7, S.8, S.9, S.10, S.10, S.11, S.12, S.13, S.14, S.15, S.17, S.18, S.19, S.20, S.21, S.22, S.23, S.25, S.26, S.27, S.28, S.29, S.30, S.31, S.34, S.35, S.36, S.37, S.38, S.39, S.40, S.41, S.42, S.43, S.44, S.45 and S.46 and I-10 at 2500 ppm showed over 75% mortality in comparison with untreated controls.

B.4 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 28+1° C. and about 80+5% relative humidity for 5 days. Egg and larval mortality was then visually assessed.

In this test, compounds S.1, S.2, S.3, S.4, S.5, S.8, S.9, S.10, S.13, S.14, S.15, S.16, S.17, S.18, S.21, S.22, S.23, S.24, S.25, S.26, S.27, S.28, S.29, S.30, S.31, S.34, S.35, S.36, S.37, S.38, S.39, S.40, S.41, S.42, S.44, S.45 and S.46 at 2500 ppm showed over 75% mortality in comparison with untreated controls.

B.5 Orchid Thrips (*Dichromothrips Corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus 0.01% vol/vol Alkamuls® EL 620 surfactant.

Thrips potency of each compound was evaluated by using a floral-immersion technique. Plastic petri dishes were used as test arenas. All petals of individual, intact orchid flowers were dipped into treatment solution and allowed to dry. Treated flowers were placed into individual petri dishes along with about 20 adult thrips. The petri dishes were then covered with lids. All test arenas were held under continuous light and a temperature of about 28° C. for duration of the assay. After 3 days, the numbers of live thrips were counted on each flower, and along inner walls of each petri dish. The percent-mortality was recorded 72 hours after treatment.

In this test, compounds S.1, S.2, S.3, S.4, S.5, S.6, S.7, S.8, S.9, S.10, S.11, S.12, S.13, S.14, S.15, S.16, S.17, S.18, S.19, S.20, S.21, S.22, S.23, S.25, S.26, S.27, S.28, S.29, S.30, S.31, S.32, S.33, S.34, S.35, S.36, S.37, S.38, S.41, S.44, S.45 and S.46 at 300 ppm showed over 75% mortality in comparison with untreated controls.

B.6 Rice Green Leafhopper (*Nephotettix Virescens*)

Rice seedlings were cleaned and washed 24 hours before spraying. The active compounds were formulated in 50:50 acetone:water (vol:vol), and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, compounds S.4, S.7, S.10 and S.13 at 300 ppm showed over 75% mortality in comparison with untreated controls.

B.7 Vetch Aphid (*Megoura Viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5 to 8 adult aphids placed on the leaf disks inside the microtiter plate wells. The aphids were then allowed to suck on the treated leaf disks and incubated at about 23+1° C. and about 50+5% relative humidity for 5 days. Aphid mortality and fecundity was then visually assessed.

In this test, compounds S.1, S.2, S.3, S.4, S.5, S.6, S.7, S.8, S.9, S.10, S.11, S.12, S.13, S.14, S.15, S.17, S.18, S.19, S.20, S.21, S.22, S.26, S.28, S.29, S.30, S.31, S.34, S.35, S.36, S.37, S.38, S.39, S.40, S.41, S.42, S.43, S.44, S.45 and S.46 at 2500 ppm showed over 75% mortality in comparison with untreated controls.

B.8 Tobacco Budworm (*Heliothis virescens*) I

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 µl, using a custom built micro atomizer, at two replications.

After application, microtiter plates were incubated at about 28+1° C. and about 80+5% relative humidity for 5 days. Egg and larval mortality was then visually assessed.

In this test, compounds S.1, S.2, S.3, S.4, S.5, S.6, S.7, S.8, S.9, S.10, S.11, S.12, S.13, S.14, S.15, S.16, S.17, S.18, S.19, S.20, S.21, S.22, S.23, S.24, S.25, S.26, S.27, S.28, S.29, S.30, S.31, S.34, S.35, S.36, S.37, S.38, S.39, S.40, S.41, S.42, S.44, S.45 and S.46 at 2500 ppm showed over 75% mortality in comparison with untreated controls.

B.9 Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 25+1° C. and about 75+5% relative humidity for 5 days. Egg and larval mortality was then visually assessed.

In this test, compounds S.1, S.2, S.3, S.4, S.5, S.6, S.7, S.8, S.9, S.10, S.11, S.12, S.13, S.14, S.15, S.16, S.17, S.18, S.19, S.20, S.21, S.22, S.23, S.24, S.25, S.26, S.27, S.28, S.29, S.30, S.31, S.34, S.35, S.36, S.37, S.38, S.39, S.40, S.41, S.42, S.44, S.45 and S.46 at 2500 ppm showed over 95% mortality in comparison with untreated controls.

B.10 Silverleaf Whitefly (*Bemisia Argentifolii*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was pla-ced into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, compounds S.11, S.13, S.14, S.18, S.20, S.21, S.26 and S.31 at 100 ppm showed over 75% mortality in comparison with untreated controls.

For purpose of comparison with prior art, the following comparative compounds CC-1 to CC-3 corresponding to compounds formula C.2 have been tested:

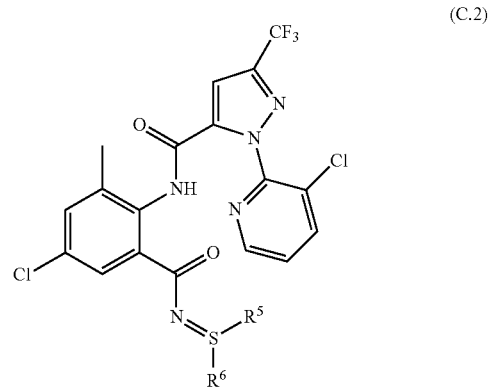

(C.2)

| Compound Ex. | $R^5$ | $R^6$ | Origin in WO 2007/006670 |
|---|---|---|---|
| CC-1 | | $(CH_2)_4$ | Table 925, Compound with radical A.13 |
| CC-2 | $CH_2CH_3$ | $CH_2CH_3$ | Table 631, Compound IA-173 |
| CC-3 | $CH(CH_3)_2$ | $CH(CH_3)_2$ | Table III, Compound I.3-6 |

The activity summarized in the tables hereinbelow are given as percentage of mortality in comparison with untreated control CE.1 Cowpea Aphid (*Aphis Craccivora*)

The active compound was dissolved at the desired concentration in a mixture of 1:1 (vol:vol) distilled water:acetone. Surfactant (Alkamuls® EL 620) is added at a rate of 0.1% (vol/vol). The test solution was prepared at the day of use.

Potted cowpea plants were colonized with approximately 50 to 100 aphids of various stages by manually transferring a leaf tissue cut from infested plant 24 hours before application.

Plants were sprayed after the pest population has been recorded. Treated plants are maintained on light carts at about 28° C. Percent mortality was assessed after 72 hours.

Compound S.1 in comparison with comparative compound CC-3 showed superior activity against Cowpea aphid:

| Concentration[1] [ppm] | Compound S.1 % activity[2] | Comparative compound CC-3 % activity[2] |
|---|---|---|
| 500 | 100 | 100 |
| 300 | 100 | 92 |
| 100 | 100 | 84 |

[1] concentration of active ingredient
[2] mortality of Cowpea aphid in %, vs. untreated control CE.2 Western Corn Rootworm Assay (*Diabrotica virgifera virgifera*)

The active compound was applied in acetone at rates of 5 and 50 ppm a.i./soil (w/w). Treatments were applied in solution to sifted, North Carolina loamy sand (Sandhill soil) in a plastic bag. Treatments were thoroughly incorporated by sealing and shaking each bag by hand and allowing the solution to soak through the soil mass for at least 10 minutes before unsealing. The bags were then kept open in a fume hood overnight to evaporate the solvent from the soil.

One day after treatment (DAT) distilled water for moisture and water-soaked millet seed (*Panicum miliaceum* 'white millet') as a food source were added to each bag and mixed in thoroughly. 11 cm³ of millet and soil mixture were dispensed into a 1 oz. plastic cup. Each cup was infested with 10 western corn rootworm second-instar larvae. Each cup or group of four cells was a replicate, and replication was 3×. The test was maintained in incubators at 26° C. in the dark. Mortality was evaluated 3 days after infestation (DAI) and mean percent mortality was calculated.

| Concentration[1] [ppm] | Compound S.1 % activity[2] | Comparative compound CC-3 % activity[2] |
|---|---|---|
| 50 | 100 | 71 |
| 5 | 100 | 0 |

[1] concentration of active ingredient
[2] mortality of Western corn rootworm in %, vs. untreated control

| Concentration[1] [ppm] | Compound S.6 % activity[2] | Comparative compound CC-2 % activity[2] |
|---|---|---|
| 50 | 100 | 93 |
| 5 | 100 | 21 |

[1] concentration of active ingredient
[2] mortality of Western corn rootworm in %, vs. untreated control CE.3 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 28±1° C. and about 80±5% relative humidity for 5 days. Egg and larval mortality was then visually assessed.

Compound S.3 in comparison with comparative compound CC-1 showed superior activity against Mediterranean fruit-fly:

| Concentration[1] [ppm] | Compound S.1 % activity[2] | Comparative compound CC-3 % activity[2] |
|---|---|---|
| 2500 | 100 | 88 |
| 1415 | 100 | 75 |

[1] concentration of active ingredient
[2] mortality of Mediterranean fruitfly rootworm in %, vs. untreated control

The invention claimed is:
1. A compound of formula (I)

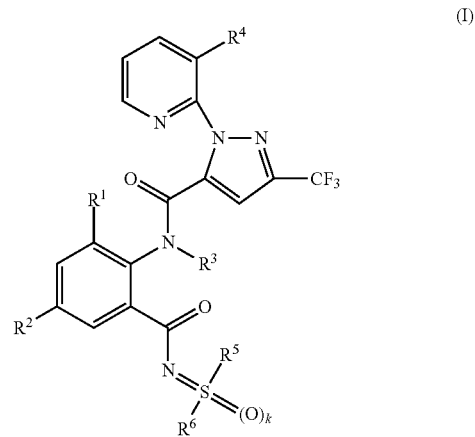

wherein
R¹ is selected from the group consisting of halogen and halomethyl;
R² is selected from the group consisting of hydrogen, halogen, halomethyl and cyano;
R³ is selected from the group consisting of hydrogen, $C_1$-$C_6$ alkyl, $C_1$-$C_6$ haloalkyl, $C_2$-$C_6$-alkenyl, $C_2$-$C_6$-haloalkenyl, $C_2$-$C_6$-alkinyl, $C_2$-$C_6$-haloalkinyl, $C_3$-$C_8$-cycloalkyl, $C_3$-$C_8$-halocycloalkyl, $C_1$-$C_4$-alkoxy-$C_1$-$C_4$-alkyl, $C_1$-$C_4$-haloalkoxy-$C_1$-$C_4$-alkyl, C(=O)R$^a$, C(=O)OR$^b$ and C(=O)NR$^c$R$^d$;
R⁴ is halogen;
R⁵, R⁶ are selected independently of one another from the group consisting of hydrogen, $C_1$-$C_{10}$-alkyl, $C_3$-$C_8$-cycloalkyl, $C_2$-$C_{10}$-alkenyl, $C_2$-$C_{10}$-alkynyl, wherein the aforementioned aliphatic and cycloaliphatic radicals may be substituted with 1 to 10 substituents R$^e$, and phenyl, which is unsubstituted or carries 1 to 5 substituents R$^f$; or
R⁵ and R⁶ together represent a $C_2$-$C_7$-alkylene, $C_2$-$C_7$-alkenylene or $C_6$-$C_9$-alkynylene chain forming together with the sulfur atom to which they are attached a 3-, 4-, 5-, 6-, 7-, 8-, 9 or 10-membered saturated, partially unsaturated or fully unsaturated ring, wherein 1 to 4 of the CH₂ groups in the $C_2$-$C_7$-alkylene chain or 1 to 4 of any of the CH₂ or CH groups in the $C_2$-$C_7$-alkenylene chain or 1 to 4 of any of the CH₂ groups in the $C_6$-$C_9$-alkynylene chain may be replaced by 1 to 4 groups independently selected from the group consisting of C=O, C=S, O, S, N, NO, SO, SO₂ and NH, and wherein the carbon and/or nitrogen atoms in the $C_2$-$C_7$alkylene, $C_2$-$C_7$-alkenylene or $C_6$-$C_9$-alkynylene chain may be substituted with 1 to 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl and $C_2$-$C_6$-haloalkynyl; said substituents being identical or different from one another if more than one substituent is present;

$R^a$ is selected from the group consisting of $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, $C_1$-$C_6$-alkylthio, $C_1$-$C_6$-alkylsulfinyl, and $C_1$-$C_6$-alkylsulfonyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 substituents selected from the group consisting of $C_1$-$C_4$ alkoxy, phenyl, benzyl, pyridyl and phenoxy, wherein the last four radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$-haloalkoxy, ($C_1$-$C_6$-alkoxy)carbonyl, $C_1$-$C_6$-alkylamino and di-($C_1$-$C_6$-alkyl)amino;

$R^b$ is selected from the group consisting of $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, $C_1$-$C_6$-alkylthio, $C_1$-$C_6$-alkylsulfinyl, $C_1$-$C_6$-alkylsulfonyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 substituents selected from $C_1$-$C_4$-alkoxy;

phenyl, benzyl, pyridyl and phenoxy, wherein the last four radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkox, $C_1$-$C_6$-haloalkoxy and ($C_1$-$C_6$-alkoxy)carbonyl;

$R^c$, $R^d$ are, independently from one another and independently of each occurrence, selected from the group consisting of hydrogen, cyano, $C_1$-$C_6$-alkyl, $C_2$-$C_6$-alkenyl, $C_2$-$C_6$-alkynyl, $C_3$-$C_8$-cycloalkyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 radicals selected from $C_1$-$C_4$-alkoxy;

$C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, phenyl, benzyl, pyridyl and phenoxy, wherein the four last mentioned radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl; or $R^c$ and $R^d$, together with the nitrogen atom to which they are bound, may form a 3-, 4-, 5-, 6- or 7-membered saturated, partially unsaturated or fully unsaturated heterocyclic ring which may additionally contain 1 or 2 further heteroatoms or heteroatom groups selected from the group consisting of N, O, S, NO, SO and $SO_2$, as ring members, where the heterocyclic ring may optionally be substituted with halogen, $C_1$-$C_4$-haloalkyl, $C_1$-$C_4$-alkoxy or $C_1$-$C_4$-haloalkoxy;

$R^e$ is independently selected from the group consisting of halogen, cyano, nitro, —OH, —SH, —SCN, $C_1$-$C_6$-alkyl, $C_2$-$C_6$-alkenyl, $C_2$-$C_6$-alkynyl, $C_3$-$C_8$-cycloalkyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 radicals selected from $C_1$-$C_4$-alkoxy;

$C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, —$OR^a$, —$NR^cR^d$, —$S(O)_nR^a$, —$S(O)_n NR^cR^d$, —$C(=O)R^a$, —$C(=O)NR^cR^d$, —$C(=O)OR^b$, —$C(=S)R^a$, —$C(=S)NR^cR^d$, —$C(=S)OR^b$, —$C(=S)SR^b$, —$C(=NR^c)R^b$, —$C(=NR^c)NR^cR^d$, phenyl, benzyl, pyridyl and phenoxy, wherein the last four radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy and $C_1$-$C_6$-haloalkoxy; or two vicinal radicals $R^e$ together form a group =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

$R^f$ is independently selected from the group consisting of halogen, cyano, nitro, —OH, —SH, —SCN, $C_1$-$C_6$-alkyl, $C_2$-$C_6$-alkenyl, $C_2$-$C_6$-alkinyl, $C_3$-$C_8$-cycloalkyl, wherein one or more $CH_2$ groups of the aforementioned radicals may be replaced by a C=O group, and/or the aliphatic and cycloaliphatic moieties of the aforementioned radicals may be unsubstituted, partially or fully halogenated and/or may carry 1 or 2 radicals selected from $C_1$-$C_4$ alkoxy;

$C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, —$OR^a$, —$NR^cR^d$, —$S(O)_nR^a$, —$S(O)_n NR^cR^d$, —$C(=O)R^a$, —$C(=O)NR^cR^d$, —$C(=O)OR^b$, —$C(=S)R^a$, —$C(=S)NR^cR^d$, —$C(=S)OR^b$, —$C(=S)SR^b$, —$C(=NR^c)R^b$, and —$C(=NR^c)NR^cR^d$;

k is 0 or 1;

n is 0, 1 or 2;

or a stereoisomer, salt, tautomer or N-oxide thereof.

2. The compound of claim 1, wherein $R^1$ is selected from the group consisting of chlorine and bromine.

3. The compound of claim 1, wherein $R^2$ is selected from the group consisting of cyano, trifluoromethyl, chlorine and bromine.

4. The compound of claim 1, wherein $R^3$ is hydrogen.

5. The compound of claim 1, wherein $R^4$ is selected from the group consisting of chlorine and bromine.

6. The compound of claim 1, wherein $R^5$ and $R^6$ are selected independently of one another from the group consisting of $C_1$-$C_6$-alkyl, $C_3$-$C_6$-cycloalkyl, $C_2$-$C_6$-alkenyl, $C_2$-$C_6$-alkynyl, wherein the aforementioned radicals may be substituted with 1 to 10 substituents $R^e$, and phenyl, which is unsubstituted or carries 1 to 4 radicals $R^f$, or $R^5$ and $R^6$ together represent a $C_3$-$C_7$-alkylene chain forming together with the sulfur atom to which they are attached a 4-, 5-, 6-, 7- or 8-membered saturated ring, wherein 1 or 2 of the $CH_2$ groups in the $C_3$-$C_7$-alkylene chain may be replaced by 1 or 2 groups independently selected from the group consisting of C=O, C=S, O, S, N, NO, SO, $SO_2$ and NH, and wherein the carbon and/or nitrogen atoms in the $C_3$-$C_7$-alkylene chain may be substituted with 1 to 5 substituents independently selected from the group consisting of halogen, cyano, $C_1$-$C_2$-alkyl, and $C_1$-$C_2$-haloalkyl, said substituents being identical or different from one another if more than one substituent is present.

7. The compound of claim 1, wherein $R^5$ and $R^6$ are selected independently of one another from the group consisting of $C_1$-$C_6$-alkyl, $C_3$-$C_6$-cycloalkyl, $C_2$-$C_6$-alkenyl, $C_2$-$C_6$-alkynyl, wherein the aforementioned radicals may be substituted with 1 to 4 substituents selected from the group consisting of halogen, cyano, $C_1$-$C_6$-alkyl and $C_3$-$C_6$-cycloalkyl; and phenyl, which is unsubstituted or carries 1, 2 or 3 radical selected from the group consisting of halogen, cyano, methyl, methoxy, trifluoromethyl and difluoromethyl, or $R^5$ together with $R^6$ form a bivalent moiety $(CH_2)_m$ where m is from 3 to 7 and wherein one $CH_2$ moiety may be replaced by S, SO or $SO_2$.

8. The compound of claim 1, wherein $R^5$ and $R^6$ are selected independently of one another from the group consisting of $CH_3$, $CH_2CH_3$, $CH=CH_2$, $CH_2CH_2CH_3$, $CH(CH_3)_2$, $CH_2CH_2CH_2CH_3$, $C(CH_3)_3$, $CH_2CH(CH_3)_2$, $CH(CH_3)CH_2CH_3$, $CH_2CH_2CH_2CH_2CH_3$, $CH_2CH_2CH_2CH_2CH_2CH_3$, $CH_2CH_2CH(CH_3)_2$, $CH(CH_3)CH(CH_3)_2$, $CH_2CH_2OH$, $CH_2CH=CH_2$, $CH_2C\equiv CH$, $CH(CH_3)CH=CH_2$, $CHF_2$, $CH_2Cl$, $CH_2CH_2CN$, $CH_2CH_2Cl$, cyclopropyl, cyclobutyl, cyclopentyl, cyclohexyl, cyclopropylmethyl, 1-cyclopropylethyl, 2-cyclopropylethyl, cyclobutylmethyl, cyclopentylmethyl, cyclohexylmethyl and phenyl, or $R^5$ together with $R^6$ form a bivalent moiety selected from the group consisting of $(CH_2)_4$ and $CH_2SCH_2CH_2$.

9. The compound of claim 1, wherein k is 0.

10. The compound of claim 1 having formula (I-a)

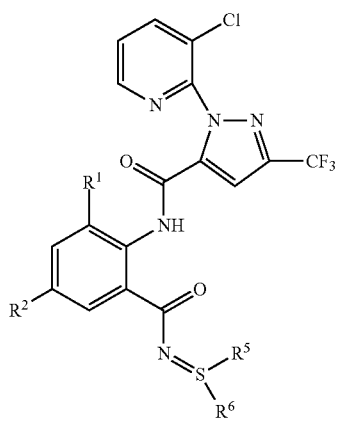

(I-a)

11. The compound of claim 10, wherein $R^1$, $R^2$, $R^5$ and $R^6$ have one of the meanings given in any one of rows 1 to 58 of the following table:

| row | $R^1$ | $R^2$ | $R^5$ | $R^6$ |
|---|---|---|---|---|
| 1 | Cl | Cl | $CH_3$ | $CH_3$ |
| 2 | Cl | CN | $CH_3$ | $CH_3$ |
| 3 | Br | Cl | $CH_3$ | $CH_3$ |
| 4 | Br | Br | $CH_3$ | $CH_3$ |
| 5 | $CF_3$ | Cl | $CH_3$ | $CH_3$ |
| 6 | $CF_3$ | Br | $CH_3$ | $CH_3$ |
| 7 | Cl | Cl | $CH_2CH_2CH_2CH_2$ | |
| 8 | Cl | CN | $CH_2CH_2CH_2CH_2$ | |
| 9 | Br | Cl | $CH_2CH_2CH_2CH_2$ | |
| 10 | Br | Br | $CH_2CH_2CH_2CH_2$ | |
| 11 | $CF_3$ | Cl | $CH_2CH_2CH_2CH_2$ | |
| 12 | $CF_3$ | Br | $CH_2CH_2CH_2CH_2$ | |
| 13 | Cl | Cl | $C_2H_5$ | $C_2H_5$ |
| 14 | Cl | Cl | $CH(CH_3)_2$ | $CH(CH_3)_2$ |
| 15 | Br | Cl | $C_2H_5$ | $C_2H_5$ |
| 16 | Br | Cl | $CH(CH_3)_2$ | $CH(CH_3)_2$ |
| 17 | Br | Br | $C_2H_5$ | $C_2H_5$ |
| 18 | Br | Br | $CH(CH_3)_2$ | $CH(CH_3)_2$ |
| 19 | $CF_3$ | Cl | $C_2H_5$ | $C_2H_5$ |
| 20 | $CF_3$ | Cl | $CH(CH_3)_2$ | $CH(CH_3)_2$ |
| 21 | $CF_3$ | Br | $C_2H_5$ | $C_2H_5$ |
| 22 | $CF_3$ | Br | $CH(CH_3)_2$ | $CH(CH_3)_2$ |
| 23 | Br | $CF_3$ | $C_2H_5$ | $C_2H_5$ |
| 24 | Br | $CF_3$ | $CH(CH_3)_2$ | $CH(CH_3)_2$ |
| 25 | Cl | $CF_3$ | $C_2H_5$ | $C_2H_5$ |
| 26 | Cl | $CF_3$ | $CH(CH_3)_2$ | $CH(CH_3)_2$ |
| 27 | Cl | CN | $C_2H_5$ | $C_2H_5$ |
| 28 | Cl | CN | $CH(CH_3)_2$ | $CH(CH_3)_2$ |
| 29 | Cl | Cl | $CH_2CH(CH_3)_2$ | $CH_2CH(CH_3)_2$ |
| 30 | Cl | CN | $CH_2CH(CH_3)_2$ | $CH_2CH(CH_3)_2$ |
| 31 | Br | Cl | $CH_2CH(CH_3)_2$ | $CH_2CH(CH_3)_2$ |
| 32 | Br | Br | $CH_2CH(CH_3)_2$ | $CH_2CH(CH_3)_2$ |
| 33 | $CF_3$ | Cl | $CH_2CH(CH_3)_2$ | $CH_2CH(CH_3)_2$ |
| 34 | $CF_3$ | Br | $CH_2CH(CH_3)_2$ | $CH_2CH(CH_3)_2$ |
| 35 | Cl | Cl | $CH(CH_3)_2$ | $C_2H_5$ |
| 36 | Cl | CN | $CH(CH_3)_2$ | $C_2H_5$ |
| 37 | Br | Cl | $CH(CH_3)_2$ | $C_2H_5$ |
| 38 | Br | Br | $CH(CH_3)_2$ | $C_2H_5$ |
| 39 | $CF_3$ | Cl | $CH(CH_3)_2$ | $C_2H_5$ |
| 40 | $CF_3$ | Br | $CH(CH_3)_2$ | $C_2H_5$ |
| 41 | Cl | Cl | cyclopropyl | $C_2H_5$ |
| 42 | Cl | CN | cyclopropyl | $C_2H_5$ |
| 43 | Br | Cl | cyclopropyl | $C_2H_5$ |
| 44 | Br | Br | cyclopropyl | $C_2H_5$ |
| 45 | $CF_3$ | Cl | cyclopropyl | $C_2H_5$ |
| 46 | $CF_3$ | Br | cyclopropyl | $C_2H_5$ |
| 47 | Cl | Cl | cyclopropyl | $CH(CH_3)_2$ |
| 48 | Cl | CN | cyclopropyl | $CH(CH_3)_2$ |
| 49 | Br | Cl | cyclopropyl | $CH(CH_3)_2$ |
| 50 | Br | Br | cyclopropyl | $CH(CH_3)_2$ |
| 51 | $CF_3$ | Cl | cyclopropyl | $CH(CH_3)_2$ |
| 52 | $CF_3$ | Br | cyclopropyl | $CH(CH_3)_2$ |
| 53 | Cl | Cl | —$CH_2$—S—$CH_2$—$CH_2$— | |
| 54 | Cl | CN | —$CH_2$—S—$CH_2$—$CH_2$— | |
| 55 | Br | Cl | —$CH_2$—S—$CH_2$—$CH_2$— | |
| 56 | Br | Br | —$CH_2$—S—$CH_2$—$CH_2$— | |
| 57 | $CF_3$ | Cl | —$CH_2$—S—$CH_2$—$CH_2$— | |
| 58 | $CF_3$ | Br | —$CH_2$—S—$CH_2$—$CH_2$— | |

12. The compound of claim 10, wherein $R^1$, $R^2$, $R^5$ and $R^6$ have one of the meanings given in any one of rows 1 to 27 of the following table:

| row | $R^1$ | $R^2$ | $R^5$ | $R^6$ |
|---|---|---|---|---|
| 1 | Cl | Cl | $CH_2$-cyclopropyl | $CH_2$-cyclopropyl |
| 2 | Cl | Cl | $CH_2$-cyclopropyl | $C_2H_5$ |
| 3 | Cl | Cl | $CH_2CH_2CH_3$ | $CH_2CH_2CH_3$ |
| 4 | Cl | Br | $CH(CH_3)_2$ | $CH(CH_3)_2$ |
| 5 | Cl | Cl | $CH_2$-cyclopropyl | i-Pr |
| 6 | Cl | Br | $C_2H_5$ | $C_2H_5$ |
| 7 | Cl | Cl | $CH(CH_3)_2$ | $CH(CH_3)CH(CH_3)_2$ |
| 8 | Cl | Cl | $CH(CH_3)_2$ | $CH(CH_3)$—c-Pr |
| 9 | Cl | Cl | $CH(CH_3)CH(CH_3)_2$ | $CH(CH_3)CH(CH_3)_2$ |
| 10 | Cl | Cl | $CH(CH_3)CH(CH_3)_2$ | $C_2H_5$ |
| 11 | Cl | CN | $CH_2$-cyclopropyl | $CH_2$-cyclopropyl |
| 12 | Cl | CN | $CH_2$-cyclopropyl | $C_2H_5$ |
| 13 | Cl | CN | $CH_2$-cyclopropyl | $CH(CH_3)_2$ |
| 14 | Cl | Cl | $CH_2(CH_2)_3CH_3$ | $CH_2(CH_2)_3CH_3$ |
| 15 | Cl | Cl | $CH_2CH_2CH(CH_3)_2$ | $CH_2CH_2CH(CH_3)_2$ |
| 16 | Cl | Cl | $CH_2$-cyclobutyl | $CH_2$-cyclobutyl |
| 17 | Cl | Cl | $C_2H_5$ | $CH_2$-cyclobutyl |
| 18 | Cl | Cl | $CH_2(CH_2)_4CH_3$ | $CH_2(CH_2)_4CH_3$ |
| 19 | Cl | Cl | $CH_2CH(C_2H_5)(CH_2)_3CH_3$ | $CH_2CH(C_2H_5)(CH_2)_3CH_3$ |
| 20 | Cl | Cl | $CH_2CH_2OH$ | $CH_2CH_2OH$ |
| 21 | Cl | Cl | $CH_2CH_2$-cyclopropyl | $CH_2CH_2$-cyclopropyl |
| 22 | Cl | Cl | $CH_2CH_2$-cyclopropyl | i-Pr |
| 23 | Cl | Cl | $CH_2CH_2$-cyclopropyl | $C_2H_5$ |
| 24 | Cl | Cl | $CH_2$-cyclobutyl | $CH(CH_3)_2$ |
| 25 | Cl | Cl | $CH_2$-cyclopentyl | $CH_2$-cyclopentyl |
| 26 | Cl | Cl | $CH_2$-cyclopentyl | $C_2H_5$ |
| 27 | Cl | Cl | $CH_2$-cyclopentyl | $CH(CH_3)_2$ |

13. The compound of claim 1, which is 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide.

14. A crystalline form of the compound of claim 13, which in an X-ray powder diffractogram at 25° C. and Cu—K$_\alpha$ radiation, shows at least four of the following reflexes, given as 2θ values: 8.07, 9.53, 11.00, 12.40, 14.31, 16.65, 18.97, 21.14, 21.48, 22.48.

15. A pesticidal combination comprising at least one compound of claim 1, and at least one active compound selected from the group consisting of insecticides, acaricides, fungicides, herbicides, plant growth regulators, safeners and nematicides.

16. An agricultural or veterinary composition comprising at least one compound of claim 1.

17. An agricultural or veterinary composition comprising the pesticidal combination of claim 15.

18. A method for combating or controlling invertebrate pests, comprising contacting said pest or its food supply, habitat or breeding grounds with a pesticidally effective amount of at least one compound of claim 1, except for a method performed on humans.

19. A method for combating or controlling invertebrate pests, comprising contacting said pest or its food supply, habitat or breeding grounds with a pesticidally effective amount of the pesticidal combination of claim 15, except for a method performed on humans.

20. A method for combating or controlling invertebrate pests, comprising contacting said pest or its food supply, habitat or breeding grounds with a pesticidally effective amount of the composition of claim 16, except for a method performed on humans.

21. A method for protecting growing plants from attack or infestation by invertebrate pests, comprising contacting a plant, or soil or water in which the plant is growing or may grow, with a pesticidally effective amount of at least one compound of claim 1.

22. A method for protecting growing plants from attack or infestation by invertebrate pests, comprising contacting a plant, or soil or water in which the plant is growing or may grow, with a pesticidally effective amount of the pesticidal compound of claim 15.

23. A method for protecting growing plants from attack or infestation by invertebrate pests, comprising contacting a plant, or soil or water in which the plant is growing or may grow, with a pesticidally effective amount of the composition of claim 16.

24. A method for the protection of seeds from soil insects and of the seedlings' roots and shoots from invertebrate pests comprising contacting the seeds before sowing and/or after pregermination with at least one compound of claim 1.

25. A method for the protection of seeds from soil insects and of the seedlings' roots and shoots from invertebrate pests comprising contacting the seeds before sowing and/or after pregermination with the pesticidal combination of claim 15.

26. A method for the protection of seeds from soil insects and of the seedlings' roots and shoots from invertebrate pests comprising contacting the seeds before sowing and/or after pregermination with the composition of claim 16.

27. A seed treated with the compound of claim 1, in an amount of from 0.1 g to 10 kg per 100 kg of the plant propagation material.

28. A seed treated with the pesticidal combination of claim 15, in an amount of from 0.1 g to 10 kg per 100 kg of the plant propagation material.

29. A method for treating a non-human animal infested or infected by parasites or for preventing a non-human animal from getting infested or infected by parasites or for protecting a non-human animal against infestation or infection by parasites which comprises orally, topically or parenterally administering or applying to the non-human animal a parasitically effective amount of the compound of claim 1.

30. A method for treating a non-human animal infested or infected by parasites or for preventing a non-human animal from getting infested or infected by parasites or for protecting a non-human animal against infestation or infection by parasites which comprises orally, topically or parenterally administering or applying to the non-human animal a parasitically effective amount of the pesticidal combination of claim 15.

31. A method for treating a non-human animal infested or infected by parasites or for preventing a non-human animal from getting infested or infected by parasites or for protecting a non-human animal against infestation or infection by parasites which comprises orally, topically or parenterally administering or applying to the non-human animal a parasitically effective amount of of the composition of claim 16.

* * * * *